US012655151B2

(12) United States Patent
Reddy et al.

(10) Patent No.: US 12,655,151 B2
(45) **Date of Patent: *Jun. 16, 2026**

(54) ION CHANNEL MODULATORS

(71) Applicant: Praxis Precision Medicines, Inc., Boston, MA (US)

(72) Inventors: Kiran Reddy, Boston, MA (US); Gabriel Martinez Botella, Wayland, MA (US); Andrew Mark Griffin, L'Ile Bizard (CA); Brian Edward Marron, Ada, MI (US); Carlos Loya, Cambridge, MA (US)

(73) Assignee: Praxis Precision Medicines, Inc., Boston, MA (US)

(*) Notice: Subject to any disclaimer, the term of this patent is extended or adjusted under 35 U.S.C. 154(b) by 1000 days.

This patent is subject to a terminal disclaimer.

(21) Appl. No.: 17/780,042

(22) PCT Filed: Nov. 25, 2020

(86) PCT No.: PCT/US2020/062179

§ 371 (c)(1),
(2) Date: May 26, 2022

(87) PCT Pub. No.: WO2021/108513

PCT Pub. Date: Jun. 3, 2021

(65) Prior Publication Data

US 2023/0034917 A1 Feb. 2, 2023

Related U.S. Application Data

(60) Provisional application No. 62/940,500, filed on Nov. 26, 2019.

(51) Int. Cl.

| | |
|---|---|
| ***C07D 487/04*** | (2006.01) |
| ***A61K 31/4985*** | (2006.01) |
| ***A61P 25/00*** | (2006.01) |
| ***A61P 25/06*** | (2006.01) |
| ***A61P 25/08*** | (2006.01) |

(52) U.S. Cl.

CPC ........ *C07D 487/04* (2013.01); *A61K 31/4985* (2013.01); *A61P 25/00* (2018.01); *A61P 25/06* (2018.01); *A61P 25/08* (2018.01)

(58) Field of Classification Search

CPC ........ C07D 487/04; A61P 25/06; A61P 25/00; A61P 25/08; A61K 31/4985

See application file for complete search history.

(56) References Cited

U.S. PATENT DOCUMENTS

| | | | | |
|---|---|---|---|---|
| 11,629,146 B2 | | 4/2023 | Reddy et al. | |
| 11,767,325 B2 | * | 9/2023 | Reddy ..................... | A61P 25/00 514/249 |
| 2011/0021521 A1 | | 1/2011 | Corkey et al. | |
| 2015/0038503 A1 | | 2/2015 | Bourotte et al. | |
| 2018/0065971 A1 | | 3/2018 | Rennie et al. | |
| 2020/0377499 A1 | | 12/2020 | Griffin et al. | |
| 2020/0377507 A1 | | 12/2020 | Griffin et al. | |

FOREIGN PATENT DOCUMENTS

| | | | |
|---|---|---|---|
| CL | 2019001481 | A1 | 8/2019 |
| CN | 102725290 | A | 10/2012 |
| CN | 109790167 | A | 5/2019 |
| CN | 110337295 | A | 10/2019 |
| CN | 112423760 | A | 2/2021 |
| CN | 115038442 | A | 9/2022 |
| WO | 2005/003099 | A2 | 1/2005 |
| WO | 2006/072436 | A1 | 7/2006 |
| WO | 2018098491 | A1 | 5/2018 |
| WO | 2018098499 | A1 | 5/2018 |
| WO | 2018/106284 | A1 | 6/2018 |
| WO | 2018187480 | A1 | 10/2018 |
| WO | 2019/076716 | A1 | 4/2019 |
| WO | 2019/232209 | A1 | 12/2019 |
| WO | 2023/211852 | A1 | 11/2023 |

OTHER PUBLICATIONS

US 8,754,103 B2, 06/2014, Corkey et al. (withdrawn)

International Search Report and Written Opinion in corresponding International Application No. PCT/US2020/062179 mailed on Feb. 25, 2021, 7 pages.

Dai et al., Synthesis and Characterization of 7-(3-amino-3-(4-methoxyphenyl)propanoyl)-3-(trifluoromethyl)-5,6,7,8-tetrahydro[1,2,4]triazolo[4,3-alpha]piperazine. Journal of Nanching University (Natural Science). Oct. 2009;33(5):445-451.

Kahlig et al., The novel persistent sodium current inhibitor PRAX-562 has potent anticonvulsant activity with improved protective index relative to standard of care sodium channel blockers. Epilepsia. Mar. 2022;63(3):697-708.

Li et al., Recent Developments on Triazole Nucleus in Anticonvulsant Compounds: a Review. Journal of Liaocheng University (Nat. Sci.). Jun. 2018;31(2):33-42.

* cited by examiner

*Primary Examiner* — Jeffrey S Lundgren

*Assistant Examiner* — Paul Randall Gauger

(74) *Attorney, Agent, or Firm* — McCarter & English, LLP; Jonathan M. Sparks; Yelena Margolin

(57) ABSTRACT

The present invention is directed to, in part, fused heteroaryl compounds and compositions useful for preventing and/or treating a disease or condition relating to aberrant function of a voltage-gated, sodium ion channel, for example, abnormal late/persistent sodium current. Methods of treating a disease or condition relating to aberrant function of a sodium ion channel including neurological disorders (e.g., Dravet syndrome, epilepsy), pain, and neuromuscular disorders are also provided herein.

38 Claims, No Drawings

ION CHANNEL MODULATORS

CROSS-REFERENCE TO RELATED APPLICATIONS

This application is a national stage entry from International Application No. PCT/US2020/062179, filed on Nov. 25, 2020, and claims the benefit of U.S. Provisional Patent Application No. 62/940,500 filed Nov. 26, 2019, the entire contents of which are incorporated by reference herein.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339). Accordingly, pharmaceutical compounds that selectively modulate sodium channel activity, e.g., abnormal INaL, are useful in treating such disease states.

SUMMARY

Described herein are fused heteroaryl compounds and compositions useful for preventing and/or treating a disease, disorder, or condition, e.g., a disease, disorder, or condition relating to aberrant function of a sodium ion channel, e.g., abnormal late/persistent sodium current (INaL).

Thus, in one aspect, provided herein is a compound having the Formula I:

(I)

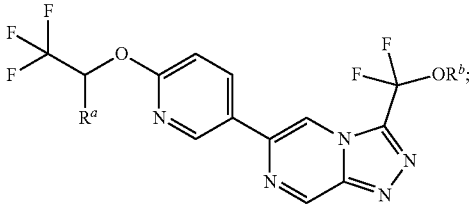

or a pharmaceutically acceptable salt thereof, wherein is $C_{2-4}$alkyl or monocyclic $C_{3-6}$ cycloalkyl; and $R^b$ is $C_{1-4}$alkyl.

In some embodiments, $R^a$ is ethyl, isopropyl, or cyclopropyl. In some embodiments, $R^b$ is methyl or ethyl.

In some embodiments, the compound of Formula I is selected from the group consisting of:

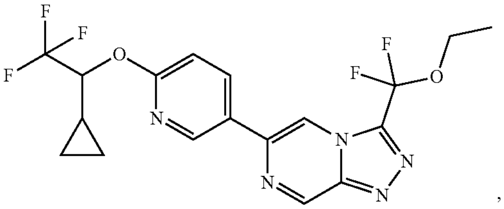

,

-continued

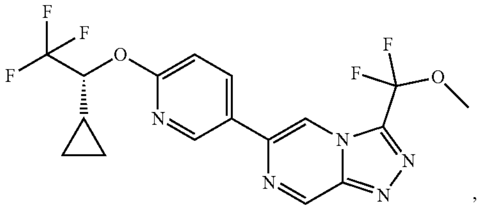

,

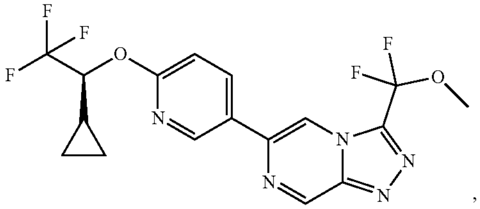

,

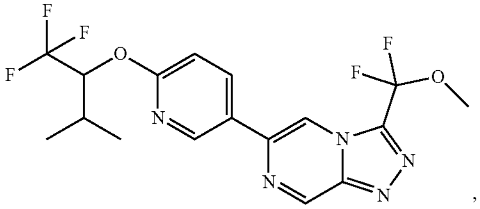

,

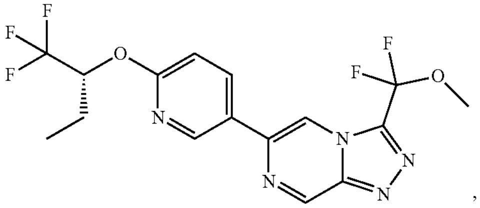

,

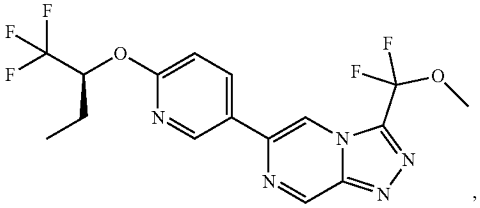

,

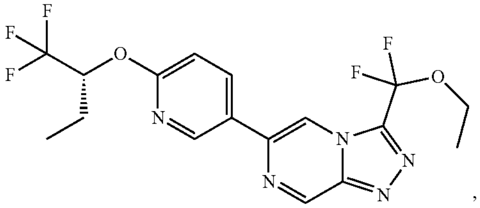

,

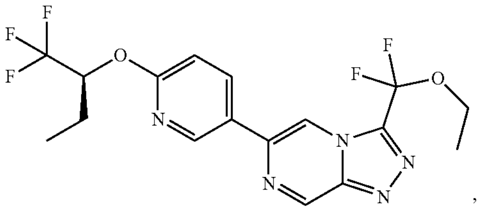

,

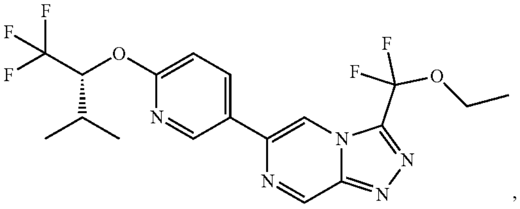

,

-continued

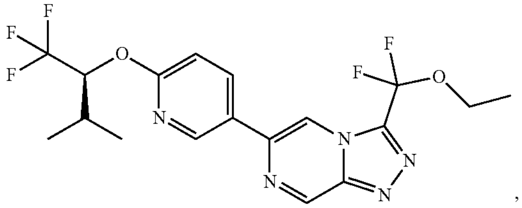

,

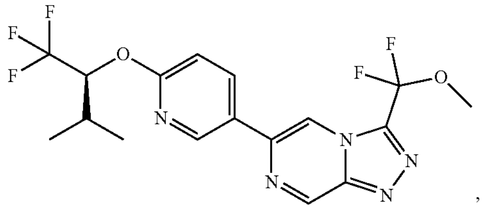

,

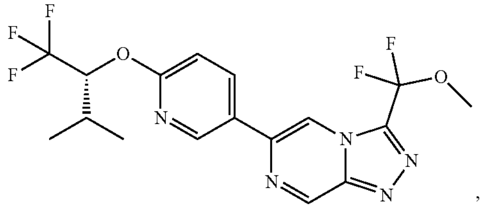

,

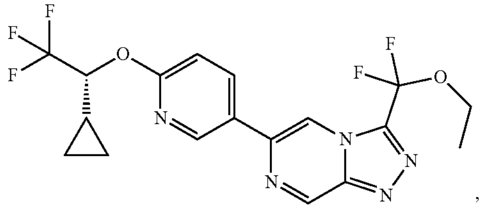

,

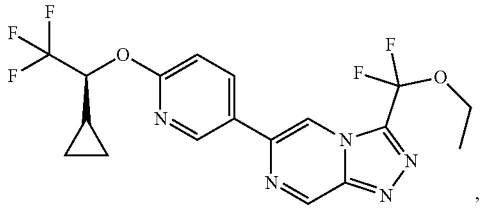

, or a pharmaceutically acceptable salt thereof.

In another aspect, provided herein is a compound having the Formula II:

(II)

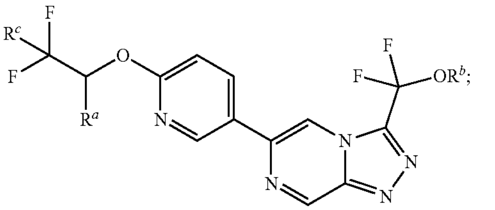

or a pharmaceutically acceptable salt thereof, wherein $R^a$ is $C_{1-4}$alkyl; $R^b$ is $C_{1-4}$alkyl; and $R^c$ is hydrogen or $C_{1-4}$alkyl.

In some embodiments, $R^a$ is methyl. In some embodiments, $R^a$ is methyl or ethyl. In some embodiments, $R^b$ is methyl. In some embodiments, $R^b$ is methyl, ethyl, or isopropyl. In some embodiments, $R^c$ is hydrogen or methyl. In some embodiments, $R^c$ is hydrogen. In some embodiments, $R^c$ is methyl.

In some embodiments, the compound of Formula II is selected from the group consisting of:

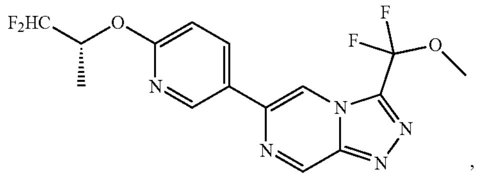

,

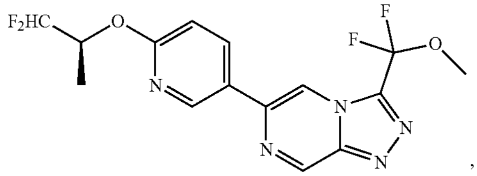

,

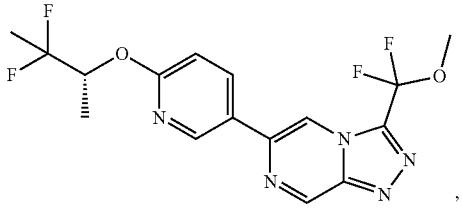

,

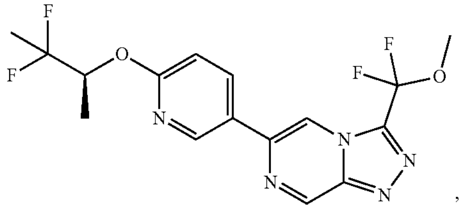

,

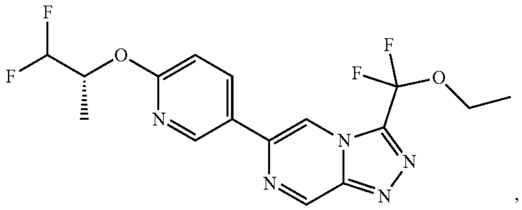

,

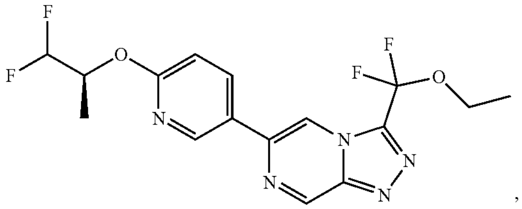

,

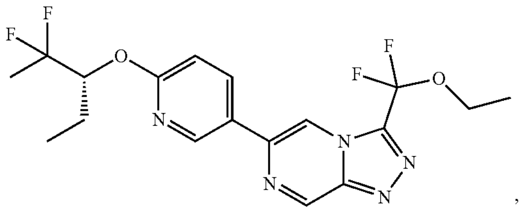

,

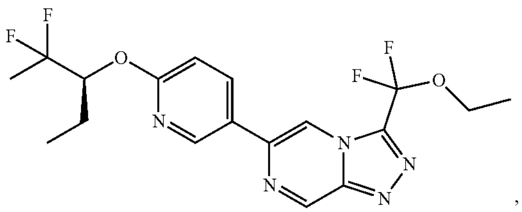

,

-continued

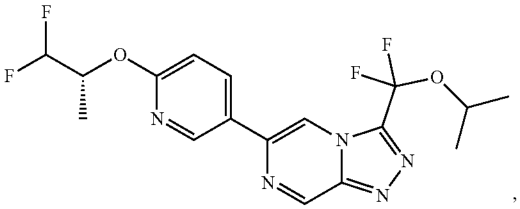
,
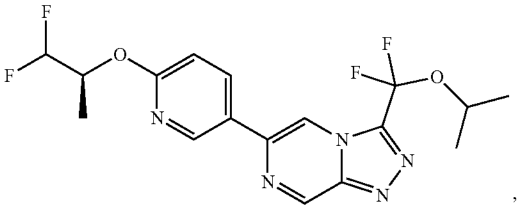
,
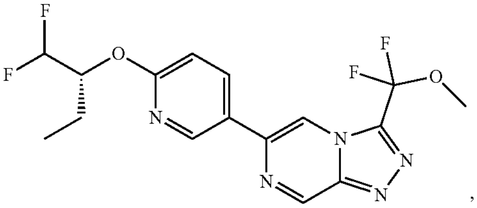
, and
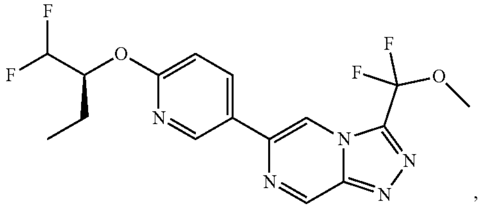
, or pharmaceutically acceptable salt thereof.

In another aspect, provided herein is a compound selected from the group consisting of:

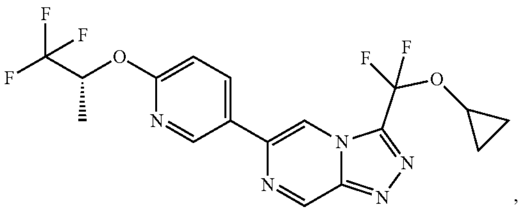
,
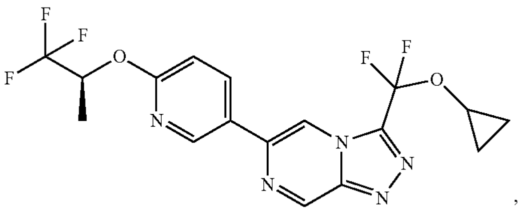
,
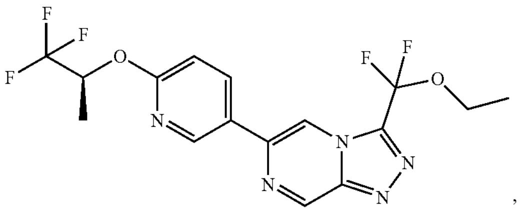
,

-continued

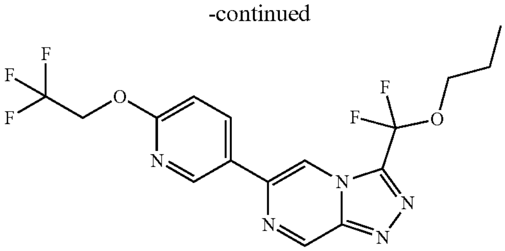
,
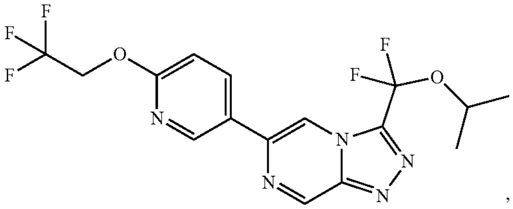
,
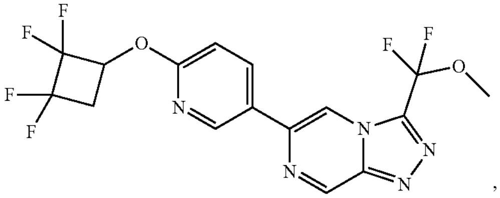
,
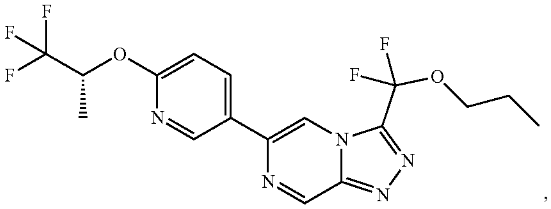
,
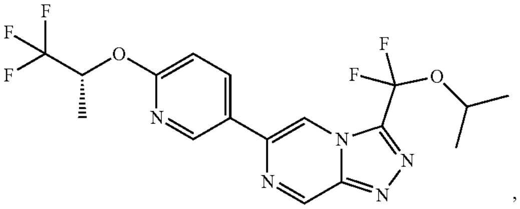
,
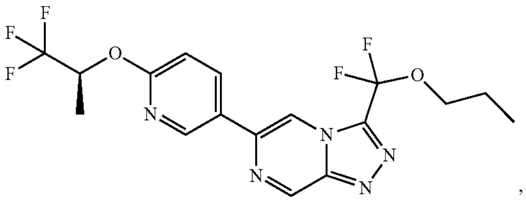
, and
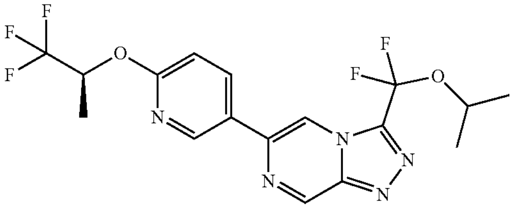

or a pharmaceutically acceptable salt thereof.

Also provided herein is a pharmaceutical composition comprising a compound described herein, or a pharmaceutically acceptable salt thereof; and a pharmaceutically acceptable carrier.

In one aspect, provided herein is a method of treating a condition relating to aberrant function of a sodium ion channel in a subject in need thereof, comprising administering to the subject a therapeutically effective amount of a compound described herein, or a pharmaceutically acceptable salt thereof, or a pharmaceutical composition described herein.

In some embodiments, the condition is a neurological or psychiatric disorder. In some embodiments, the condition is epilepsy or an epilepsy syndrome. In some embodiments, the condition is a genetic epilepsy or a genetic epilepsy syndrome. In some embodiments, the condition is a pediatric epilepsy or a pediatric epilepsy syndrome. In some embodiments, the condition is epileptic encephalopathy. In some embodiments, the epileptic encephalopathy is selected from the group consisting of Dravet syndrome, infantile spasms, or Lennox-Gastaut syndrome.

In some embodiments, the condition is selected from the group consisting of epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

In another aspect, the present invention discloses a method of treating a neurological disorder or a psychiatric disorder, wherein the method comprises administering to a subject in need thereof the compound described herein, or the pharmaceutically acceptable salt thereof, or a pharmaceutical composition described herein.

In another aspect, provided herein is a method of treating a pain, wherein the method comprises administering to a subject in need thereof a compound described herein, or a pharmaceutically acceptable salt thereof, or a pharmaceutical composition described herein.

In another aspect, methods of preventing or treating trigeminal autonomic cephalalgia (e.g., paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania) are provided. Also provided herein are methods of preventing or treating a cranial neuropathy (e.g., bell palsy, microvascular cranial nerve palsy, third nerve palsy, fourth nerve palsy, and sixth nerve palsy) or multiple cranial neuropathies (MCN). In certain embodiments, methods of preventing or treating a migraine (e.g., migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM)) are provided. In some other embodiments, provided herein are methods of preventing or treating cortical spreading depression (CDC).

In one aspect, the present disclosure provides a method of treating or preventing trigeminal autonomic cephalalgia (TAC) in a subject in need thereof, comprising administering to the subject a therapeutically effective amount of a compound described herein, or a pharmaceutically acceptable salt thereof, or a pharmaceutical composition described herein, wherein the TAC is selected from the group consisting of paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania.

In another aspect, provided herein is a method of treating or preventing a migraine in a subject in need thereof, comprising administering to the subject a therapeutically effective amount of a compound described herein, or a pharmaceutically acceptable salt thereof, or a pharmaceutical composition described herein, wherein the migraine is selected from the group consisting of migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM).

In another aspect, the present disclosure provides a method of treating or preventing cortical spreading depression (CSD) in a subject in need thereof, comprising administering to the subject a therapeutically effective amount of a compound described herein, or a pharmaceutically acceptable salt thereof, or a pharmaceutical composition described herein.

In another aspect, the present disclosure provides a method of treating or preventing a cranial neuropathy or multiple cranial neuropathies (MCN) in a subject in need thereof, comprising administering to the subject a therapeutically effective amount of a compound described herein, or a pharmaceutically acceptable salt thereof, or a pharmaceutical composition described herein.

Other objects and advantages will become apparent to those skilled in the art from consideration of the ensuing Detailed Description, Examples, and Claims.

DETAILED DESCRIPTION

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999*; Smith and March, March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkylene" refers to a divalent radical of an alkyl group. When a range or number of carbons is provided for a particular "alkylene" group, it is understood that the range or number refers to the range or number of carbons in the linear carbon divalent chain. "Alkylene" groups may be substituted or unsubstituted with one or more substituents as described herein.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

As used herein, "$C_{3-6}$ monocyclic cycloalkyl" or "monocyclic $C_{3-6}$ cycloalkyl" refers to a 3- to 7-membered monocyclic hydrocarbon ring system that is saturated. 3- to 7-membered monocyclic cycloalkyl groups include, without limitation, cyclopropyl, cyclobutyl, cyclopentyl, and cyclohexyl. Where specified as being optionally substituted or substituted, substituents on a cycloalkyl (e.g., in the case of an optionally substituted cycloalkyl) may be present on any substitutable position and, include, e.g., the position at which the cycloalkyl group is attached.

These and other exemplary substituents are described in more detail in the Detailed Description, Examples, and Claims. The invention is not intended to be limited in any manner by the above exemplary listing of substituents.

Other Definitions

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, provided herein is a compound having the Formula I:

(I)

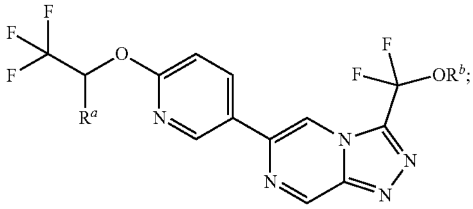

or a pharmaceutically acceptable salt thereof, wherein $R^a$ is $C_{2-4}$alkyl or monocyclic $C_{3-6}$ cycloalkyl; and $R^b$ is $C_{1-4}$alkyl.

In some embodiments, $R^a$ is ethyl, isopropyl, n-propyl, n-butyl, isobutyl, cyclopropyl, cyclobutyl, cyclopentyl, or cyclohexyl. In some embodiments, $R^a$ is ethyl, isopropyl, or cyclopropyl. In some embodiments, $R^a$ is ethyl. In some embodiments, $R^a$ is isopropyl or cyclopropyl. In some embodiments, $R^a$ is isopropyl. In some embodiments, $R^a$ is cyclopropyl. In some embodiments, $R^b$ is methyl, ethyl, isopropyl, n-propyl, n-butyl, or isobutyl. In some embodiments, $R^b$ is methyl or ethyl. In some embodiments, $R^b$ is methyl. In some embodiments, $R^b$ is ethyl.

In some embodiments, the compound of Formula I is selected from the group consisting of:

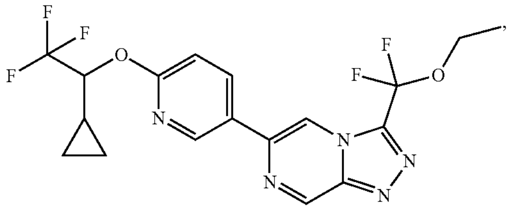

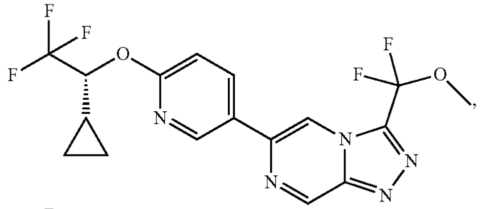

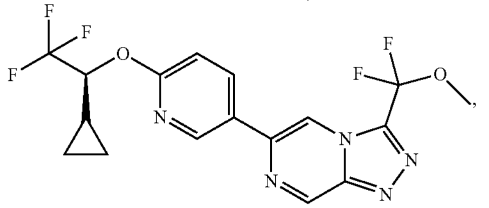

-continued

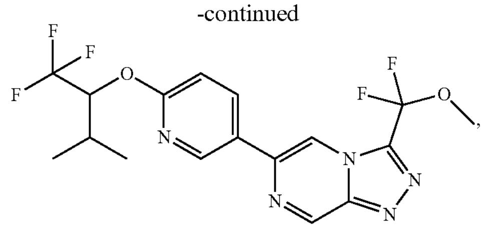

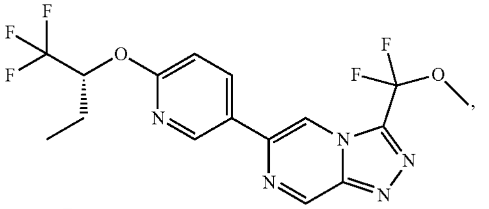

and

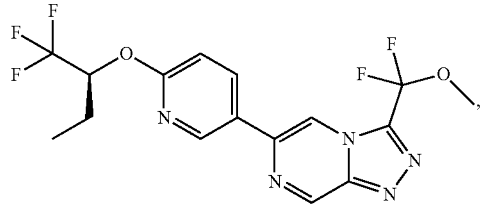

or a pharmaceutically acceptable salt thereof.

In another aspect, provided herein is a compound having the Formula II:

(II)

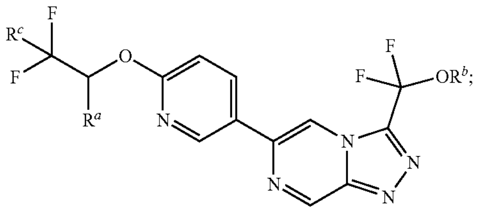

or a pharmaceutically acceptable salt thereof, wherein $R^a$ is $C_{1-4}$alkyl; $R^b$ is $C_{1-4}$alkyl; and $R^c$ is hydrogen or $C_{1-4}$alkyl.

In some embodiments, $R^a$ is methyl, ethyl, n-propyl, isopropyl, n-butyl, or isobutyl. In some embodiments, $R^a$ is methyl or ethyl. In some embodiments, $R^a$ is methyl. In some embodiments, $R^a$ is ethyl. In some embodiments, $R^b$ is methyl, ethyl, n-propyl, isopropyl, n-butyl, or isobutyl. In some embodiments, $R^b$ is methyl, ethyl, or isopropyl. In some embodiments, $R^b$ is methyl. In some embodiments, $R^b$ is ethyl. In some embodiments, $R^b$ is isopropyl. In some embodiments, $R^c$ is hydrogen, methyl, ethyl, isopropyl, n-propyl, isobutyl, or n-butyl. In some embodiments, $R^c$ is hydrogen or methyl. In some embodiments, $R^c$ is hydrogen. In some embodiments, $R^c$ is methyl.

In some embodiments, the compound of Formula II is selected from the group consisting of:

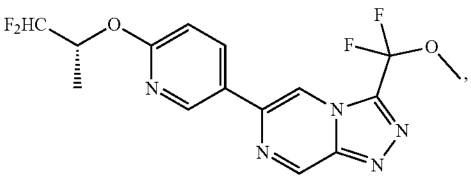

-continued
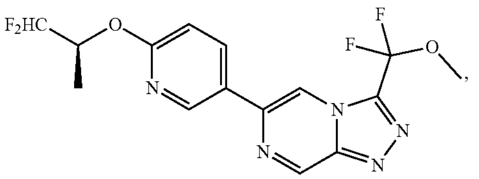
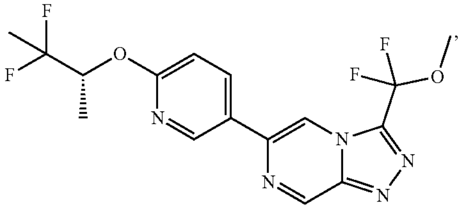
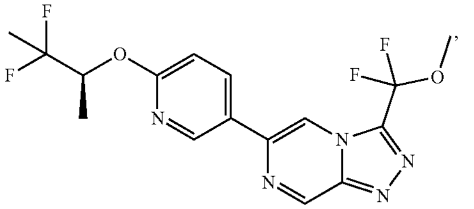
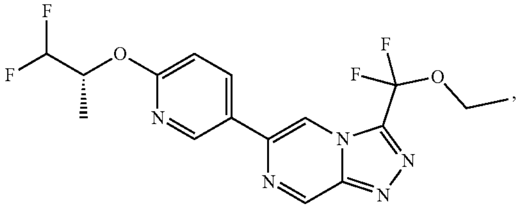
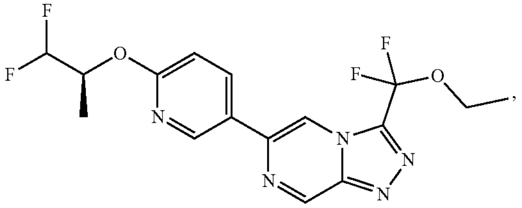
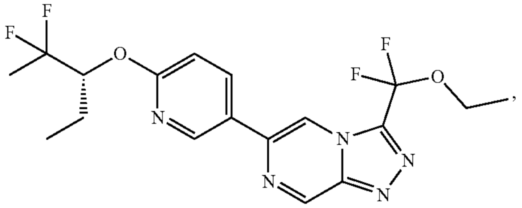
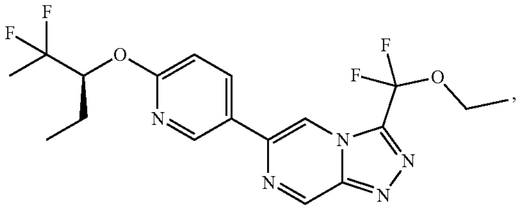
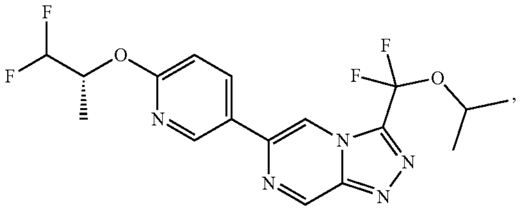
-continued
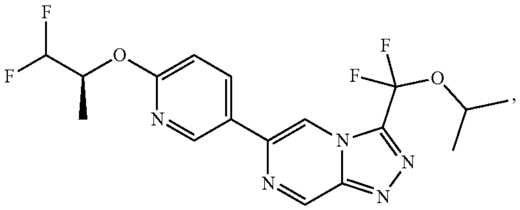
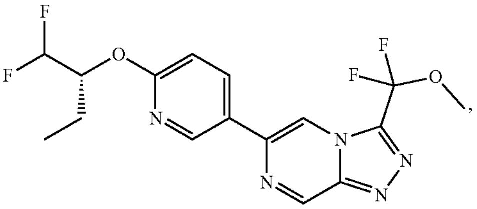
and
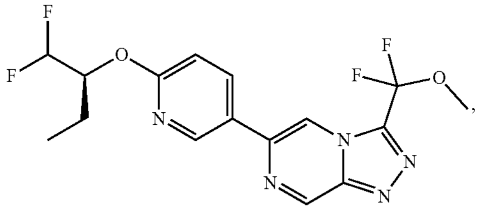
or a pharmaceutically acceptable salt thereof.
In another aspect, provided herein is a compound selected from the group consisting of:
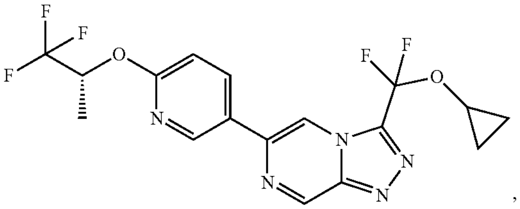
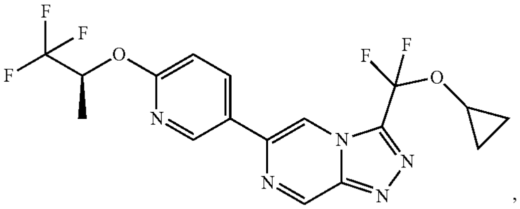
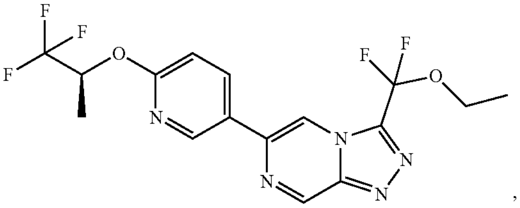
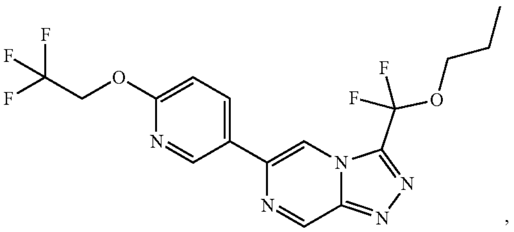

-continued

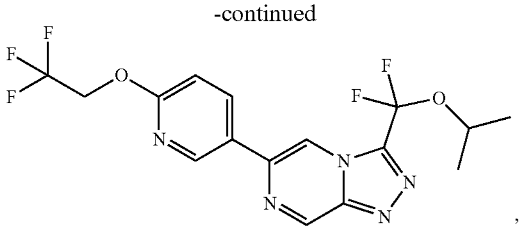

,

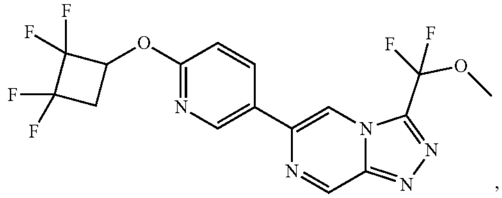

,

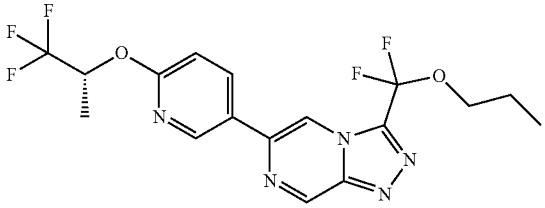

,

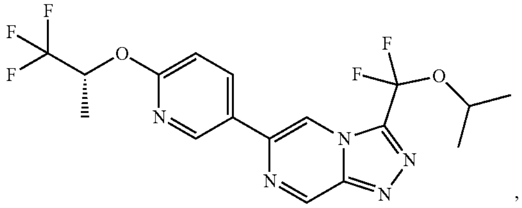

,

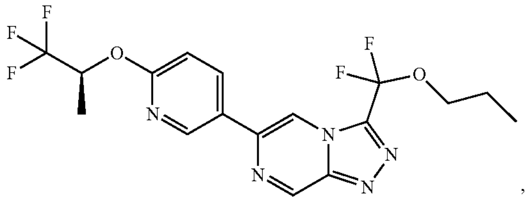

, and

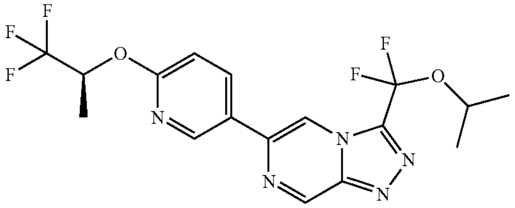

or a pharmaceutically acceptable salt thereof.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprises a disclosed compound, or pharmaceutically acceptable salt thereof, and a pharmaceutically acceptable carrier.

Methods of Treatment

Compounds and compositions described herein are generally useful for the modulating the activity of sodium channels and are useful in treating conditions relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. In some embodiments, a compound provided by the present invention is effective in the treatment of neuropathy such as cranial neuropathy and pain such as migraines, trigeminal autonomic cephalalgias, and cortical spreading depression. A provided compound, pharmaceutically acceptable salt thereof, or composition may also modulate all sodium ion channels, or may be specific to only one or a plurality of sodium ion channels, e.g., Nav 1.1, 1.2, 1.3, 1.4, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein (e.g., a compound of Formula I or II).

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and may actually turn blue. The return to consciousness is gradual and the person maybe confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein (e.g., a compound of Formula I or II) may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden unexpected death in epilepsy (SUDEP), KCNQ2 epileptic encephalopathy, or KCNT1 epileptic encephalopathy) prior to administration of a compound described herein (e.g., a compound of Formula I or II).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I) or a compound of Formula (II).

A compound of the present invention (e.g., a compound of Formula I or II) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula I or II).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula I or II).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I) or a compound of Formula (II).

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, or a related headache disorder) prior to administration of a compound described herein (e.g., a compound of Formula I or II).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, or a related headache disorder) comprising administering to a subject in need thereof a compound of Formula (I) or a compound of Formula (II).

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula I or II).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I) or a compound of Formula (II).

Trigeminal Autonomic Cephalalgia

The compounds described herein are useful in the treatment of trigeminal autonomic cephalalgias (TACs). TACs are a group of primary headaches characterized by unilaterality of pain, a relatively short duration of symptoms, and associated ipsilateral cranial autonomic signs. TACs may include cluster headache (CH), paroxysmal hemicrania (PH), hemicrania continua (HC), short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania (LASH). Despite their common elements, the trigeminal autonomic cephalalgias differ, e.g., in attack duration and frequency and in the response to therapy.

In some embodiments, the present invention provides a method of treating PH, HC, SUNCT, SUNA, and/or LASH using a compound described herein, or a pharmaceutically acceptable salt thereof, or a pharmaceutical composition described herein. In some embodiments, the present invention provides a method of treating SUNCT using a compound described herein, or a pharmaceutically acceptable salt thereof, or a pharmaceutical composition described herein. In some embodiments, the present invention provides a method of treating SUNA using a compound described herein, or a pharmaceutically acceptable salt thereof, or a pharmaceutical composition described herein.

In some embodiments, the present invention provides a method of treating TAC (e.g., PH, HC, SUNCT, SUNA, or LASH) comprising administering to a subject in need thereof a therapeutically effective amount of a compound described herein (e.g., a compound of Formula (I) or a compound of Formula (II)), or a pharmaceutically acceptable salt thereof, or a pharmaceutical composition described herein.

In one aspect, provided herein is a method of treating or preventing trigeminal autonomic cephalalgia (TAC) in a subject in need thereof, comprising administering to the subject a therapeutically effective amount of a compound described herein, or a pharmaceutically acceptable salt thereof, or a pharmaceutical composition described herein, wherein the TAC is selected from the group consisting of paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania.

In some embodiments, the subject may have an inadequate response to at least one medication (e.g., lidocaine, triptans, lamotrigine, topiramate, or gabapentin, or any combinations thereof) used for the treatment of a TAC (e.g., PH, HC, SUNCT, SUNA, or LASH).

In some embodiments, the methods described herein further comprise identifying a subject having a TAC (e.g., PH, CH, SUNCT, SUNA, or LASH) prior to the administration of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein, for use in treating TAC (e.g., PH, HC, SUNCT, SUNA, or LASH) in a subject, wherein the treatment comprises administering a therapeutically effective amount of a compound described herein, or a pharmaceutically acceptable salt thereof, or a pharmaceutical composition described herein.

In some embodiments, the present invention provides the use of a compound described herein (e.g., a compound of Formula I of Formula II), or a pharmaceutically acceptable salt thereof, or a pharmaceutical composition described herein, for the manufacture of a medicament for use in treating TAC (e.g., PH, HC, SUNCT, SUNA, or LASH) in a subject, wherein the treatment comprises administering a therapeutically effective amount of a compound described herein, or a pharmaceutically acceptable salt thereof, or a pharmaceutical composition described herein.

Migraines

The compounds described herein are useful in the treatment of migraines. Migraine is a primary headache disorder characterized by recurrent headaches that are moderate to severe. As described herein, a migraine may be migraine without aura, migraine with aura, hemiplegic migraine, familial hemiplegic migraine (FHM), familial hemiplegic migraine type 1 (FHM1), familial hemiplegic migraine type 2 (FHM2), familial hemiplegic migraine type 3 (FHM3), familial hemiplegic migraine type 4 (FHM4), and sporadic hemiplegic migraine (SHM).

In some embodiments, the present invention provides a method of treating migraine without aura, migraine with aura, hemiplegic migraine, FHM, FHM1, FHM2, FHM3, FHM4, and/or SHM using a compound described herein, or a pharmaceutically acceptable salt thereof, or a pharmaceutical composition described herein. In some embodiments, the present invention provides a method of treating migraine without aura, migraine with aura, FHM1, FHM2, FHM4, and/or SHM using a compound described herein, or a pharmaceutically acceptable salt thereof, or a pharmaceutical composition described herein. In some embodiments, the present invention provides a method of treating migraine without aura using a compound described herein, or a pharmaceutically acceptable salt thereof, or a pharmaceutical composition described herein. In some embodiments, the present invention provides a method of treating migraine with aura using a compound described herein, or a pharmaceutically acceptable salt thereof, or a pharmaceutical composition described herein. In some embodiments, the present invention provides a method of treating FHM1, FHM2, and/or FHM4 using a compound described herein, or a pharmaceutically acceptable salt thereof, or a pharmaceutical composition described herein. In some embodiments, the present invention provides a method of treating SHM using a compound described herein, or a pharmaceutically acceptable salt thereof, or a pharmaceutical composition described herein.

In some embodiments, the present invention provides a method of treating migraine (e.g., migraine without aura, migraine with aura, FHM1, FHM2, FHM4, or SHM) comprising administering to a subject in need thereof a therapeutically effective amount of a compound described herein (e.g., a compound of Formula I or Formula II), or a pharmaceutically acceptable salt thereof, or a pharmaceutical composition described herein.

In another aspect, the present disclosure provides a method of treating or preventing a migraine in a subject in need thereof, comprising administering to the subject a therapeutically effective amount of a compound described herein, or a pharmaceutically acceptable salt thereof, or a pharmaceutical composition described herein, wherein the migraine is selected from the group consisting of migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM).

In some embodiments, the subject has an inadequate response to at least one medication for the treatment of a migraine (e.g., migraine without aura, migraine with aura, FHM1, FHM2, FHM4, or SHM).

In some embodiments, the methods described herein further comprise identifying a subject having a migraine (e.g., migraine without aura, migraine with aura, FHM1, FHM2, FHM4, or SHM) prior to the administration of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein, for use in treating migraine (e.g., migraine without aura, migraine with aura, FHM1, FHM2, FHM4, or SHM) in a subject, wherein the treatment comprises administering a therapeutically effective amount of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein, for the manufacture of a medicament for use in treating migraine (e.g., migraine without aura, migraine with aura, FHM1, FHM2, FHM4, or SHM) in a subject, wherein the treatment comprises administering a therapeutically effective amount of a compound described herein, or a pharmaceutically acceptable salt thereof, or a pharmaceutical composition described herein.

Cortical Spreading Depression

The compounds described herein are useful in the treatment of cortical spreading depression (CSD). CSD is a wave of sustained depolarization (neuronal inactivation) moving through intact brain tissue and involved in, for example, brain ischemia, migraine aura, and seizures.

In some embodiments, the present invention provides a method of treating CSD using a compound described herein, or a pharmaceutically acceptable salt thereof, or a pharmaceutical composition described herein. In some embodiments, the present invention provides a method of treating CSD comprising administering to a subject in need thereof a therapeutically effective amount of a compound described herein (e.g., a compound of Formula I or Formula II), or a pharmaceutically acceptable salt thereof, or a pharmaceutical composition described herein.

In another aspect, provided herein is a method of treating or preventing cortical spreading depression (CSD) in a subject in need thereof, comprising administering to the subject a therapeutically effective amount of a compound described herein, or a pharmaceutically acceptable salt thereof, or a pharmaceutical composition described herein.

In some embodiments, the subject may have an inadequate response to at least one medication for the treatment of CSD.

In some embodiments, the methods described herein further comprise identifying a subject having a CSD prior to the administration of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein, for use in treating CSD in a subject, wherein the treatment comprises administering a therapeutically effective amount of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein for the manufacture of a medicament for use in treating CSD in a subject, wherein the treatment comprises administering a therapeutically effective amount of a compound described herein, or a pharmaceutically acceptable salt thereof, or a pharmaceutical composition described herein.

Cranial Neuropathy

The compounds described herein are useful in the treatment of cranial neuropathy. Neuropathy is a disorder of nerve damage and affects the ability to feel and move. When nerves in the brain or brainstem are affected, it is called cranial neuropathy. The cranial nerves are those that arise directly from the brain or brainstem and often affect areas like the face and eyes. Cranial neuropathies include Bell's palsy, microvascular cranial nerve palsy, third nerve palsy, fourth nerve palsy, and sixth nerve palsy. When several different cranial nerves are affected, it is called multiple cranial neuropathies (MCN).

In some embodiments, the present invention provides a method of treating cranial neuropathy (e.g., Bell's palsy, microvascular cranial nerve palsy, third nerve palsy, fourth nerve palsy, or sixth nerve palsy) or MCN comprising administering to a subject in need thereof a therapeutically effective amount of a compound described herein (e.g., a compound of Formula or Formula II), or a pharmaceutically acceptable salt thereof, or a pharmaceutical composition described herein.

Also provided herein is a method of treating or preventing cranial neuropathy in a subject in need thereof, comprising administering to the subject a therapeutically effective amount of a compound described herein, or a pharmaceutically acceptable salt thereof, or a pharmaceutical composition described herein, wherein the cranial neuropathy is selected from the group consisting of bell palsy, microvascular cranial nerve palsy, third nerve palsy, fourth nerve palsy, and sixth nerve palsy.

In some embodiments, the subject may have an inadequate response to at least one medication for the treatment of cranial neuropathy (e.g., Bell's palsy, microvascular cranial nerve palsy, third nerve palsy, fourth nerve palsy, or sixth nerve palsy) or MCN.

In some embodiments, the methods described herein further comprise identifying a subject having a cranial neuropathy (e.g., Bell's palsy, microvascular cranial nerve palsy, third nerve palsy, fourth nerve palsy, or sixth nerve palsy) or MCN prior to the administration of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein, for use in treating (e.g., Bell's palsy, microvascular cranial nerve palsy, third nerve palsy, fourth nerve palsy, or sixth nerve palsy) or MCN in a subject, wherein the treatment comprises administering a therapeutically effective amount of a compound described herein, or a pharmaceutically acceptable salt thereof, or a pharmaceutical composition described herein.

In some embodiments, the present invention provides the use of a compound described herein (e.g., a compound of Formula I or Formula II), or a pharmaceutically acceptable salt thereof, or a pharmaceutical composition described herein, for the manufacture of a medicament for use in treating (e.g., Bell's palsy, microvascular cranial nerve palsy, third nerve palsy, fourth nerve palsy, or sixth nerve palsy) or MCN in a subject, wherein the treatment comprises administering a therapeutically effective amount of a compound described herein, or a pharmaceutically acceptable salt thereof, or a pharmaceutical composition described herein.

Other Disorders

In some embodiments, a compound of the present invention (e.g., a compound of Formula I or II) may have appropriate pharmacokinetic properties such that they may be active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, recurrent ischemia, cerebral ischemia, stroke, renal ischemia, ischemia associated with organ transplant, acute coronary syndrome, peripheral arterial disease, intermittent claudication, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy. In some embodiments, a disclosed method comprises administering the pharmaceutical composition.

In some embodiments, provided herein is a method of treating a neurological disorder or a psychiatric disorder, wherein the method comprises administering to a subject in need thereof a compound disclosed herein, or a pharmaceutically acceptable salt thereof or a pharmaceutical composition disclosed herein.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (lnspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amioarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section “Cardiovascular Agent Combination Therapy” above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the Nav 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban). Antidepressant and anti-anxiety agents may include neuroactive steroid and ketamine and related NMDA receptor antagonists.

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXEMPLIFICATION

The representative examples that follow are intended to help illustrate the invention, and are not intended to, nor should they be construed to, limit the scope of the invention.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate Cis (2.1 mm×30 mm, 3 μm); A=$H_2O$ (0.04% TFA) and B=$CH_3CN$ (0.02% TFA); 50° C.; 1.2 mL/min; 10-80% B over 0.9 minutes, then 80% B for 0.6 minutes) and Method B (Chromolith Flash RP-18 end-capped $C_{18}$ (2 mm×25 mm); A=$H_2O$ (0.04% TFA) and B=$CH_3CN$ (0.02% TFA); 50° C.; 1.5 mL/min; 5-95% B over 0.7 minutes, then 95% B for 0.4 minutes)

List of Abbreviations $Pd(dppf)Cl_2$ [1,1'-bis(diphenylphosphino)ferrocene]palladium(II) dichloride
MeOH methanol
EtOH ethanol
THF tetrahydrofuran
DCM dichloromethane
AcN or MeCN acetonitrile
EtOAc ethyl acetate
PE petroleum ether
DMSO dimethyl sulfoxide
TFA trifluoroacetic acid
DEA diethylamine
KOAc potassium acetate
TBAF tetra-n-butylammonium fluoride
LAH lithium aluminium hydride
DAST diethylaminosulfur trifluoride Example 1. Synthesis of Compound 1: (R)-3-(cyclopropoxydifluoromethyl)-6-(6-((1,1,1-trifluoropropan-2-yl)oxy)pyridin-3-yl)-[1,2,4]triazolo[4,3-a]pyrazine

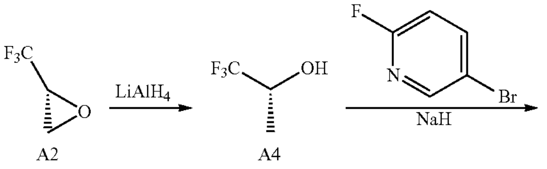

A2 A4

-continued

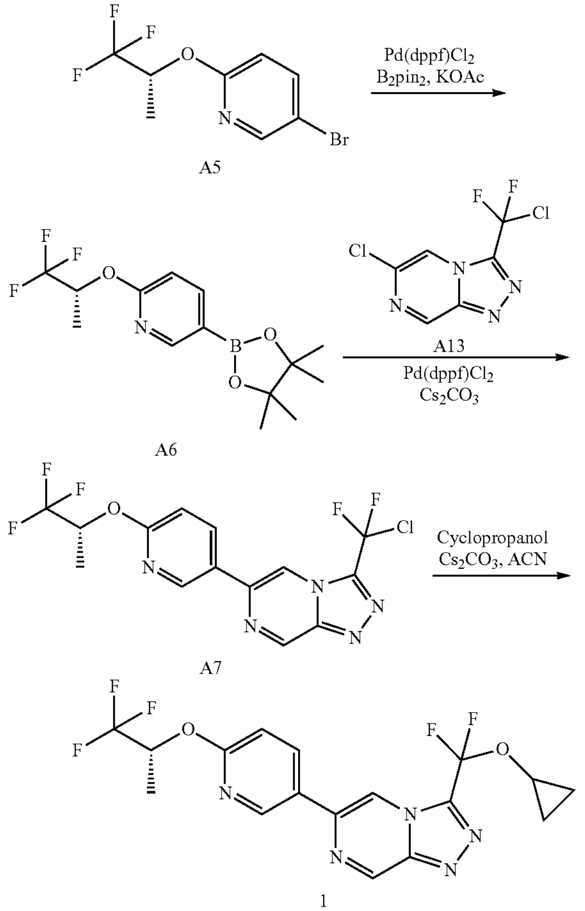

A5

A13

A6

A7

1

A4: (R)-1,1,1-trifluoropropan-2-ol

To a solution of (R)-2-(trifluoromethyl)oxirane (2.2 g, 19.63 mmol) in THF (20.0 mL) was added $LiAlH_4$ (2.0 M in THF, 4.91 mL, 9.82 mmol) dropwise at 0° C. The reaction mixture was slowly warmed to room temperature and stirred for 3 hours. The reaction mixture was cooled to 0° C. and treated with sat $Na_2SO_4$ solution (2.0 mL). The reaction mixture was filtered through celite. The filtrate was dried over $Na_2SO_4$ and used for the next step as a solution in THF.

A5: (R)-5-bromo-2-((1,1,1-trifluoropropan-2-yl)oxy)pyridine

To a solution of (R)-1,1,1-trifluoropropan-2-ol (30.68 mmol) in THF was added NaH (1.84 g, 46 mmol) portion wise at 0° C. and stirred for 30 min. 5-Bromo-2-fluoropyridine (4.32 g, 24.55 mmol) was added to the reaction mixture slowly at stirred at 0° C. The reaction mixture was slowly warmed to room temperature and stirred for 3 hours. The reaction mixture was cooled to 10° C., treated with ice water (10 mL) and extracted with EtOAc (2×50 mL). The organic layer was washed with brine (40 mL), dried over $Na_2SO_4$ and concentrated to give a crude product. The crude product was purified by column chromatography on silica gel with 20% EtOAc/PE to afford (R)-5-bromo-2-((1,1,1-trifluoropropan-2-yl)oxy)pyridine (3.1 g, 11.5 mmol, 37% yield) as a liquid. LCMS: 270.0 $(M+H)^+$ and 272.0 $(M+2+H)^+$, Rt 2.78 min; Column: ZORBAX XDB C-18 (50×4.6 mm), 3.5 μm; Mobile Phase: A: 0.1% HCOOH in water: ACN (95:5), B: ACN; Flow Rate: 1.5 mL/min.

A6: (R)-5-(4,4,5,5-tetramethyl-1,3,2-dioxaborolan-2-yl)-2-((1,1,1-trifluoropropan-2-yl)oxy)pyridine To a stirred solution of (R)-5-bromo-2-((1,1,1-trifluoropropan-2-yl)oxy)pyridine (3.1 g, 11.5 mmol) and bis(pinacolato)diboron (3.79 g, 14.92 mmol) in 1,4-dioxane (35.0 mL) was added potassium acetate (2.25 g, 22.96 mmol). Pd(dppf)$Cl_2$.DCM (1.41 g, 1.72 mmol) was added to the reaction mixture under nitrogen atmosphere and heated at 90° C. for 12 hours. The reaction mixture was cooled to room temperature, filtered through celite and concentrated under reduced pressure. The crude product was purified by column chromatography on silica gel with 6% EtOAc/PE to afford (R)-5-(4,4,5,5-tetramethyl-1,3,2-dioxaborolan-2-yl)-2-((1,1,1-trifluoropropan-2-yl)oxy)pyridine (2.8 g, 8.83 mmol, 76% yield) as a solid. LCMS: 318.0 (M+H), Rt 4.04 min; Column: ZORBAX Extend (50×4.6 mm), 5 μm; Mobile Phase: A: 10 mM Ammonium acetate in water, B: ACN; Flow Rate: 1.2 mL/min.

A7: (R)-3-(chlorodifluoromethyl)-6-(6-((1,1,1-trifluoropropan-2-yl)oxy)pyridin-3-yl)-[1,2,4]triazolo[4,3-a]pyrazine To a stirred solution of (R)-5-(4,4,5,5-tetramethyl-1,3,2-dioxaborolan-2-yl)-2-((1,1,1-trifluoropropan-2-yl)oxy)pyridine (0.5 g, 1.58 mmol) and 6-chloro-3-(chlorodifluoromethyl)-[1,2,4]triazolo[4,3-a]pyrazine (0.45 g, 1.89 mmol) in 1,4-dioxane (12.0 mL) was added water (2.0 mL) and $Cs_2CO_3$ (1.03 g, 3.15 mmol). Pd(dppf)$Cl_2$.DCM (0.11 g, 0.16 mmol) was added to the reaction mixture under nitrogen atmosphere and heated at 90° C. for 16 hours. The reaction mixture was cooled to room temperature, filtered through celite and concentrated under reduced pressure. The crude product was purified by column chromatography on silica gel with 15% EtOAc/PE to afford (R)-3-(chlorodifluoromethyl)-6-(6-((1,1,1-trifluoropropan-2-yl)oxy)pyridin-3-yl)-[1,2,4]triazolo[4,3-a]pyrazine (350 mg, 0.89 mmol, 56% yield) as a solid. LCMS: 394.1 (M+H), Rt 2.54 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Compound 1: (R)-3-(cyclopropoxydifluoromethyl)-6-(6-((1,1,1-trifluoropropan-2-yl)oxy)pyridin-3-yl)-[1,2,4]triazolo[4,3-a]pyrazine To a stirred suspension of $Cs_2CO_3$ (744 mg, 2.29 mmol) in MeCN (10 mL) was added cyclopropanol (0.29 mL, 4.57 mmol) at room temperature and stirred for 15 min. To the reaction mixture (R)-3-(chlorodifluoromethyl)-6-(6-((1,1,1-trifluoropropan-2-yl)oxy)pyridin-3-yl)-[1,2,4]triazolo[4,3-a]pyrazine (150 mg, 0.38 mmol) in MeCN (5.0 mL) was added dropwise and stirred for 2 hours. The reaction mixture was treated with water (30 mL) and extracted with EtOAc (2×30 mL). The organic layer was washed with brine (20 mL), dried over $Na_2SO_4$ and concentrated to give a crude product. The crude product was purified by column chromatography on silica gel with 20% EtOAc/PE to afford 1 (12 mg, 0.03 mmol, 7% yield) as a solid. HPLC: Rt 5.33 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 416.0 (M+H), Rt 2.58 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, DMSO-$d_6$): $\delta_H$=9.64 (d, 1H), 8.84 (d, 1H), 8.77 (s, 1H), 8.42 (dd, 1H), 7.06 (d, 1H), 5.94-5.91 (m, 1H), 4.18-4.15 (m, 1H), 1.43 (d, 3H), 0.88-0.85 (m, 2H), 0.69-0.67 (m, 2H).

Example 2. Synthesis of Compound 2: (S)-3-(cyclopropoxydifluoromethyl)-6-(6-((1,1,1-trifluoropropan-2-yl)oxy) pyridine-3-yl)-[1,2,4]triazolo[4,3-a] pyrazine

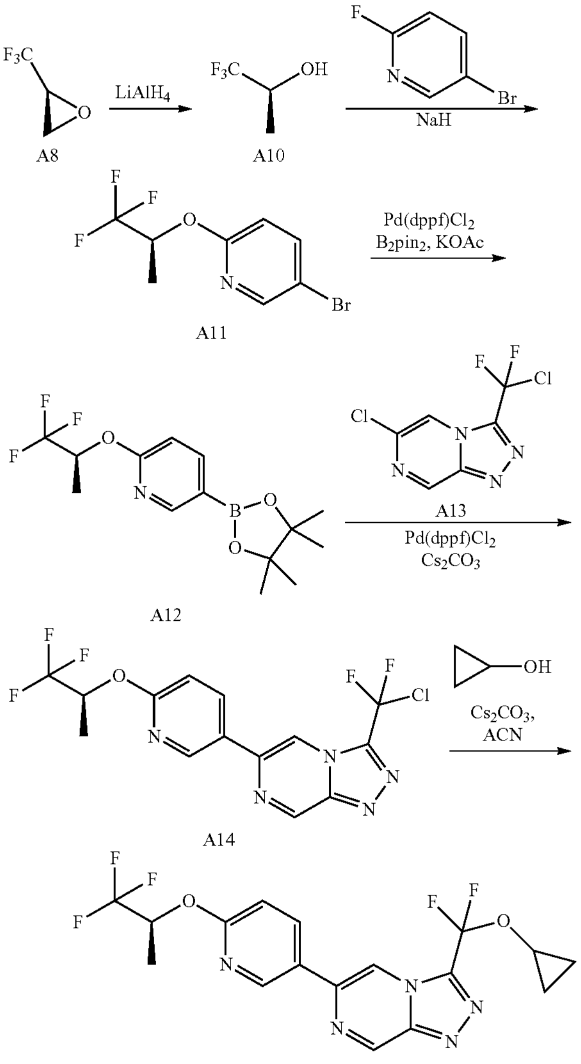

2

A10: (S)-1,1,1-trifluoropropan-2-ol

To a solution of (S)-2-(trifluoromethyl)oxirane (4.0 g, 35.7 mmol) in THF (20.0 mL) was added $LiAlH_4$ (2.0 M in THF, 8.92 mL, 17.85 mmol) dropwise at 0° C. The reaction mixture was slowly warmed to room temperature and stirred for 3 hours. The reaction mixture was cooled to 0° C. and treated with saturated $Na_2SO_4$ solution (2.0 mL). The reaction mixture was filtered through celite, and the filtrate was dried over $Na_2SO_4$ and used for the next step as a solution in THF.

A11: (S)-5-bromo-2-((1,1,1-trifluoropropan-2-yl)oxy)pyridine

To a solution of (S)-1,1,1-trifluoropropan-2-ol (26.3 mmol) in THF was added NaH (1.57 g, 39.45 mmol) portion wise at 0° C. and stirred for 30 min. 5-bromo-2-fluoro-pyridine (3.7 g, 21.04 mmol) was added to the reaction mixture slowly at 0° C. The reaction mixture was slowly warmed to room temperature and stirred for 3 hours. The reaction mixture was cooled to 10° C., treated with ice water (10 mL) and extracted with EtOAc (2×50 mL). The organic layer was washed with brine (40 mL), dried over $Na_2SO_4$ and concentrated to give a crude product. The crude product was purified by column chromatography on silica gel with 20% EtOAc/PE to afford (S)-5-bromo-2-((1,1,1-trifluoro-propan-2-yl)oxy)pyridine (1.6 g, 5.78 mmol, 27% yield) as a liquid. LCMS: 270.0 (M+H) and 272.0 (M+2+H), Rt 2.78 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A12: (S)-5-(4,4,5,5-tetramethyl-1,3,2-dioxaborolan-2-yl)-2-((1,1,1-trifluoropropan-2-yl)oxy)pyridine To a stirred solution of (S)-5-bromo-2-((1,1,1-trifluoro-propan-2-yl)oxy)pyridine (0.5 g, 1.85 mmol) and bis(pinacolato)diboron (0.52 g, 2.04 mmol) in 1,4-dioxane (5.0 mL) was added potassium acetate (0.36 g, 3.7 mmol). Pd(dppf)$Cl_2$.DCM (0.15 g, 0.19 mmol) was added to the reaction mixture under nitrogen atmosphere and heated at 80° C. for 12 hours. The reaction mixture was cooled to room temperature, filtered through celite and concentrated under reduced pressure. The crude product was purified by column chromatography on silica gel with 10% EtOAc/PE to afford (S)-5-(4,4,5,5-tetramethyl-1,3,2-dioxaborolan-2-yl)-2-((1,1,1-trifluoropropan-2-yl)oxy)pyridine (302 mg, 0.95 mmol, 51% yield). LCMS: 318.1 (M+H), Rt 3.04 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A14: (S)-3-(chlorodifluoromethyl)-6-(6-((1,1,1-trifluoropropan-2-yl)oxy)pyridin-3-yl)-[1,2,4]triazolo[4,3-a]pyrazine To a stirred solution of (S)-5-(4,4,5,5-tetramethyl-1,3,2-dioxaborolan-2-yl)-2-((1,1,1-trifluoropropan-2-yl)oxy)pyridine (302 mg, 0.95 mmol) and 6-chloro-3-(chlorodifluoromethyl)-[1,2,4]triazolo[4,3-a]pyrazine (0.25 g, 1.04 mmol) in 1,4-dioxane (6.0 mL) was added water (1.0 mL) and $Cs_2CO_3$ (0.62 g, 1.9 mmol). Pd(dppf)$Cl_2$.DCM (0.08 g, 0.09 mmol) was added to the reaction mixture under nitrogen atmosphere and heated at 80° C. for 12 hours. The reaction mixture was cooled to room temperature, filtered through celite and concentrated under reduced pressure. The crude product was purified by column chromatography on silica gel with 20% EtOAc/PE to afford (S)-3-(chlorodifluoromethyl)-6-(6-((1,1,1-trifluoropropan-2-yl)oxy)pyridin-3-yl)-[1,2,4]triazolo[4,3-a]pyrazine (93 mg, 0.23 mmol, 24% yield). LCMS: 394.0 (M+H), Rt 2.54 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Compound 2: (S)-3-(cyclopropoxydifluoromethyl)-6-(6-((1,1,1-trifluoropropan-2-yl)oxy) pyridine-3-yl)-[1,2,4]triazolo[4,3-a]pyrazine To a stirred suspension of $Cs_2CO_3$ (463 mg, 1.42 mmol) in MeCN (6.0 mL) was added cyclopropanol (165 mg, 2.84 mmol) at room temperature and stirred for 15 min. To the reaction mixture (S)-3-(chlorodifluoromethyl)-6-(6-((1,1,1-trifluoropropan-2-yl)oxy)pyridin-3-yl)-[1,2,4]triazolo[4,3-a]pyrazine (93 mg, 0.23 mmol) in MeCN (6.0 mL) was added dropwise and stirred for 2 hours. The reaction mixture was treated with water (30 mL) and extracted with EtOAc (2×30 mL). The organic layer was washed with brine (20 mL), dried over $Na_2SO_4$ and concentrated to give a crude product. The crude product was purified by preparative HPLC to afford 2 (10 mg, 0.024 mmol, 10% yield) as a solid. Prep. HPLC method: Rt 10.42; Column: X-Bridge C8 (150×19 mm), 5.0 μm; Mobile phase: 0.1% TFA in water/acetonitrile; Flow Rate: 15.0 mL/min. HPLC: Rt 5.32 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 416.1 $(M+H)^+$, Rt 2.46 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, DMSO-$d_6$): $\delta_H$=9.71 (d, 1H), 8.91 (dd, 1H), 8.85 (d, 1H), 8.49 (dd, 1H), 7.14 (dd, 1H), 6.03-5.96 (m, 1H), 4.26-4.21 (m, 1H), 1.51 (d, 3H), 0.97-0.93 (m, 2H), 0.78-0.73 (m, 2H).

Example 3. Synthesis of Compound 3: (S)-3-(ethoxydifluoromethyl)-6-(6-((1,1,1-trifluoropropan-2-yl)oxy)pyridin-3-yl)-[1,2,4]triazolo[4,3-a]pyrazine

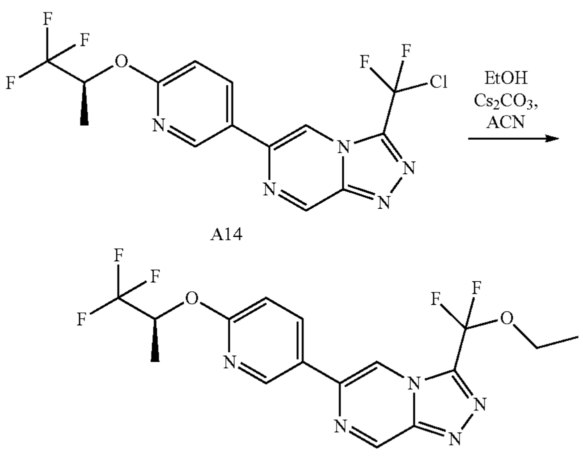

A14

3

To a stirred suspension of $Cs_2CO_3$ (463 mg, 1.42 mmol) in MeCN (6.0 mL) was added ethanol (0.17 mL, 2.84 mmol) at room temperature and stirred for 30 min. To the reaction mixture (S)-3-(chlorodifluoromethyl)-6-(6-((1,1,1-trifluoro-propan-2-yl)oxy)pyridin-3-yl)-[1,2,4]triazolo[4,3-a]pyrazine (100 mg, 0.24 mmol) in MeCN (6.0 mL) was added dropwise and stirred for 2 hours. The reaction mixture was treated with water (30 mL) and extracted with EtOAc (2×30 mL). The organic layer was washed with brine (20 mL), dried over $Na_2SO_4$ and concentrated to give a crude product. The crude product was purified by preparative HPLC to afford 3 (17 mg, 0.042 mmol, 17% yield) as a solid. Prep. HPLC method: Rt 14.3; Column: X-Bridge C8 (150×19 mm), 5.0 μm; Mobile phase: 0.1% TFA in water/acetonitrile; Flow Rate: 15.0 mL/min. HPLC: Rt 5.22 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 404.1 $(M+H)^+$, Rt 2.54 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.36 min, SFC column: Chiralcel OJ-H; mobile phase: 60:40 (A: B), A=liquid $CO_2$, B=0.5% isopropyl amine in IPA; flow rate: 3.0 mL/min; wave length: 254 nm. $^1$H NMR (400 MHz, DMSO-$d_6$): $\delta_H$=9.71 (d, 1H), 8.92 (s, 1H), 8.91 (s, 1H), 8.50 (dd, 1H), 7.14 (d, 1H), 6.02-5.98 (m, 1H), 4.32 (q, 2H), 1.51 (d, 3H), 1.39 (t, 3H).

Example 4. Synthesis of Compound 4: 6-(6-(1-cyclopropyl-2,2,2-trifluoroethoxy)pyridin-3-yl)-3-(ethoxydifluoromethyl)-[1,2,4]triazolo[4,3-a]pyrazine

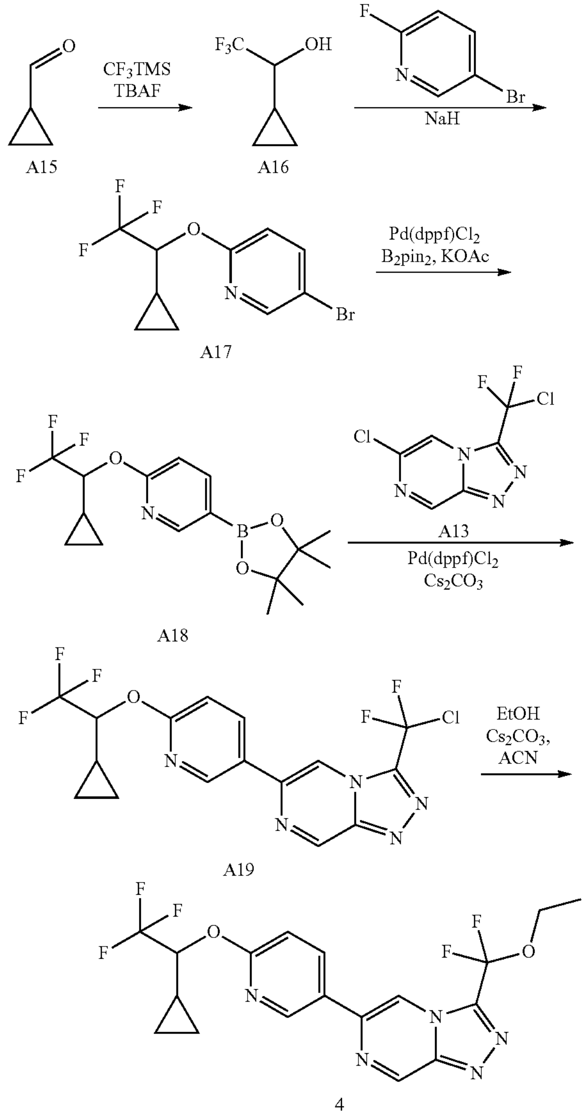

A15 A16 A17 A13 A18 A19 4

A16: 1-cyclopropyl-2,2,2-trifluoroethan-1-ol

To a stirred solution of cyclopropanecarbaldehyde (5.0 g, 71.34 mmol) in THF (50.0 mL) was added trimethyl(trifluoromethyl)silane (11.16 g, 78.47 mmol) and TBAF (1.0 M in THF, 7.14 mL, 7.1 mmol) at 0° C. The reaction mixture was slowly warmed to room temperature and stirred for 4 hours. To the reaction mixture TBAF (1.0 M in THF, 142.6 mL, 142.6 mmol) was added at room temperature and stirred for 30 min. The reaction mixture was treated with water (50.0 mL) and extracted with diethyl ether (2×100 mL). The organic layer was washed with 10% $NaHCO_3$ solution (50.0 mL) and brine (50 mL). The organic layer was dried over anhydrous $Na_2SO_4$ and concentrated at 30° C. to afford 1-cyclopropyl-2,2,2-trifluoroethan-1-ol (3.2 g), which was used for the next step without further purification.

A17: 5-bromo-2-(1-cyclopropyl-2,2,2-trifluoroethoxy)pyridine

To a stirred solution of 1-cyclopropyl-2,2,2-trifluoroethan-1-ol (3.0 g, 21.41 mmol) in THF (30.0 mL) at 0° C. was added NaH (60% in mineral oil, 1.28 g, 32.12 mmol) in small portions. The reaction mixture was stirred for 10 min and 5-bromo-2-fluoro-pyridine (3.77 g, 21.41 mmol) was added. The reaction mixture was slowly warmed to room temperature and stirred for 1 hour. The reaction mixture was cooled to 10° C. and treated with ice water (100 mL). The reaction mixture was extracted with EtOAc (2×100 mL). The organic layer was washed with brine (80 mL), dried over anhydrous $Na_2SO_4$ and concentrated to give a crude product. The crude product was purified by column chromatography on silica gel with PE to afford 5-bromo-2-(1-cyclopropyl-2,2,2-trifluoroethoxy)pyridine (3.1 g, 10.47 mmol, 48% yield). LCMS: 296.0 $(M+H)^+$ and 298.0 $(M+2+H)^+$, Rt 2.90 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A18: 2-(1-cyclopropyl-2,2,2-trifluoroethoxy)-5-(4,4,5,5-tetramethyl-1,3,2-dioxaborolan-2-yl)pyridine To a stirred solution of 5-bromo-2-(1-cyclopropyl-2,2,2-trifluoroethoxy)pyridine (3.1 g, 10.47 mmol) and bis(pinacolato)diboron (3.46 g, 13.61 mmol) in 1,4-dioxane (30 mL) was added potassium acetate (1.72 g, 20.94 mmol). Pd(dppf)$Cl_2$.DCM (0.86 g, 1.05 mmol) was added to the reaction mixture under nitrogen atmosphere and heated at 90° C. for 3 hours. The reaction mixture was cooled to room temperature and filtered through celite. The reaction mixture was treated with ice water (50 mL) and extracted with EtOAc (2×50 mL). The organic layer was washed with brine (30 mL), dried over anhydrous $Na_2SO_4$ and concentrated to give a crude product. The crude product was purified by column chromatography on silica gel with 4% EtOAc/PE to afford 2-(1-cyclopropyl-2,2,2-trifluoroethoxy)-5-(4,4,5,5-tetramethyl-1,3,2-dioxaborolan-2-yl)pyridine (3.2 g, 9.3 mmol, 89% yield). LCMS: 344.1 $(M+H)^+$, Rt 3.18 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A19: 3-(chlorodifluoromethyl)-6-(6-(1-cyclopropyl-2,2,2-trifluoroethoxy)pyridin-3-yl)-[1,2,4]triazolo[4,3-a]pyrazine To a stirred solution of 6-chloro-3-(chlorodifluoromethyl)-[1,2,4]triazolo[4,3-a]pyrazine (2.0 g, 8.37 mmol) and 2-(1-cyclopropyl-2,2,2-trifluoroethoxy)-5-(4,4,5,5-tetramethyl-1,3,2-dioxaborolan-2-yl)pyridine (3.16 g, 9.2 mmol) in 1,4-dioxane (36 mL) was added $Cs_2CO_3$ (5.45 g, 16.74 mmol) and water (4.0 mL). Pd(dppf)$Cl_2$.DCM (0.68 g, 0.84 mmol) was added to the reaction mixture under nitrogen atmosphere and heated at 90° C. for 3 hours. The reaction mixture was cooled to room temperature, filtered through celite and concentrated under reduced pressure. The crude product was purified by column chromatography on silica gel with 13% EtOAc/PE to afford 3-(chlorodifluoromethyl)-6-(6-(1-cyclopropyl-2,2,2-trifluoroethoxy)pyridin-3-yl)-[1,2,4]triazolo[4,3-a]pyrazine (1.39 g, 3.31 mmol, 39% yield). LCMS: 420.0 $(M+H)^+$, Rt 3.89 min; Column: ZORBAX Extend C18 (50×4.6 mm), 5 μm; Mobile Phase: A: 10 mM Ammonium acetate in water, B: ACN; Flow Rate: 1.2 mL/min.

Compound 4: 6-(6-(1-cyclopropyl-2,2,2-trifluoroethoxy)pyridin-3-yl)-3-(ethoxydifluoromethyl)-[1,2,4]triazolo[4,3-a]pyrazine To a stirred suspension of $Cs_2CO_3$ (1.9 g, 5.85 mmol) in MeCN (15 mL) was added ethanol (1.14 mL, 19.5 mmol) at room temperature and stirred for 15 min. To the reaction mixture 3-(chlorodifluoromethyl)-6-(6-(1-cyclopropyl-2,2,2-trifluoroethoxy)pyridin-3-yl)-[1,2,4]triazo-lo[4,3-a]pyrazine (500 mg, 0.98 mmol) in MeCN (10 mL) was added dropwise and stirred for 30 min at room temperature. The reaction mixture was treated with water (30 mL) and extracted with EtOAc (2×30 mL). The organic layer was washed with brine (20 mL), dried over $Na_2SO_4$ and concentrated to give a crude product. The crude product was purified by preparative HPLC to afford 4 (85 mg, 0.19 mmol, 20% yield) as a solid. Prep. HPLC method: Rt 11.83; Column: X-Bridge C8 (150×19 mm), 5.0 μm; Mobile phase: 0.1% TFA in water/acetonitrile; Flow Rate: 15.0 mL/min. HPLC: Rt 5.52 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 429.8 $(M+H)^+$, Rt 2.51 min; Column: X-Bridge C8 (50×4.6) mm, 3.5 μm; Mobile phase: A: 0.1% TFA in water:ACN (95:5), B: 0.1% TFA in ACN; Flow Rate: 1.5 mL/min. $^1H$ NMR (400 MHz, $CD_3OD$): $\delta_H$=9.55 (d, 1H), 8.84 (dd, 1H), 8.80 (d, 1H), 8.42 (dd, 1H), 7.04 (dd, 1H), 5.54-5.50 (m, 1H), 4.39 (q, 2H), 1.49 (t, 3H), 1.35-1.29 (m, 1H), 0.80-0.75 (m, 1H), 0.67-0.62 (m, 3H).

Example 5. Syntheses of Compound 5: (R)-6-(6-(1-cyclopropyl-2,2,2-trifluoroethoxy)pyridin-3-yl)-3-(difluoro(meth oxy)methyl)-[1,2,4]triazolo[4,3-a] pyrazine & Compound 6: (S)-6-(6-(1-cyclopropyl-2,2,2-trifluoroethoxy)pyridin-3-yl)-3-(difluoro (methoxy)methyl)-[1,2,4]triazolo[4,3-a]pyrazine. Note Stereochemistry has been Randomly Assigned

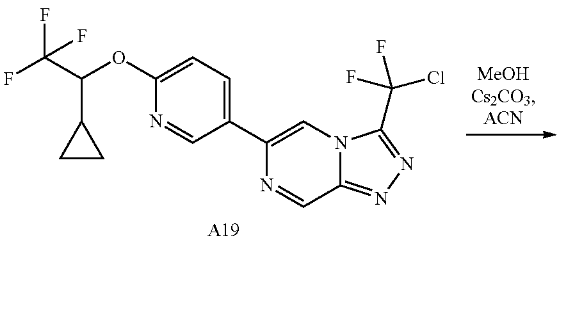

A19

-continued

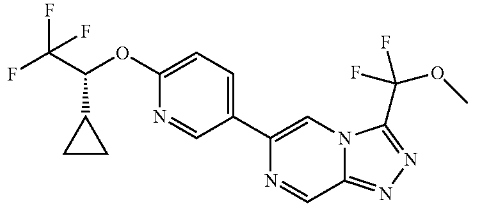

\+

5

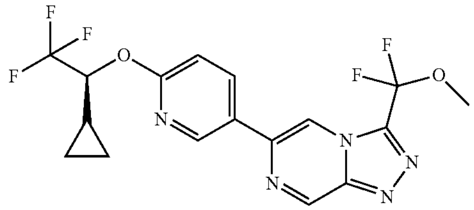

6

To a stirred suspension of $Cs_2CO_3$ (3.81 g, 11.7 mmol) in MeCN (30 mL) was added MeOH (1.58 mL, 38.99 mmol) and stirred for 10 min. To the reaction mixture 3-(chlorodifluoromethyl)-6-(6-(1-cyclopropyl-2,2,2-trifluoroethoxy) pyridin-3-yl)-[1,2,4]triazolo[4,3-a]pyrazine (1.0 g, 1.95 mmol) in MeCN (20 mL) was added. The reaction mixture was stirred for 30 min at room temperature and treated with ice water (50 mL). The reaction mixture was extracted with EtOAc (2×50 mL), washed with brine (30 mL), dried over $Na_2SO_4$ and concentrated to give a crude product. The crude product was purified by column chromatography on silica gel with 14% EtOAc/PE to afford 450 mg of the racemic compound. The racemic mixture was separated by SFC purification to afford 5 (87 mg, 0.20 mmol, 10% yield) and 6 (50 mg, 0.12 mmol, 6% yield) as solids. Chiral method: SFC column: Lux A1; mobile phase: 80:20 (A: B), A=liquid $CO_2$, B=0.5% isopropyl amine in methanol; flow rate: 3.0 mL/min; wave length: 254 nm. The stereochemistry of 5 and 6 was randomly assigned.

Compound 5: HPLC: Rt 5.25 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 416.0 $(M+H)^+$, Rt 2.47 min; Column: X-Bridge C8 (50×4.6) mm, 3.5 μm; Mobile Phase: A: 0.1% TFA in water:ACN (95:5), B: 0.1% TFA in ACN; Flow Rate: 1.5 mL/min. Chiral method: Rt 4.35 min, SFC column: Lux A1; mobile phase: 80:20 (A: B), A=liquid $CO_2$, B=0.5% isopropyl amine in methanol; flow rate: 3.0 mL/min; wave length: 254 nm. $^1H$ NMR (400 MHz, $CD_3OD$): $\delta_H$=9.55 (d, 1H), 8.85 (dd, 1H), 8.81 (d, 1H), 8.43 (dd, 1H), 7.04 (dd, 1H), 5.54-5.50 (m, 1H), 3.99 (s, 3H), 1.34-1.31 (m, 1H), 0.79-0.77 (m, 1H), 0.67-0.63 (m, 3H).

Compound 6: HPLC: Rt 5.25 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 415.9 $(M+H)^+$, Rt 2.54 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 4.85 min, SFC column: Lux A1; mobile phase: 80:20 (A: B), A=liquid $CO_2$, B=0.5% isopropyl amine in methanol; flow rate: 3.0 mL/min; wave length: 254 nm. $^1H$ NMR (400 MHz, $CD_3OD$): $\delta_H$=9.55 (d, 1H), 8.85 (dd, 1H), 8.81 (d, 1H), 8.43 (dd, 1H), 7.04 (dd, 1H), 5.54-5.50 (m, 1H), 3.99 (s, 3H), 1.34-1.31 (m, 1H), 0.79-0.76 (m, 1H), 0.67-0.66 (m, 3H).

Example 6. Synthesis of Compound 7: 3-(difluoro(methoxy)methyl)-6-(6-((1,1,1-trifluoro-3-methylbutan-2-yl)oxy)pyridin-3-yl)-[1,2,4]triazolo[4,3-a]pyrazi

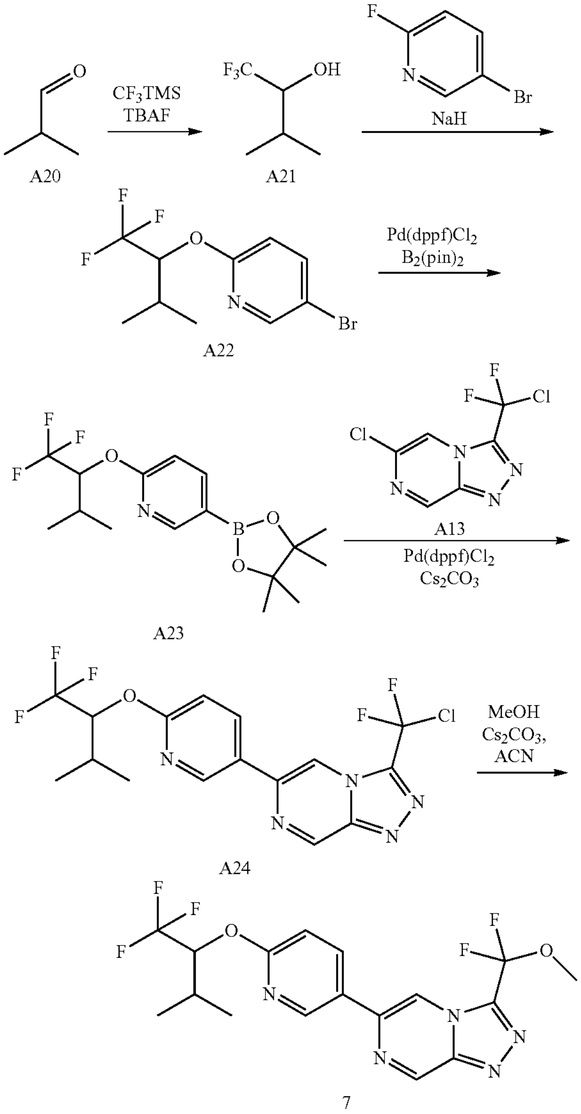

A20 A21 A22 A23 A24 7

A21: 1,1,1-trifluoro-3-methylbutan-2-ol

To a stirred solution of isobutyraldehyde (5.0 g, 69.34 mmol) in THF (50.0 mL) was added trimethyl(trifluoromethyl)silane (10.85 g, 76.27 mmol) and TBAF (1.81 g, 6.93 mmol) at 10° C. under nitrogen. The reaction mixture was stirred at room temperature for 2 hours. TBAF (36.26 g, 138.68 mmol) was added to the reaction mixture and stirred at room temperature for 2 hours. The reaction mixture was treated with water (200 mL) and extracted with diethyl ether (2×150 mL). The aqueous solution was washed with diethyl ether (100 mL). The organic layer was washed with brine (30 mL), dried over anhydrous $Na_2SO_4$ and concentrated to afford 1,1,1-trifluoro-3-methylbutan-2-ol (2.27 g, 16.0 mmol, 23% yield), which was used for the next step without further purification.

A22: 5-bromo-2-((1,1,1-trifluoro-3-methylbutan-2-yl)oxy)pyridine

To a stirred solution of 1,1,1-trifluoro-3-methylbutan-2-ol (720 mg, 5.07 mmol) in THF (15.0 mL) was added NaH (60% in mineral oil, 0.41 g, 10.13 mmol) portion wise at 0° C. and stirred for 30 min. 5-bromo-2-fluoropyridine (0.89 g, 5.07 mmol) in THF (2.0 mL) was added to the reaction mixture slowly at 0° C. The reaction mixture was slowly warmed to room temperature and stirred for 2 hours. The reaction mixture was cooled to 10° C., treated with ice water (30 mL) and extracted with EtOAc (2×30 mL). The organic layer was washed with brine (30 mL), dried over $Na_2SO_4$ and concentrated to give a crude product. The crude product was purified by column chromatography on silica gel with 15% EtOAc/PE to afford 5-bromo-2-((1,1,1-trifluoro-3-methylbutan-2-yl)oxy)pyridine (1.0 g, 3.35 mmol, 66% yield). LCMS: 297.8 $(M+H)^+$ and 299.8 $(M+2+H)^+$, Rt 3.04 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A23: 5-(4,4,5,5-tetramethyl-1,3,2-dioxaborolan-2-yl)-2-((1,1,1-trifluoro-3-methylbutan-2-yl)oxy)pyridine To a stirred solution of 5-bromo-2-((1,1,1-trifluoro-3-methylbutan-2-yl)oxy)pyridine (1.0 g, 3.35 mmol) and bis(pinacolato)diboron (1.11 g, 4.36 mmol) in 1,4-dioxane (10.0 mL) was added potassium acetate (0.66 g, 6.71 mmol). Pd(dppf)$Cl_2$.DCM (356 mg, 0.44 mmol) was added to the reaction mixture under nitrogen atmosphere and heated at 85° C. for 3 hours. The reaction mixture was cooled to room temperature, filtered through celite and concentrated under reduced pressure. The crude product was purified by column chromatography on silica gel with 15% EtOAc/PE to afford 5-(4,4,5,5-tetramethyl-1,3,2-dioxaborolan-2-yl)-2-((1,1,1-trifluoro-3-methylbutan-2-yl)oxy)pyridine (0.9 g, 2.6 mmol, 77% yield) as a solid. $^1H$ NMR (400 MHz, $CD_3OD$): $\delta_H$=8.46 (dd, 1H), 8.02 (dd, 1H), 6.88 (dd, 1H), 5.92-5.85 (m, 1H), 2.30-2.23 (m, 1H), 1.36 (s, 12H), 1.08 (d, 6H).

A24: 3-(chlorodifluoromethyl)-6-(6-((1,1,1-trifluoro-3-methylbutan-2-yl)oxy)pyridin-3-yl)-[1,2,4]triazolo[4,3-a]pyrazine To a stirred solution of 6-chloro-3-(chlorodifluoromethyl)-[1,2,4]triazolo[4,3-a]pyrazine (400 mg, 1.67 mmol) and 5-(4,4,5,5-tetramethyl-1,3,2-dioxaborolan-2-yl)-2-((1,1,1-trifluoro-3-methylbutan-2-yl)oxy)pyridine (570 mg, 1.65 mmol) in 1,4-dioxane (3.6 mL) was added $Cs_2CO_3$ (1.09 g, 3.35 mmol) and water (0.4 mL). Pd(dppf)$Cl_2$.DCM (136 mg, 0.17 mmol) was added to the reaction mixture under nitrogen atmosphere and heated at 90° C. for 3 hours. The reaction mixture was cooled to room temperature, filtered through celite and concentrated under reduced pressure. The crude product was purified by column chromatography on silica gel with 15% EtOAc/PE to afford 3-(chlorodifluoromethyl)-6-(6-((1,1,1-trifluoro-3-methylbutan-2-yl)oxy)pyridin-3-yl)-[1,2,4]triazolo[4,3-a]pyrazine (225 mg, 0.53 mmol, 31% yield). LCMS: 422.0 $(M+H)^+$, Rt 2.81 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Compound 7: 3-(difluoro(methoxy)methyl)-6-(6-((1,1,1-trifluoro-3-methylbutan-2-yl)oxy)pyridin-3-yl)-[1,2,4]triazolo[4,3-a]pyrazine To a stirred solution of MeOH (0.36 mL, 8.87 mmol) in MeCN (3.0 mL) was added $Cs_2CO_3$ (866 mg, 2.66 mmol) in a 50 mL sealed tube and the reaction mixture was stirred for 20 min. To the reaction mixture 3-(chlorodifluoromethyl)-6-(6-((1,1,1-trifluoro-3-methylbutan-2-yl)oxy)pyridin-3-yl)-[1,2,4]triazolo[4,3-a]pyrazine (185 mg, 0.44 mmol) in MeCN (15.0 mL) was added dropwise and stirred for 2 h at room temperature. The reaction mixture was treated with water (20 mL) and extracted with EtOAc (2×30 mL). The organic layer was washed with brine (20 mL), dried over $Na_2SO_4$ and concentrated to give a crude product. The crude product was purified by column chromatography on silica gel with 18% EtOAc/PE to afford racemic compound. The crude product was purified by preparative HPLC to afford 7 (60 mg, 0.14 mmol, 32% yield) as a solid. Prep. HPLC method: Rt 14.8; Column: Agilent C18 (50×50 mm), 5.0 μm; Mobile phase: 0.1% TFA in water/acetonitrile; Flow Rate: 25.0 mL/min. HPLC: Rt 5.50 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 418.1 $(M+H)^+$, Rt 2.71 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, $CD_3OD$): $\delta_H$=9.55 (d, 1H), 8.88-8.87 (m, 1H), 8.81 (d, 1H), 8.44 (dd, 1H), 7.06 (dd, 1H), 5.97-5.92 (m, 1H), 3.99 (s, 3H), 2.35-2.30 (m, 1H), 1.13-1.11 (m, 6H).

Example 7. Synthesis of Compound 8: 3-[difluoro(propoxy)methyl]-6-[6-(2,2,2-trifluoroethoxy)-3-pyridyl]-[1,2,4]triazolo[4,3-a]pyrazine

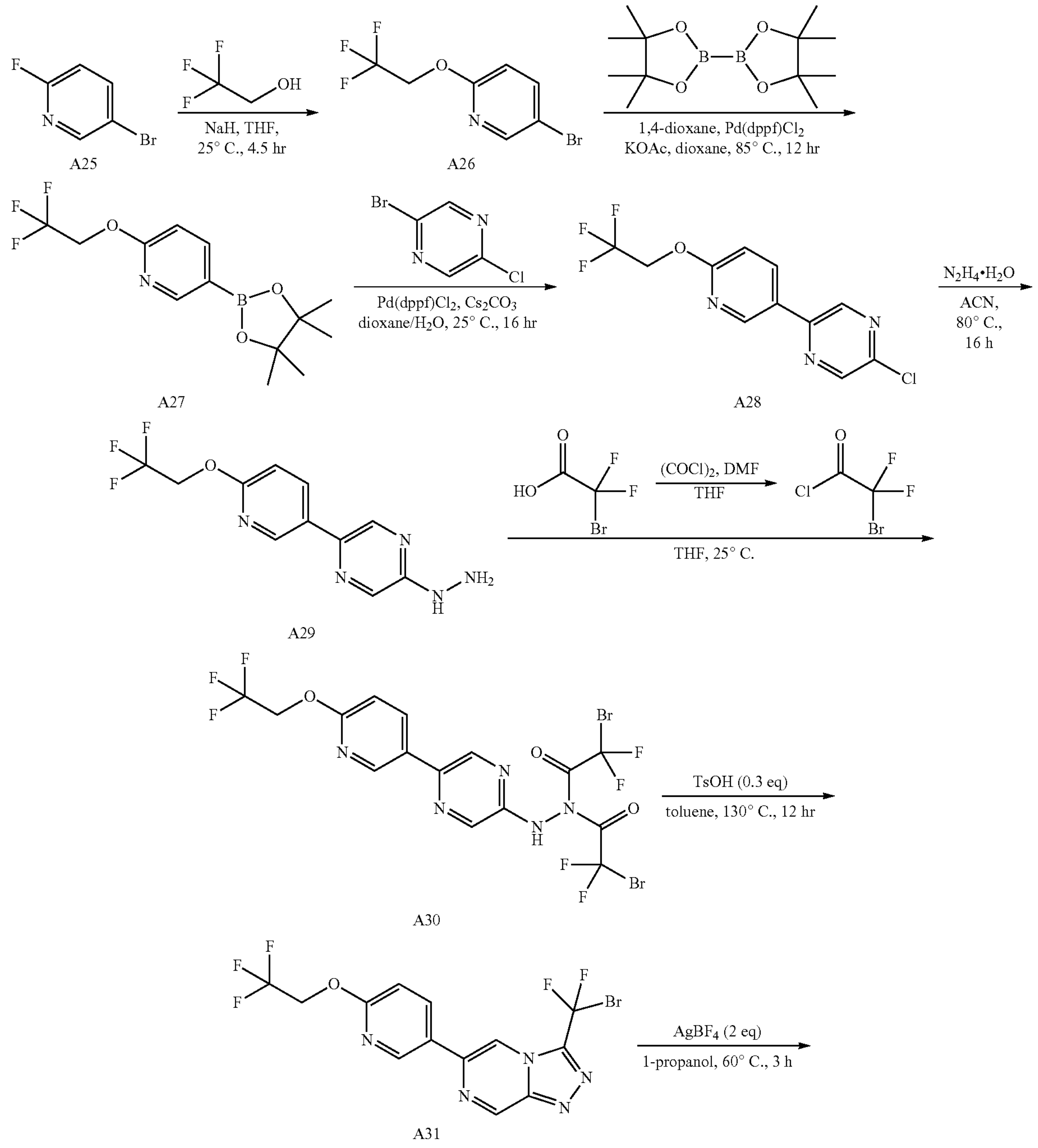

-continued

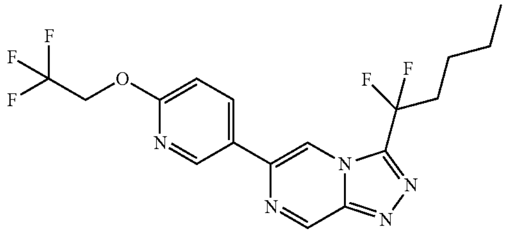

8

A26: 5-bromo-2-(2,2,2-trifluoroethoxy)pyridine

To a solution of 2,2,2-trifluoroethanol (3.13 g, 31.25 mmol) in THF (50 mL) was added NaH (1.36 g, 34.09 mmol, 60% in oil) slowly at 0° C. The mixture was stirred at 25° C. for 1 hour. To the resulting mixture was added 5-bromo-2-fluoro-pyridine (5 g, 28.41 mmol) and the mixture was stirred at 25° C. for 3.5 hours. The mixture was quenched with saturated aqueous $NH_4Cl$ (50 mL). The organic phase was separated and the aqueous layer was extracted with EtOAc (30 mL×2). The combined organic phase were washed with brine (50 mL), dried over anhydrous $Na_2SO_4$, filtered and concentrated to give the crude product (7 g, 27.34 mmol) as an oil. $^1H$ NMR (400 MHz, $CDCl_3$) $\delta_H$=8.20 (s, 1H), 7.73 (dd, 1H), 6.80 (d, 1H), 4.73 (q, 2H).

A27: 5-(4,4,5,5-tetramethyl-1,3,2-dioxaborolan-2-yl)-2-(2,2,2-trifluoroethoxy)pyridine A mixture of 5-bromo-2-(2,2,2-trifluoroethoxy)pyridine (7 g, 27.34 mmol), 4,4,5,5-tetramethyl-2-(4,4,5,5-tetramethyl-1,3,2-dioxaborolan-2-yl)-1,3,2-dioxaborolane (7.64 g, 30.08 mmol), KOAc (5.37 g, 54.68 mmol) and Pd(dppf)$Cl_2$ (1 g, 1.37 mmol) in 1,4-dioxane (80 mL) was stirred at 85° C. for 12 hours under $N_2$. After cooling to room temperature, the mixture was filtered through Celite and then the filtrate was concentrated. The crude product was purified by flash chromatography on silica gel (EtOAc in PE=0% to 5%) to give the product (8 g, 26.4 mmol, 96% yield) as an oil. $^1H$ NMR (400 MHz, $CDCl_3$) $\delta_H$=8.53 (s, 1H), 8.00 (dd, 1H), 6.84 (d, 1H), 4.80 (q, 2H), 1.35 (s, 12H).

A28: 2-chloro-5-[6-(2,2,2-trifluoroethoxy)-3-pyridyl]pyrazine

A mixture of Pd(dppf)$Cl_2$ (0.97 g, 1.32 mmol), $Cs_2CO_3$ (17.2 g, 52.79 mmol), 5-(4,4,5,5-tetramethyl-1,3,2-dioxaborolan-2-yl)-2-(2,2,2-trifluoroethoxy)pyridine (8 g, 26.39 mmol) and 2-bromo-5-chloro-pyrazine (5.62 g, 29.03 mmol) in 1,4-dioxane (80 mL) and water (8 mL) under $N_2$ was stirred at 25° C. for 16 hours. The mixture was filtered through Celite and the filtrate was concentrated. Water (150 mL) was added and the aqueous was extracted with EtOAc (150 mL×2). The combined organic phase were washed with brine (300 mL), dried over anhydrous $Na_2SO_4$, filtered and concentrated to give a crude product. The crude product was purified by flash chromatography on silica gel (EtOAc in PE=0% to 30% to 60%) to give the product (4 g, 13.55 mmol, 51% yield) as a solid. $^1H$ NMR (400 MHz, $CDCl_3$) $\delta_H$=8.78-8.73 (m, 2H), 8.64 (s, 1H), 8.29 (dd, 1H), 7.02 (d, 1H), 4.85 (q, 2H). LCMS Rt=0.92 min in 1.5 min chromatography, 5-95AB, MS ESI calcd. for $C_{11}H_8ClF_3N_3O$ $[M+H]^+$ 290.0, found 289.8.

A29: [5-[6-(2,2,2-trifluoroethoxy)-3-pyridyl]pyrazin-2-yl]hydrazine

To a solution of 2-chloro-5-[6-(2,2,2-trifluoroethoxy)-3-pyridyl]pyrazine (4 g, 13.55 mmol) in MeCN (50 mL) was added $N_2H_4.H_2O$ (6.77 g, 135.49 mmol) at 25° C. The mixture was stirred at 80° C. for 16 hours. After cooling to 25° C., the reaction was poured into water (200 mL). The mixture was filtered and the filter cake was eluted with $H_2O$ (15 mL×2). The solid was dried under reduced pressure. The solid was triturated from PE (150 mL) and EtOAc (60 mL) to give the product (2.8 g, 9.81 mmol, 72% yield) as a solid. $^1H$ NMR (400 MHz, DMSO-$d_6$) $\delta_H$=8.74 (s, 1H), 8.58 (s, 1H), 8.31 (dd, 1H), 8.24-8.10 (m, 2H), 7.05 (d, 1H), 5.03 (q, 2H), 4.34 (s, 2H). LCMS Rt=0.70 min in 1.5 min chromatography, 5-95AB, MS ESI calcd. for $C_{11}H_{11}F_3N_5O$ $[M+H]^+$ 286.1, found 285.8.

A30: 2-bromo-N-(2-bromo-2,2-difluoro-acetyl)-2,2-difluoro-N'-[5-[6-(2,2,2-trifluoroethoxy)-3-pyridyl]pyrazin-2-yl]acetohydrazide To a solution of 2-bromo-2,2-difluoro-acetic acid (1 g, 5.72 mmol) in THF (10 mL) was added DMF (20.89 mg, 0.29 mmol) and $(COCl)_2$ (0.58 mL, 6.86 mmol). The resulting mixture was stirred at 25° C. for 30 min. A solution of [5-[6-(2,2,2-trifluoroethoxy)-3-pyridyl]pyrazin-2-yl]hydrazine (1 g, 3.51 mmol) in THF (10 mL) was added to the mixture. The mixture was stirred at 25° C. for 1 hour. Water (20 mL) was added and the aqueous layer was extracted with EtOAc (20 mL×2). The combined organic layers were washed with brine (30 mL), dried over anhydrous $Na_2SO_4$, filtered and concentrated to afford the product (1.7 g, 2.84 mmol, 80% yield) as an oil. LCMS Rt=1.49 min in 2.0 min chromatography, 10-80AB, MS ESI calcd. for $C_{16}H_9Br_2F_7N_5O_3[M+H]^+$ 599.9, found 600.1.

A31: 3-[bromo(difluoro)methyl]-6-[6-(2,2,2-trifluoroethoxy)-3-pyridyl]-[1,2,4]triazolo[4,3-a]pyrazine To a solution of 2-bromo-N-(2-bromo-2,2-difluoro-acetyl)-2,2-difluoro-N'-[5-[6-(2,2,2-trifluoroethoxy)-3-pyridyl]pyrazin-2-yl]acetohydrazide (1.7 g, 2.84 mmol) in toluene (20 mL) was added TsOH (146.6 mg, 0.85 mmol). The mixture was stirred at 130° C. for 12 hours. Water (30 mL) was added and the aqueous layer was extracted with EtOAc (30 mL×2). The combined organic layers were washed with brine (30 mL), dried over anhydrous $Na_2SO_4$, filtered and concentrated to give a crude product. The crude product was purified by flash chromatography on silica gel (EtOAc in PE 0~20%) to afford the product (700 mg, 1.65 mmol, 58% yield) as a solid. $^1H$ NMR (400 MHz, $CDCl_3$) $\delta_H$=9.59 (s, 1H), 8.78 (s, 1H), 8.42 (s, 1H), 8.27 (dd, 1H), 7.06 (d, 1H), 4.87 (q, 2H). LCMS Rt=0.89 min in 1.5 min chromatography, 5-95AB, MS ESI calcd. for $C_{13}H_8BrF_5N_5O$ $[M+H]^+$ 426.0 found 425.7.

Compound 8: 3-[difluoro(propoxy)methyl]-6-[6-(2,2,2-trifluoroethoxy)-3-pyridyl]-[1,2,4]triazolo[4,3-a]pyrazine To a solution of 3-[bromo(difluoro)methyl]-6-[6-(2,2,2-trifluoroethoxy)-3-pyridyl]-[1,2,4]triazolo[4,3-a]pyrazine (150 mg, 0.35 mmol) in 1-propanol (2 mL) was added $AgBF_4$ (137.23 mg, 0.71 mmol). The mixture was stirred at 60° C. for 3 hours. Brine (30 mL) was added and the aqueous layer was filtered through Celite and the filtered cake was eluted with EtOAc (10 mL×2). The filtrate was separated and the aqueous phase was extracted with EtOAc (20 mL×2). The combined organic layers were washed with brine (50 mL), dried over anhydrous $Na_2SO_4$, filtered and concentrated to give a crude product. The crude product was purified by flash chromatography (EtOAc in PE 0~20%) to afford the product (80.95 mg, 0.20 mmol, 56% yield) as a solid. $^1H$ NMR (400 MHz, $CDCl_3$) $\delta_H$=9.53 (s, 1H), 8.72 (s 1H), 8.47 (d, 1H), 8.24 (dd, 1H), 7.05 (d, 1H), 4.86 (q, 2H), 4.25 (t, 2H), 1.94-1.83 (m, 2H), 1.09 (t, 3H). LCMS Rt=1.23 min in 2.0 min chromatography, 10-80AB, MS ESI calcd. for $C_{16}H_{15}F_5N_5O_2[M+H]^+$ 404.1, found 404.1.

Example 8. Syntheses of Compound 9: (R)-3-(difluoro(methoxy)methyl)-6-(6-((1,1-difluoropropan-2-yl)oxy)pyridin-3-yl)-[1,2,4]triazolo[4,3-a]pyrazine & Compound 10: (S)-3-(difluoro(methoxy)methyl)-6-(6-((1,1-difluoropropan-2-yl)oxy)pyridin-3-yl)-[1,2,4]triazolo[4,3-a]pyrazine. Note Stereochemistry was Randomly Assigned

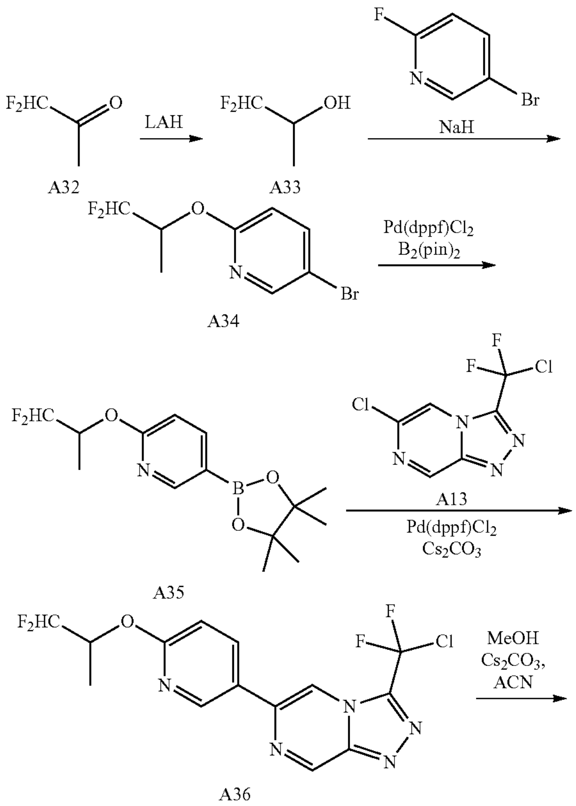

-continued

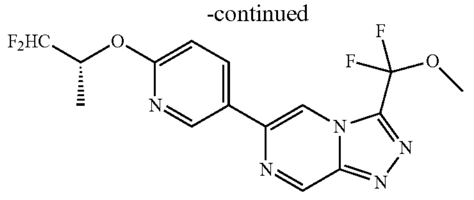

+

9

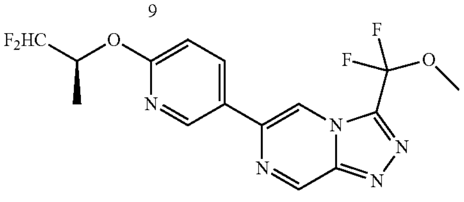

10

A33: 1,1-difluoropropan-2-ol

To a stirred solution of 1,1-difluoropropan-2-one (2.0 g, 21.26 mmol) in THF (20.0 mL) was added LAH (1.0 M in THF, 32.0 mL, 31.89 mmol) at 0° C. The reaction mixture was slowly warmed to room temperature and stirred for 2 hours. The reaction mixture was treated with saturated aqueous $Na_2SO_4$ solution (5 mL) at 0° C. and stirred for 30 min. The reaction mixture was filtered through celite, the filtrate was dried over $Na_2SO_4$ and used for the next step as a solution in THF.

A34: 5-bromo-2-((1,1-difluoropropan-2-yl)oxy)pyridine

To a stirred solution of 1,1-difluoropropan-2-ol (21.2 mmol) in THF was added NaH (60% in mineral oil, 1.25 g, 31.2 mmol) portion wise at 0° C. and stirred for 15 min. 5-bromo-2-fluoro-pyridine (3.66 g, 20.82 mmol) was added to the reaction mixture slowly at 0° C. The reaction mixture was slowly warmed to room temperature and stirred for 1 hour. The reaction mixture was cooled to 10° C., treated with ice water (30 mL) and extracted with EtOAc (2×50 mL). The organic layer was washed with brine (40 mL), dried over $Na_2SO_4$ and concentrated to give a crude product. The crude product was purified by column chromatography on silica gel with 2% EtOAc/PE to afford 5-bromo-2-((1,1-difluoropropan-2-yl)oxy)pyridine (1.01 g, 4.03 mmol, 19% yield). LCMS: 252.0 $(M+H)^+$ and 254.0 $(M+2+H)^+$, Rt 2.44 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A35: 2-((1,1-difluoropropan-2-yl)oxy)-5-(4,4,5,5-tetramethyl-1,3,2-dioxaborolan-2-yl)pyridine To a stirred solution of 5-bromo-2-((1,1-difluoropropan-2-yl)oxy)pyridine (1.01 g, 4.03 mmol) and bis(pinacolato) diboron (1.33 g, 5.24 mmol) in 1,4-dioxane (22.0 mL) was added potassium acetate (0.79 g, 8.06 mmol). Pd(dppf) $Cl_2$.DCM (0.33 g, 0.40 mmol) was added to the reaction mixture under nitrogen atmosphere and heated at 85° C. for 3 hours. The reaction mixture was cooled to room temperature, filtered through celite and concentrated under reduced pressure. The crude product was purified by column chromatography on silica gel with 4% EtOAc/PE to afford 2-((1,1-difluoropropan-2-yl)oxy)-5-(4,4,5,5-tetramethyl-1,3,2-dioxaborolan-2-yl)pyridine (1.0 g, 3.34 mmol, 82% yield). LCMS: 300.1 $(M+H)^+$, Rt 2.84 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A36: 3-(chlorodifluoromethyl)-6-(6-((1,1-difluoropropan-2-yl)oxy)pyridin-3-yl)-[1,2,4]triazolo[4,3-a]pyrazine To a stirred solution of 2-((1,1-difluoropropan-2-yl)oxy)-5-(4,4,5,5-tetramethyl-1,3,2-dioxaborolan-2-yl)pyridine (1.0 g, 3.34 mmol) and 6-chloro-3-(chlorodifluoromethyl)-[1,2,4]triazolo[4,3-a]pyrazine (0.88 g, 3.68 mmol) in 1,4-dioxane (9.0 mL) was added $Cs_2CO_3$ (2.18 g, 6.69 mmol) and water (1.0 mL). $Pd(dppf)Cl_2$.DCM (0.27 g, 0.33 mmol) was added to the reaction mixture under nitrogen atmosphere and heated at 90° C. for 3 hours. The reaction mixture was cooled to room temperature, filtered through celite and concentrated under reduced pressure. The crude product was purified by column chromatography on silica gel with 12% EtOAc/PE to afford 3-(chlorodifluoromethyl)-6-(6-((1,1-difluoropropan-2-yl)oxy)pyridin-3-yl)-[1,2,4]triazolo[4,3-a]pyrazine (252 mg, 0.67 mmol, 20% yield). LCMS: 375.8 $(M+H)^+$, Rt 2.34 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Compounds 9 & 10: (R)-3-(difluoro(methoxy)methyl)-6-(6-((1,1-difluoropropan-2-yl)oxy)pyridin-3-yl)-[1,2,4]triazolo[4,3-a]pyrazine & (S)-3-(difluoro(methoxy)methyl)-6-(6-((1,1-difluoropropan-2-yl)oxy)pyridin-3-yl)-[1,2,4]triazolo[4,3-a]pyrazine To a stirred suspension of $Cs_2CO_3$ (1.01 g, 3.11 mmol) in MeCN (5.0 mL) in a sealed tube (50 mL) was added MeOH (0.42 mL, 10.36 mmol) at room temperature and stirred for 10 min. To the reaction mixture 3-(chlorodifluoromethyl)-6-(6-((1,1-difluoropropan-2-yl)oxy)pyridin-3-yl)-[1,2,4]triazolo[4,3-a]pyrazine (195 mg, 0.52 mmol) in MeCN (5.0 mL) was added dropwise and stirred for 30 min. The reaction mixture was treated with water (20 mL) and extracted with EtOAc (2×30 mL). The organic layer was washed with brine (20 mL), dried over $Na_2SO_4$ and concentrated to give a crude product. The crude product was purified by column chromatography on silica gel with 18% EtOAc/PE to afford the racemic compound. The racemic mixture was separated by SFC purification to afford 9 (33 mg, 0.089 mmol, 17% yield) and 10 (31 mg, 0.083 mmol, 16% yield) as solids. Chiral method: SFC column: Lux C3; mobile phase: 90:10 (A: B), A=liquid $CO_2$, B=0.5% isopropyl amine in methanol; flow rate: 3.0 mL/min; wave length: 254 nm. The stereochemistry of 9 and 10 was randomly assigned.

Compound 9: HPLC: Rt 4.48 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 372.1 $(M+H)^+$, Rt 2.15 min; Column: X-Bridge C8 (50×4.6) mm, 3.5 μm; Mobile Phase: A: 0.1% TFA in water:ACN (95:5), B: 0.1% TFA in ACN; Flow Rate: 1.5 mL/min. Chiral method: Rt 5.5 min, SFC column: Lux C3; mobile phase: 90:10 (A: B), A=liquid $CO_2$, B=0.5% isopropyl amine in methanol; flow rate: 3.0 mL/min; wave length: 254 nm. $^1H$ NMR (400 MHz, $CD_3OD$): $\delta_H$=9.54 (d, 1H), 8.87 (d, 1H), 8.79 (d, 1H), 8.39 (dd, 1H), 6.99-6.97 (m, 1H), 6.21-5.93 (m, 1H), 5.58-5.50 (m, 1H), 3.99 (s, 3H), 1.44 (d, 3H).

Compound 10: HPLC: Rt 4.48 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 372.1 $(M+H)^+$, Rt 2.15 min; Column: X-Bridge C8 (50×4.6) mm, 3.5 μm; Mobile Phase: A: 0.1% TFA in water:ACN (95:5), B: 0.1% TFA in ACN; Flow Rate: 1.5 mL/min. Chiral method: Rt 6.2 min, SFC column: Lux C3; mobile phase: 90:10 (A: B), A=liquid $CO_2$, B=0.5% isopropyl amine in methanol; flow rate: 3.0 mL/min; wave length: 254 nm. $^1H$ NMR (400 MHz, $CD_3OD$): $\delta_H$=9.54 (d, 1H), 8.88 (d, 1H), 8.79 (d, 1H), 8.40 (dd, 1H), 7.00-6.98 (m, 1H), 6.21-5.93 (m, 1H), 5.58-5.51 (m, 1H), 3.99 (s, 3H), 1.44 (d, 3H).

Example 9. Synthesis of Compound 11: 3-[difluoro(isopropoxy)methyl]-6-[6-(2,2,2-trifluoroethoxy)-3-pyridyl]-[1,2,4]triazolo[4,3-a]pyrazine

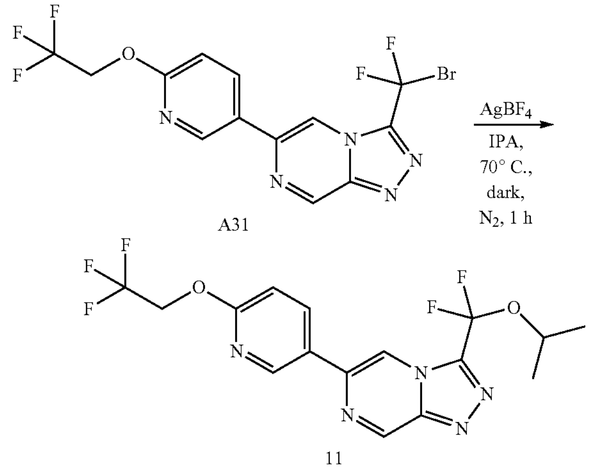

To a mixture of 3-[bromo(difluoro)methyl]-6-[6-(2,2,2-trifluoroethoxy)-3-pyridyl]-[1,2,4]triazolo[4,3-a]pyrazine (940.0 mg, 1.88 mmol) and $Na_2CO_3$ (599.02 mg, 5.65 mmol) in IPA (10 mL) was added $AgBF_4$ (1.1 g, 5.65 mmol). The mixture was stirred at 70° C. under $N_2$ and dark for 1 hour. After cooling to room temperature, the mixture was poured into the brine (20 mL). Then the mixture was filtered and the filtrate was diluted with $H_2O$ (10 mL). The mixture was extracted with EtOAc (10 mL×2). The combined organic phase was washed with water (10 mL) and brine (10 mL), dried over anhydrous $Na_2SO_4$, filtered and concentrated under reduced pressure. The crude product was purified by flash chromatography on silica gel (EtOAc in PE=0 to 0%) to afford the crude product (500 mg, 1.24 mmol) as a solid. Then the crude product was re-dissolved in n-hexane (10 mL) and DCM (10 mL). The resulting solution was stirred at 60° C. under 15 psi for 30 minutes to remove most of DCM. After cooling to room temperature, the mixture was filtered and the filter cake was washed with n-hexane (5 mL×3), dried to give the product (282.75 mg, 0.70 mmol, 57% yield) as a solid. $^1H$ NMR (400 MHz, $CDCl_3$) $\delta_H$=9.52 (s, 1H), 8.71 (d, 1H), 8.46 (d, 1H), 8.24 (dd, 1H), 7.05 (d, 1H), 5.08-4.98 (m, 1H), 4.85 (q, 2H), 1.51 (d, 6H). LCMS Rt=1.21 min in 2.0 min chromatography, 10-80AB, MS ESI calcd. for $C_{16}H_{15}F_5N_5O_2[M+H]^+$ 404.1, found 404.0.

Example 10. Synthesis of Compound 12: 3-(difluoro(methoxy)methyl)-6-(6-(2,2,3,3-tetrafluorocyclobutoxy)pyridin-3-yl)-[1,2,4]triazolo[4,3-a]pyrazine

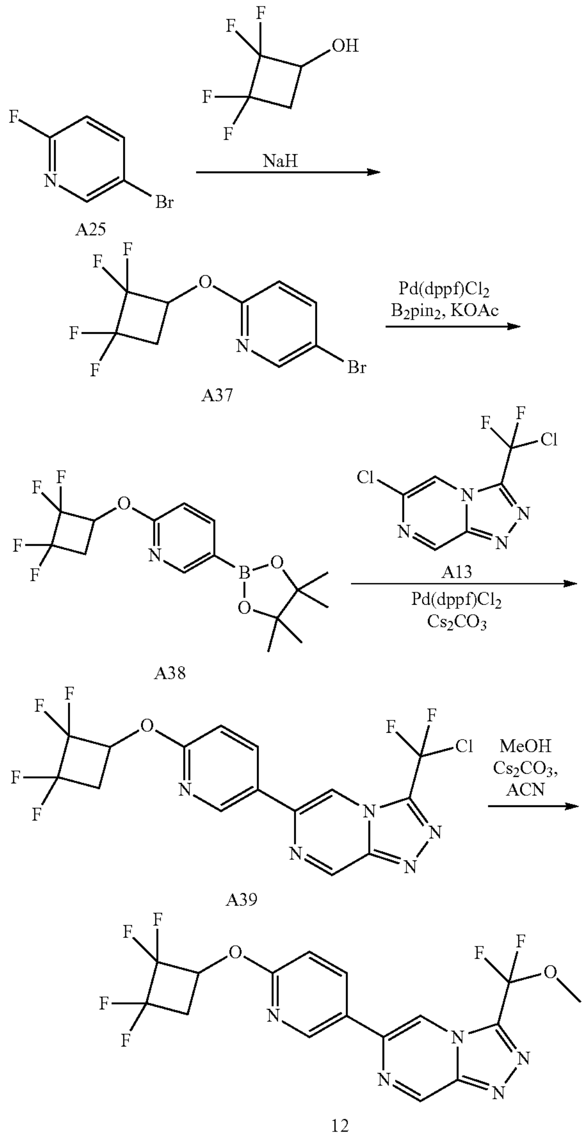

A37: 5-bromo-2-(2,2,3,3-tetrafluorocyclobutoxy)pyridine

To a stirred solution of 2,2,3,3-tetrafluorocyclobutanol (1.0 g, 6.94 mmol) in THF (20 mL) at 0° C. was added NaH (60% in mineral oil, 305 mg, 7.64 mmol) in small portions. The reaction mixture was slowly warmed to room temperature and stirred for 15 min. 5-bromo-2-fluoro-pyridine (1.22 g, 6.94 mmol) was added dropwise to the reaction mixture and stirred for 2 hours. The reaction mixture was cooled to 10° C. and treated with ice water (50 mL). The reaction mixture was extracted with EtOAc (2×60 mL). The organic layer was washed with brine (50 mL), dried over anhydrous $Na_2SO_4$ and concentrated to give a crude product. The crude product was purified by column chromatography on silica gel with 5% EtOAc/PE to afford 5-bromo-2-(2,2,3,3-tetrafluorocyclobutoxy)pyridine (900 mg, 2.99 mmol, 43% yield). LCMS: 300.0 $(M+H)^+$ and 302.0 $(M+2+H)^+$, Rt 2.65 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A38: 2-(2,2,3,3-tetrafluorocyclobutoxy)-5-(4,4,5,5-tetramethyl-1,3,2-dioxaborolan-2-yl)pyridine To a stirred solution of 5-bromo-2-(2,2,3,3-tetrafluorocyclobutoxy)pyridine (0.9 g, 3.0 mmol) and bis(pinacolato) diboron (0.84 g, 3.3 mmol) in 1,4-dioxane (15.0 mL) was added potassium acetate (0.59 g, 6.0 mmol). Pd(dppf) $Cl_2$.DCM (0.24 g, 0.30 mmol) was added to the reaction mixture under nitrogen atmosphere and heated at 80° C. for 12 hours. The reaction mixture was cooled to room temperature, filtered through celite and concentrated under reduced pressure. The crude product was purified by column chromatography on silica gel with 10% EtOAc/PE to afford 2-(2,2,3,3-tetrafluorocyclobutoxy)-5-(4,4,5,5-tetramethyl-1,3,2-dioxaborolan-2-yl)pyridine (765 mg, 2.2 mmol, 73% yield). LCMS: 348.1 $(M+H)^+$, Rt 2.92 min Column: ZORBAX XDB C-18 (50×4.6 mm), 3.5 μm; Mobile Phase: A: 0.1% HCOOH in water:ACN (95:5), B: ACN; Flow Rate: 1.5 mL/min.

A39: 3-(chlorodifluoromethyl)-6-(6-(2,2,3,3-tetrafluorocyclobutoxy)pyridin-3-yl)-[1,2,4]triazolo[4,3-a]pyrazine To a stirred solution of 2-(2,2,3,3-tetrafluorocyclobutoxy)-5-(4,4,5,5-tetramethyl-1,3,2-dioxaborolan-2-yl)pyridine (0.9 g, 2.59 mmol) and 6-chloro-3-(chlorodifluoromethyl)-[1,2,4]triazolo[4,3-a]pyrazine (0.68 g, 2.85 mmol) in 1,4-dioxane (6.0 mL) was added water (1.0 mL) and $Cs_2CO_3$ (1.69 g, 5.19 mmol). Pd(dppf)$Cl_2$.DCM (0.21 g, 0.26 mmol) was added to the reaction mixture under nitrogen atmosphere and heated at 80° C. for 12 hours. The reaction mixture was cooled to room temperature, filtered through celite and concentrated under reduced pressure. The crude product was purified by column chromatography on silica gel with 40% EtOAc/PE to afford 3-(chlorodifluoromethyl)-6-(6-(2,2,3,3-tetrafluorocyclobutoxy)pyridin-3-yl)-[1,2,4]triazolo[4,3-a]pyrazine (233 mg, 0.55 mmol, 21% yield). LCMS: 423.8 $(M+H)^+$, Rt 2.43 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Compound 12: 3-(difluoro(methoxy)methyl)-6-(6-(2,2,3,3-tetrafluorocyclobutoxy)pyridin-3-yl)-[1,2,4]triazolo[4,3-a]pyrazine To a stirred suspension of $Cs_2CO_3$ (463 mg, 1.42 mmol) in MeCN (3.0 mL) was added MeOH (0.12 mL, 2.84 mmol) at room temperature and stirred for 30 min. To the reaction mixture 3-(chlorodifluoromethyl)-6-(6-(2,2,3,3-tetrafluorocyclobutoxy)pyridin-3-yl)-[1,2,4]triazolo[4,3-a]pyrazine (100 mg, 0.24 mmol) in MeCN (3.0 mL) was added dropwise and stirred for 2 hours. The reaction mixture was treated with water (30 mL) and extracted with EtOAc (2×30 mL). The organic layer was washed with brine (20 mL), dried over $Na_2SO_4$ and concentrated to give a crude product.

The crude product was purified by preparative HPLC to afford 12 (25 mg, 0.06 mmol, 24% yield) as a solid. Prep. HPLC method: Rt 12.62; Column: X-Bridge C18 (150×19 mm), 5.0 μm; Mobile phase: 0.1% TFA in water/acetonitrile; Flow Rate: 15.0 mL/min. HPLC: Rt 4.88 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 420.1 $(M+H)^+$, Rt 2.38 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, DMSO-$d_6$): $\delta_H$=9.71 (d, 1H), 8.98-8.96 (m, 2H), 8.53 (dd, 1H), 7.19 (dd, 1H), 5.74-5.69 (m, 1H), 3.93 (s, 3H), 3.02-2.88 (m, 1H), 2.61-2.48 (m, 1H).

Example 11. Syntheses of Compound 13: 3-[difluoro(methoxy)methyl]-6-[6-[(1R)-1-(trifluoromethyl)propoxy]-3-pyridyl]-[1,2,4]triazolo[4,3-a]pyrazine & Compound 14: 3-[difluoro(methoxy)methyl]-6-[6-[(1S)-1-(trifluoromethyl)propoxy]-3-pyridyl]-[1,2,4]triazolo[4,3-a]pyrazine

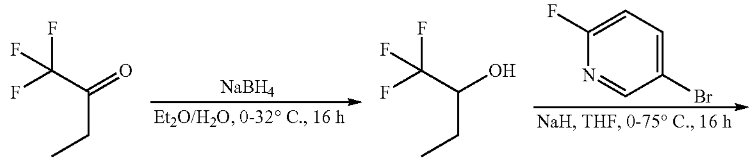

A40 A41

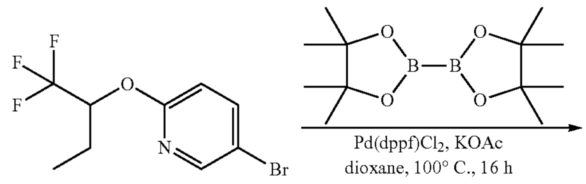

A42

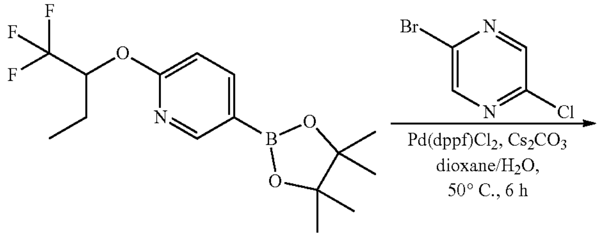

A43

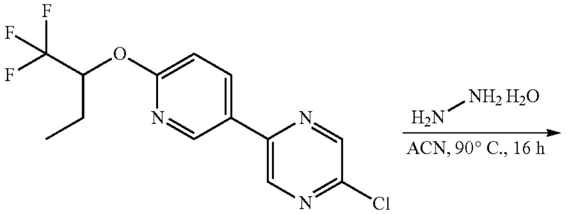

A44

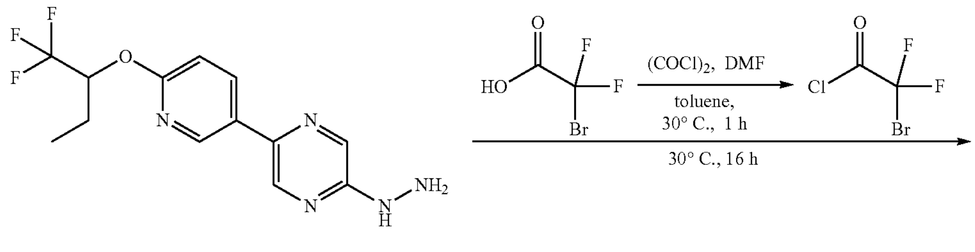

A45

-continued

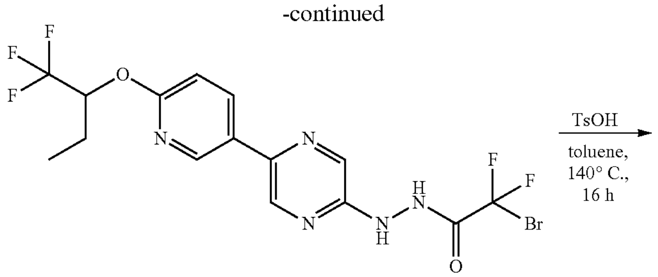

A46

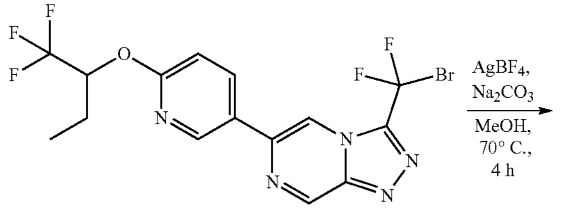

A47

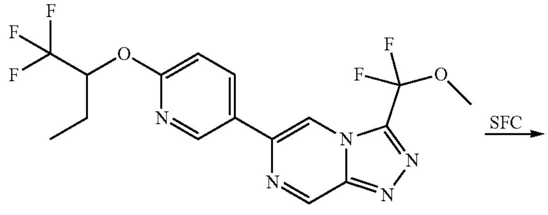

A48

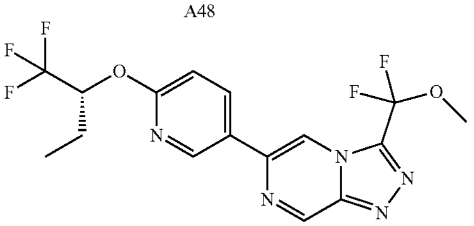
+

13

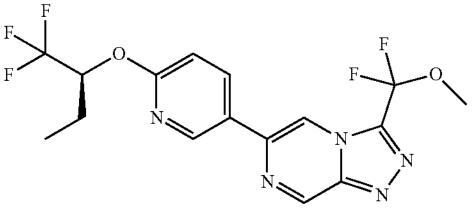

14

A41: 1,1,1-trifluorobutan-2-ol

To a solution of 1,1,1-trifluorobutan-2-one (30 g, 237.94 mmol) in ether (300 mL) and water (10 mL) was added a solution of $NaBH_4$ (9.0 g, 237.94 mmol) in water (40 mL) in portions at 0 TC. The mixture was stirred at 32° C. for 16 hours. 0.5 M HCl was added to acidify to pH 6. The aqueous layer was extracted with EtOAc (100 mL×3). The combined organic layers were washed with brine (100 mL), dried over anhydrous $Na_2SO_4$, filtered and concentrated under reduced pressure. The crude product was distilled under reduced pressure (water pump, bp 75-80° C.) to afford the product (12 g, 67.45 mmol, 28% yield) as an oil. 1H NMR (400 MHz, $CDCl_3$) $\delta_H$=3.90-3.78 (m, 1H), 2.80-2.60 (m, 1H), 1.83-1.70 (m, 1H), 1.60-1.55 (m, 1H), 1.07 (t, 3H).

A42: 5-bromo-2-[1-(trifluoromethyl)propoxy]pyridine

To a solution of 1,1,1-trifluorobutan-2-ol (4 g, 22.48 mmol) in THF (50 mL) was added NaH (0.99 g, 24.73 mmol, 60% in oil) in portions at 0° C. The mixture was stirred at 0° C. for 30 min. Then 5-bromo-2-fluoro-pyridine (4.35 g, 24.73 mmol) was added dropwise to the above mixture. The mixture was stirred at 75° C. for 16 hours. Water (50 mL) was added and the aqueous layer was extracted with EtOAc (50 mL×3). The combined organic layers were washed with brine (50 mL), dried over anhydrous $Na_2SO_4$, filtered and concentrated to give a crude product. The crude product was purified by flash chromatography on silica gel (EtOAc in PE 0 to 2%) to afford the product (6.3 g, 22.18 mmol, 99% yield) as an oil. $^1H$ NMR (400 MHz, $CDCl_3$) $\delta_H$=8.18 (d, 1H), 7.75-7.67 (m, 1H), 6.76 (d, 1H), 5.80-5.67 (m, 1H), 2.00-1.80 (m, 2H), 1.01 (t, 3H).

A43: 5-(4,4,5,5-tetramethyl-1,3,2-dioxaborolan-2-yl)-2-[1-(trifluoromethyl)propoxy]pyridine To a solution of 5-bromo-2-[1-(trifluoromethyl)propoxy]pyridine (6.3 g, 22.18 mmol) in 1,4-dioxane (70 mL) were added 4,4,5,5-tetramethyl-2-(4,4,5,5-tetramethyl-1,3,2-dioxaborolan-2-yl)-1,3,2-dioxaborolane (6.19 g, 24.4 mmol) and KOAc (4.35 g, 44.36 mmol). Then Pd(dppf)$Cl_2$ (811 mg, 1.11 mmol) was added to the above mixture under $N_2$. The resulting mixture was stirred at 100° C. for 16 hours. The mixture was filtered and the filtrate was concentrated under reduced pressure. Water (100 mL) was added and the aqueous layer was extracted with EtOAc (100 mL×3). The combined organic layers were washed with brine (100 mL), dried over anhydrous $Na_2SO_4$, filtered and concentrated to give a crude product. The crude product was purified by flash chromatography on silica gel (PE) to afford the product (7.1 g, 21.44 mmol, 97% yield) as an oil. $^1$H NMR (400 MHz, $CDCl_3$) $\delta_H$=8.50 (d, 1H), 7.98 (dd, 1H), 6.80 (d, 1H), 5.97-5.86 (m, 1H), 2.00-1.80 (m, 2H), 1.35 (s, 12H), 1.00 (t, 3H).

A44: 2-chloro-5-[6-[1-(trifluoromethyl)propoxy]-3-pyridyl]pyrazine

To a solution of 5-(4,4,5,5-tetramethyl-1,3,2-dioxaborolan-2-yl)-2-[1-(trifluoromethyl)propoxy]pyridine (6.3 g, 19.03 mmol) in 1,4-dioxane (100 mL) and water (10 mL) were added 2-bromo-5-chloro-pyrazine (4.05 g, 20.93 mmol) and $Cs_2CO_3$ (9.3 g, 28.54 mmol). The mixture was stirred at 50° C. for 6 hours. The mixture was filtered and the filtrate was concentrated. Water (50 mL) was added and the aqueous layer was extracted with EtOAc (50 mL×3). The combined organic layer was washed with brine (50 mL), dried over anhydrous $Na_2SO_4$, filtered and concentrated to give a crude product. The crude product was purified by flash chromatography on silica gel (EtOAc in PE 0 to 10%) to afford the product (4.2 g, 13.22 mmol, 69% yield) as a solid. $^1$H NMR (400 MHz, $CDCl_3$) $\delta_H$=8.80-8.73 (m, 2H), 8.63 (s, 1H), 8.27 (dd, 1H), 6.98 (d, 1H), 5.95-5.85 (m, 1H), 2.06-1.87 (m, 2H), 1.05 (t, 3H).

A45: [5-[6-[1-(trifluoromethyl)propoxy]-3-pyridyl]pyrazin-2-yl]hydrazine

To a solution of 2-chloro-5-[6-[1-(trifluoromethyl)propoxy]-3-pyridyl]pyrazine (4.2 g, 13.22 mmol) in MeCN (40 mL) was added hydrazine hydrate (6.62 g, 132.2 mmol). The mixture was stirred at 90° C. for 16 hours. Water (10 mL) was added and the aqueous layer was extracted with EtOAc (100 mL×3). The combined organic layers were washed with brine (100 mL), dried over anhydrous $Na_2SO_4$, filtered and concentrated to give the crude product. The crude product was purified by flash chromatography on silica gel (EtOAc in PE 0 to 50%) to afford the product (3.1 g, 9.90 mmol, 75% yield) as a solid. $^1$H NMR (400 MHz, DMSO-$d_6$) $\delta_H$=8.70 (d, 1H), 8.57 (s, 1H), 8.29 (dd, 1H), 8.19 (s, 1H), 8.13 (s, 1H), 7.02 (d, 1H), 5.97-5.86 (m, 1H), 4.34 (brs, 2H), 2.00-1.77 (m, 2H), 0.96 (t, 3H).

A47: 3-[bromo(difluoro)methyl]-6-[6-[1-(trifluoromethyl)propoxy]-3-pyridyl]-[1,2,4]triazolo[4,3-a]pyrazine To a solution of 2-bromo-2,2-difluoro-acetic acid (838 mg, 4.79 mmol) in toluene (10 mL) were added $(COCl)_2$ (0.49 mL, 5.75 mmol) and 1 drop of DMF. The mixture was stirred at 30° C. for 1 hour. [5-[6-[1-(trifluoromethyl)propoxy]-3-pyridyl]pyrazin-2-yl]hydrazine (1.0 g, 3.19 mmol) was added to the above mixture. The mixture was stirred at 30° C. for 16 hours. TsOH (165 mg, 0.96 mmol) was added to the above mixture and the mixture was stirred at 140° C. for 16 hours. Water (50 mL) was added and the aqueous layer was extracted with EtOAc (50 mL×3). The combined organic layers were washed with brine (50 mL), dried over anhydrous $Na_2SO_4$, filtered and concentrated to give a crude product. The crude product was purified by flash chromatography on silica gel to afford the product (1.1 g, 2.43 mmol, 76% yield) as a solid. $^1$H NMR (400 MHz, $CDCl_3$) $\delta_H$=9.61 (d, 1H), 8.75 (d, 1H), 8.42 (s, 1H), 8.26 (dd, 1H), 7.03 (d, 1H), 5.97-5.83 (m, 1H), 2.05-1.87 (m, 2H), 1.06 (t, 3H).

A48: 3-[difluoro(methoxy)methyl]-6-[6-[1-(trifluoromethyl)propoxy]-3-pyridyl]-[1,2,4]triazolo[4,3-a]pyrazine To a solution of 3-[bromo(difluoro)methyl]-6-[6-[1-(trifluoromethyl)propoxy]-3-pyridyl]-[1,2,4]triazolo[4,3-a]pyrazine (500 mg, 1.11 mmol) in methanol (5 mL) were added $AgBF_4$ (429 mg, 2.21 mmol) and $Na_2CO_3$ (234.4 mg, 2.21 mmol). The mixture was stirred at 70° C. for 4 hours. Water (30 mL) was added and the aqueous layer was extracted with EtOAc (30 mL×3). The combined organic layers were washed with brine (30 mL), dried over anhydrous $Na_2SO_4$, filtered and concentrated to give a crude product. The crude product was purified by flash chromatography on silica gel (EtOAc in PE 0 to 40%) to afford the product (300 mg, 0.74 mmol, 67% yield) as a solid. LCMS Rt=1.02 min in 1.5 min chromatography, 5-95AB, MS ESI calcd. for $C_{16}H_{15}F_5N_5O_2[M+H]^+$ 404.1, found 404.0.

Compounds 13 & 14: 3-[difluoro(methoxy)methyl]-6-[6-[(1R)-1-(trifluoromethyl)propoxy]-3-pyridyl]-[1,2,4]triazolo[4,3-a]pyrazine & 3-[difluoro(methoxy)methyl]-6-[6-[(1S)-1-(trifluoromethyl)propoxy]-3-pyridyl]-[1,2,4]triazolo[4,3-a]pyrazine Analytical SFC: (Chiralpak OJ-3 150×4.6 mm ID, 3 mm. Mobile phase: A: $CO_2$, B: ethanol (0.05% DEA). Gradient: from 5% to 40% of B in 5 min and from 40% to 5% in 0.5 min, hold 5% of B for 1.5 min. Flow rate: 2.5 mL/min Column temperature: 35° C. ABPR: 1500 psi) showed two peaks at 2.45 min (49.9%) and 2.73 min (50.1%). 3-[difluoro(methoxy)methyl]-6-[6-[1-(trifluoromethyl)propoxy]-3-pyridyl]-[1,2,4]triazolo[4,3-a]pyrazine (300 mg, 0.74 mmol) was purified by SFC (DAICEL CHIRALCEL OJ-H (250 mm×30 mm, 5 μm) A=$CO_2$ and B=Neu-EtOH; 70 mL/min; 15% B, injections: 80) to afford the enantiomer 1, randomly assigned as 3-[difluoro(methoxy)methyl]-6-[6-[(1R)-1-(trifluoromethyl)propoxy]-3-pyridyl]-[1,2,4]triazolo[4,3-a]pyrazine (114.98 mg, 0.29 mmol, 26% yield) (Rt of Peak 1=2.552 min) and the enantiomer 2, randomly assigned as 3-[difluoro(methoxy)methyl]-6-[6-[(1S)-1-(trifluoromethyl)propoxy]-3-pyridyl]-[1,2,4]triazolo[4,3-a]pyrazine (120.19 mg, 0.29 mmol, 26% yield) (Rt of Peak 2=2.833 min) as solids. The stereochemistry of 13 and 14 were randomly assigned.

Compound 13: $^1$H NMR (400 MHz, $CDCl_3$) $\delta_H$=9.52 (s, 1H), 8.71 (s, 1H), 8.43 (s, 1H), 8.35-8.18 (m, 1H), 7.10-6.95 (m, 1H), 5.97-5.83 (m, 1H), 3.97 (s, 3H), 2.10-1.85 (m, 2H), 1.15-0.95 (m, 3H). LCMS Rt=1.29 min in 2.0 min chromatography, 10-80AB, MS ESI calcd. for $C_{16}H_{15}F_5N_5O_2[M+H]^+$ 404.1, found 404.2.

Compound 14: $^1$H NMR (400 MHz, $CDCl_3$) $\delta_H$=9.52 (s, 1H), 8.71 (d, 1H), 8.43 (s, 1H), 8.23 (dd, 1H), 7.00 (d, 1H), 5.97-5.83 (m, 1H), 3.97 (s, 3H), 2.07-1.87 (m, 2H), 1.06 (d, 3H). LCMS Rt=1.28 min in 2.0 min chromatography, 10-80AB, MS ESI calcd. for $C_{16}H_{15}F_5N_5O_2[M+H]^+$ 404.1, found 404.2.

Example 12. Synthesis of Compound 15: 3-[difluoro(methoxy)methyl]-6-[6-[(1R)-2,2-difluoro-1-methyl-propoxy]-3-pyridyl]-[1,2,4]triazolo[4,3-a]pyrazine & Compound 16: 3-[difluoro(methoxy)methyl]-6-[6-[(1S)-2,2-difluoro-1-methyl-propoxy]-3-pyridyl]-[1,2,4]triazolo[4,3-a]pyrazine
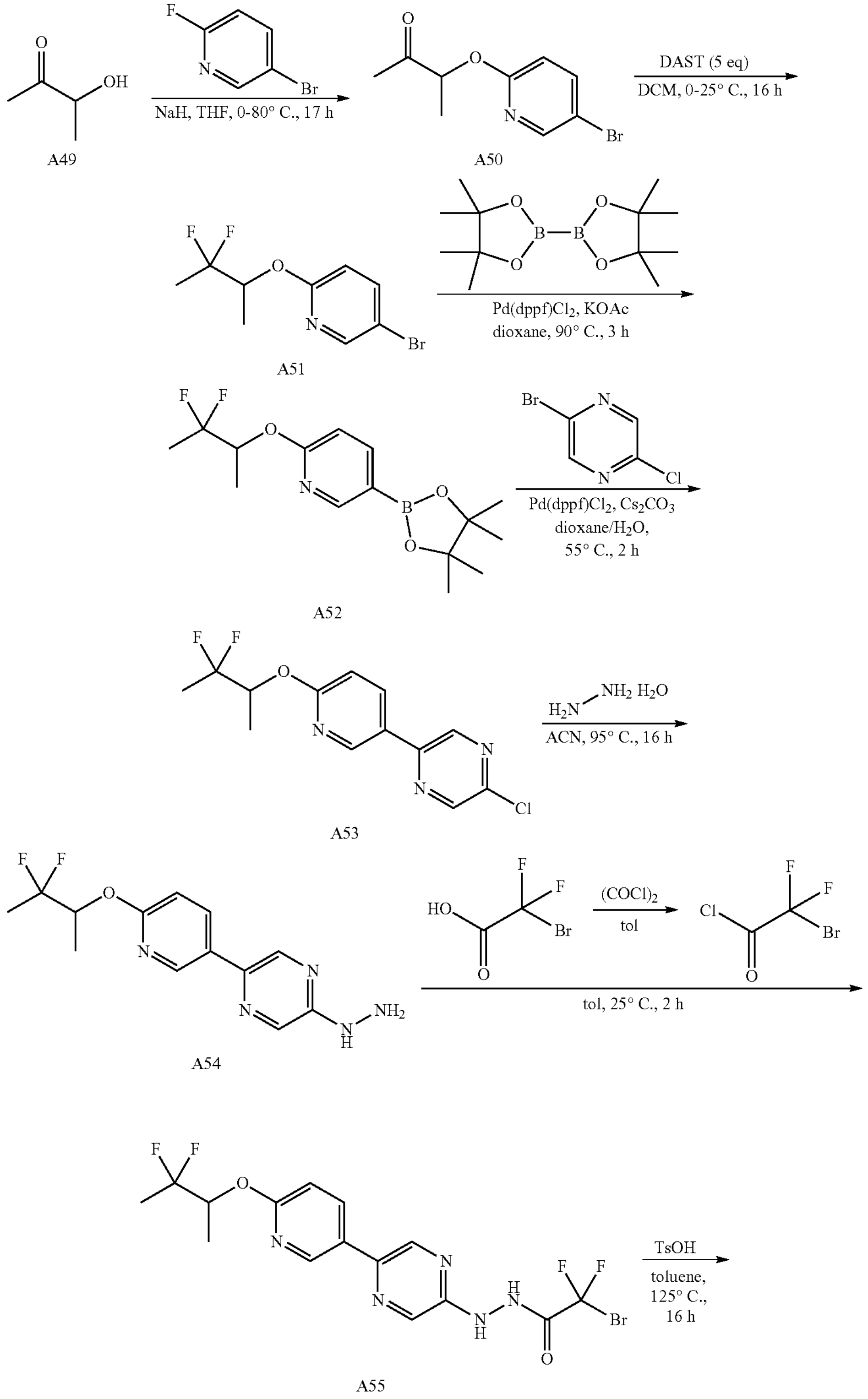
A49 A50 A51 A52 A53 A54 A55

-continued

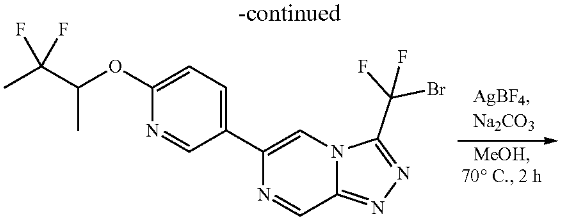

A56

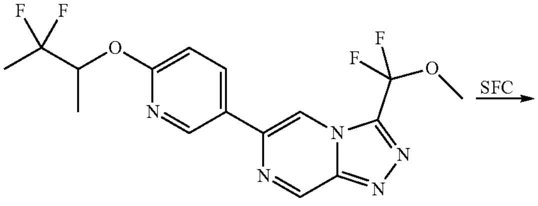

A57

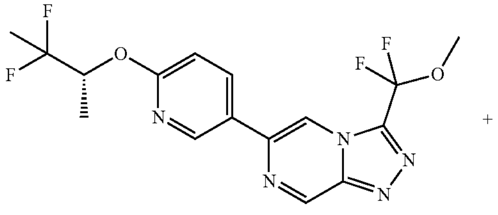

15

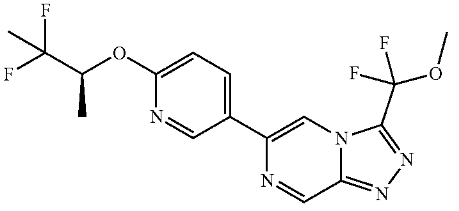

16

A50: 3-[(5-bromo-2-pyridyl)oxy]butan-2-one

To a solution of 3-hydroxybutan-2-one (20.0 g, 226.99 mmol) in THF (500 mL) was added NaH (10.9 g, 272.39 mmol, 60% in oil) in portions at 0° C. The mixture was stirred at 20° C. for 1 hour. Then 5-bromo-2-fluoro-pyridine (39.95 g, 226.99 mmol) was added to the above mixture and the resulting mixture was stirred at 80° C. for 16 hours.

The mixture was poured into water (1 L) and the aqueous layer was extracted with EtOAc (1 L×2). The combined organic phase was washed with brine (500 mL×2), dried over anhydrous $Na_2SO_4$, filtered and concentrated to give a crude product. The crude product was purified by flash chromatography on silica gel (EtOAc in PE=0% to 5% to 10%) to give the product (30.0 g, 122.91 mmol, 54% yield) as an oil. $^1$H NMR (400 MHz, $CDCl_3$) $\delta_H$=8.09 (d, 1H), 7.67 (dd, 1H), 6.75 (d, 1H), 5.21 (q, 1H), 2.18 (s, 3H), 1.48 (d, 3H).

A51: 5-bromo-2-(2,2-difluoro-1-methyl-propoxy)pyridine

To a solution of 3-[(5-bromo-2-pyridyl)oxy]butan-2-one (15.0 g, 61.45 mmol) in DCM (60 mL) was added DAST (40.93 mL, 307.26 mmol) at 0° C. The mixture was stirred at 25° C. for 16 hours. The mixture was added to water (300 mL) dropwise and the aqueous layer was extracted with EtOAc (300 mL×2). The combined organic phase was washed with brine (300 mL), dried over anhydrous $Na_2SO_4$, filtered and concentrated to give a crude product. The crude product was purified by flash chromatography on silica gel (DCM in PE=0% to 2% to 5%) to give the product (5.0 g, 18.79 mmol, 31% yield) as an oil. $^1$H NMR (400 MHz, $CDCl_3$) $\delta_H$=8.18 (d, 1H), 7.69-7.64 (m, 1H), 6.70 (dd, 1H), 5.47-5.37 (m, 1H), 1.66 (t, 3H), 1.39 (d, 3H).

A52: 2-(2,2-difluoro-1-methyl-propoxy)-5-(4,4,5,5-tetramethyl-1,3,2-dioxaborolan-2-yl)pyridine A mixture of 5-bromo-2-(2,2-difluoro-1-methyl-propoxy)pyridine (4.0 g, 15.03 mmol), 4,4,5,5-tetramethyl-2-(4,4,5,5-tetramethyl-1,3,2-dioxaborolan-2-yl)-1,3,2-dioxaborolane (3.82 g, 15.03 mmol), KOAc (2.95 g, 30.07 mmol) and Pd(dppf)$Cl_2$ (550 mg, 0.75 mmol) in 1,4-dioxane (30 mL) was stirred at 90° C. under $N_2$ for 3 hours. After cooling to room temperature, the mixture was filtered through Celite. The filtrate was concentrated and the crude product was purified by flash chromatography on silica gel (DCM in PE=0% to 5%) to give the product (2.5 g, 7.98 mmol, 53% yield) as an oil. LCMS Rt=0.99 min in 1.5 min chromatography, 5-95AB, MS ESI calcd. for $C_{15}H_{23}BF_2NO_3$ $[M+H]^+$ 314.2, found 314.2.

A53: 2-chloro-5-[6-(2,2-difluoro-1-methyl-propoxy)-3-pyridyl]pyrazine

A mixture of 2-(2,2-difluoro-1-methyl-propoxy)-5-(4,4,5,5-tetramethyl-1,3,2-dioxaborolan-2-yl)pyridine (3.5 g, 11.18 mmol), 2-bromo-5-chloro-pyrazine (2.16 g, 11.18 mmol), $Cs_2CO_3$ (7.28 g, 22.35 mmol) and then Pd(dppf)$Cl_2$ (817.8 mg, 1.12 mmol) in 1,4-dioxane (30 mL) and water (3 mL) was stirred at 55° C. for 2 hours. After cooling to room temperature, the mixture was filtered through Celite and concentrated. Water (100 mL) was added and the mixture was extracted with EtOAc (100 mL×2). The combined organic phase was washed with brine (100 mL), dried over anhydrous $Na_2SO_4$, filtered and concentrated to give a crude product. The crude product was purified by flash chromatography on silica gel (EtOAc in PE=0% to 15% to 30%) to give the product (1.8 g, 6.01 mmol, 53% yield) as a solid. $^1H$ NMR (400 MHz, $CDCl_3$) $\delta_H$=8.82-8.70 (m, 2H), 8.63 (d, 1H), 8.24 (dd, 1H), 6.92 (d, 1H), 5.64-5.53 (m, 1H), 1.70 (t, 3H), 1.45 (d, 3H).

A54: [5-[6-(2,2-difluoro-1-methyl-propoxy)-3-pyridyl]pyrazin-2-yl]hydrazine

A mixture of 2-chloro-5-[6-(2,2-difluoro-1-methyl-propoxy)-3-pyridyl]pyrazine (1.8 g, 6.01 mmol) and hydrazine hydrate (3.01 g, 60.06 mmol) in MeCN (20 mL) was stirred at 95° C. for 16 hours. After cooling to room temperature, water (100 mL) was added and the mixture was extracted with EtOAc (100 mL×2). The combined organic phase was washed with brine (100 mL), dried over anhydrous $Na_2SO_4$, filtered and concentrated to give a crude product. The crude product was purified by flash chromatography on silica gel (EtOAc in PE=0% to 50% to 80%) to give the product (1.5 g, 5.08 mmol, 84% yield) as a solid. $^1H$ NMR (400 MHz, DMSO-$d^6$) $\delta_H$=8.70 (d, 1H), 8.55 (d, 1H), 8.25 (dd, 1H), 8.19 (d, 1H), 8.12 (s, 1H), 6.93 (d, 1H), 5.61-5.43 (m, 1H), 4.33 (s, 2H), 1.68 (t, 3H), 1.35 (d, 3H).

A56: 3-[bromo(difluoro)methyl]-6-[6-(2,2-difluoro-1-methyl-propoxy)-3-pyridyl]-[1,2,4]triazolo[4,3-a]pyrazine To a solution of 2-bromo-2,2-difluoro-acetic acid (1.32 g, 7.55 mmol) in toluene (15 mL) was added one drop DMF. Then oxalyl dichloride (0.77 mL, 9.06 mmol) was added to the solution at 0° C. The resulting mixture was stirred at 25° C. for 1 hour. [5-[6-(2,2-difluoro-1-methyl-propoxy)-3-pyridyl]pyrazin-2-yl]hydrazine (1.5 g, 5.08 mmol) was added to the above mixture and the mixture was stirred at 25° C. for 2 hours. TsOH (262 mg, 1.52 mmol) was added and the mixture was stirred at 125° C. for 16 hours. After cooling to room temperature, the mixture was concentrated under reduced pressure. Water (100 mL) was added and the mixture was extracted with EtOAc (100 mL×2). The combined organic phase was washed with brine (100 mL), dried over anhydrous $Na_2SO_4$, filtered and concentrated to give a crude product. The crude product was purified by flash chromatography on silica gel (EtOAc in PE=0% to 20% to 40%) to give the product (1.3 g, 2.99 mmol, 59% yield) as a solid. LCMS Rt=1.30 min in 2.0 min chromatography, 10-80AB, MS ESI calcd. for $C_{15}H_{13}BrF_4N_5O$ $[M+H]^+$ 436.0, found 435.9.

A57: 3-[difluoro(methoxy)methyl]-6-[6-(2,2-difluoro-1-methyl-propoxy)-3-pyridyl]-[1,2,4]triazolo[4,3-a]pyrazine A mixture of 3-[bromo(difluoro)methyl]-6-[6-(2,2-difluoro-1-methyl-propoxy)-3-pyridyl]-[1,2,4]triazolo[4,3-a]pyrazine (1.3 g, 2.99 mmol), $Na_2CO_3$ (634.69 mg, 5.99 mmol) and $AgBF_4$ (1.16 g, 5.99 mmol) in methanol (20 mL) was stirred at 70° C. under dark for 2 hours. After cooling to room temperature, brine (100 mL) and EtOAc (100 mL) were added and the mixture was filtered through Celite. After separating the phases, the organic phase was washed with brine (100 mL), dried over anhydrous $Na_2SO_4$, filtered and concentrated to give a crude product. The crude product was purified by flash chromatography on silica gel (EtOAc in PE=0% to 15% to 30%) and Prep-HPLC (Phenomenex Gemini-NX (80 mm×30 mm, 3 μm) A=$H_2O$ (10 mM $NH_4HCO_3$) and B=$CH_3CN$; 46-56% B over 8 minutes) to give the product (600 mg, 1.56 mmol, 52% yield) as a solid. $^1H$ NMR (400 MHz, $CDCl_3$) $\delta_H$=9.52 (s, 1H), 8.72 (d, 1H), 8.42 (d, 1H), 8.20 (dd, 1H), 6.95 (d, 1H), 5.66-5.53 (m, 1H), 3.97 (s, 3H), 1.71 (t, 3H), 1.46 (d, 3H).

Compounds 15 & 16: 3-[difluoro(methoxy)methyl]-6-[6-[(1R)-2,2-difluoro-1-methyl-propoxy]-3-pyridyl]-[1,2,4]triazolo[4,3-a]pyrazine & 3-[difluoro(methoxy)methyl]-6-[6-[(1S)-2,2-difluoro-1-methyl-propoxy]-3-pyridyl]-[1,2,4]triazolo[4,3-a]pyrazine Analytical SFC: (Chiralcel OJ-3 150×4.6 mm ID, 3 μm. Mobile phase: A: $CO_2$ B: ethanol (0.05% DEA). Gradient: from 5% to 40% of B in 5 min and from 40% to 5% of B in 0.5 min and hold 5% of B for 1.5 min. Flow rate: 2.5 mL/min. Column temperature: 35° C. ABPR: 1500 psi) showed two peaks at 3.57 min (49.91%) and 3.80 min (50.09%). 3-[difluoro(methoxy)methyl]-6-[6-(2,2-difluoro-1-methyl-propoxy)-3-pyridyl]-[1,2,4]triazolo[4,3-a]pyrazine (600 mg, 1.56 mmol) was purified by SFC (DAICEL CHIRALCEL OJ-H (250 mm×30 mm, 5 μm) A=$CO_2$ and B=0.1% $NH_3H_2O$-EtOH; 60 mL/min; 25% B, injections: 170) to afford the enantiomer 1, randomly assigned as 3-[difluoro(methoxy)methyl]-6-[6-[(1R)-2,2-difluoro-1-methyl-propoxy]-3-pyridyl]-[1,2,4]triazolo[4,3-a]pyrazine (226.75 mg, 0.58 mmol, 37% yield) (Rt of Peak 1=3.566 min) and the enantiomer 2, randomly assigned as 3-[difluoro(methoxy)methyl]-6-[6-[(1S)-2,2-difluoro-1-methyl-propoxy]-3-pyridyl]-[1,2,4]triazolo[4,3-a]pyrazine (229.52 mg, 0.60 mmol, 38% yield) (Rt of Peak 2=3.803 min) as solids. The stereochemistry of 15 and 16 were randomly assigned.

Compound 15:

$^1H$ NMR (400 MHz, $CDCl_3$) $\delta_H$=9.52 (s, 1H), 8.72 (d, 1H), 8.42 (d, 1H), 8.20 (dd, 1H), 6.95 (d, 1H), 5.20-5.05 (m, 1H), 3.97 (s, 3H), 1.71 (t, 3H), 146 (d, 3H). LCMS Rt=1.23 min in 2.0 min chromatography, 10-80AB, MS ESI calcd. for $C_{16}H_{16}F_4N_5O_2[M+H]^+$ 386.1, found 386.0.

Compound 16:

$^1H$ NMR (400 MHz, $CDCl_3$) $\delta_H$=9.52 (s, 1H), 8.72 (d, 1H), 8.42 (s, 1H), 8.20 (dd, 1H), 6.95 (d, 1H), 5.20-5.05 (m, 1H), 3.97 (s, 3H), 1.71 (t, 3H), 146 (d, 3H). LCMS Rt=1.23 min in 2.0 min chromatography, 10-80AB, MS ESI calcd. for $C_{16}H_{16}F_4N_5O_2[M+H]^+$ 386.1, found 386.0.

Example 13. Synthesis of Compound 17: 3-[difluoro(propoxy)methyl]-6-[6-[(1R)-2,2,2-trifluoro-1-methyl-ethoxy]-3-pyridyl]-[1,2,4]triazolo[4,3-a]pyrazine

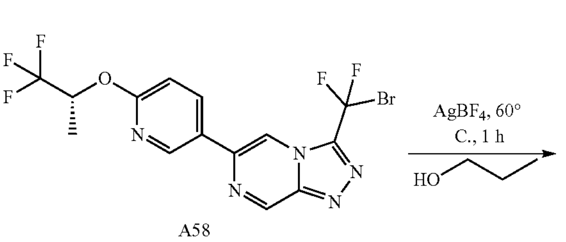

A58

-continued

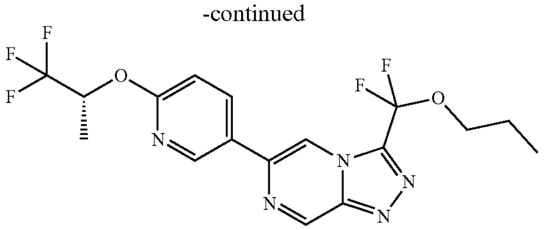

17

Compound 17: 3-[difluoro(propoxy)methyl]-6-[6-[(1R)-2,2,2-trifluoro-1-methyl-ethoxy]-3-pyridyl]-[1,2,4]triazolo[4,3-a]pyrazine To a solution of 3-[bromo(difluoro)methyl]-6-[6-[rac-(1R)-2,2,2-trifluoro-1-methyl-ethoxy]-3-pyridyl]-[1,2,4]triazolo[4,3-a]pyrazine (100 mg, 0.23 mmol) in 1-propanol (3 mL) was added $AgBF_4$ (88.6 mg, 0.46 mmol). The mixture was stirred at 60° C. for 1 hour. After cooling to room temperature, brine (10 mL) and EtOAc (10 mL) was added. The mixture was filtered, and the filter cake was washed with EtOAc (10 mL×3). The filtrate was separated and the organic layer was washed with brine (10 mL), dried over anhydrous $Na_2SO_4$, filtered, and concentrated. The mixture was purified by flash column chromatography (0 to 30% of EtOAc in PE). The mixture was purified by SFC (DAICEL CHIRALCEL OJ-H (250 mm×30 mm, 5 μm); A=$CO_2$ and B=EtOH (0.1% $NH_3.H_2O$); 15% B; 60 mL/min); to give the product (26.8 mg, 0.06 mmol) as a solid. $^1H$ NMR (400 MHz, $CDCl_3$) $\delta_H$=9.51 (d, 1H), 8.70 (d, 1H), 8.45 (d, 1H), 8.21 (dd, 1H), 7.02-6.94 (m, 1H), 5.94-5.80 (m, 1H), 4.24 (t, 2H), 1.96-1.73 (m, 2H), 1.55-1.53 (m, 3H), 1.08 (t, 3H). LCMS Rt=1.32 min in 2.0 min chromatography, 10-80AB, MS ESI calcd. for $C_{17}H_{17}F_5N_5O_2$[M+H]+ 418.1, found 418.1.

Example 14. Synthesis of Compound 18: 3-[difluoro(isopropoxy)methyl]-6-[6-[(1R)-2,2,2-trifluoro-1-methyl-ethoxy]-3-pyridyl]-[1,2,4]triazolo[4,3-a]pyrazine

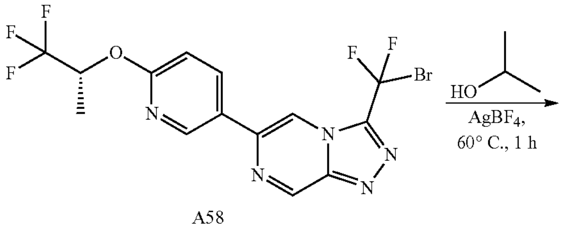

A58

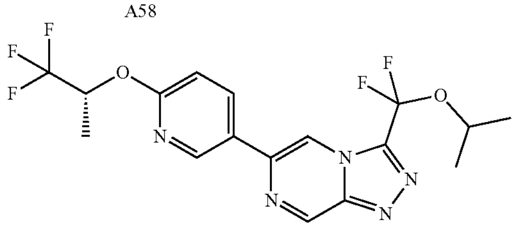

18

Compound 18: 3-[difluoro(isopropoxy)methyl]-6-[6-[(1R)-2,2,2-trifluoro-1-methyl-ethoxy]-3-pyridyl]-[1,2,4]triazolo[4,3-a]pyrazine To a solution of 3-[bromo(difluoro)methyl]-6-[6-[rac-(1R)-2,2,2-trifluoro-1-methyl-ethoxy]-3-pyridyl]-[1,2,4]triazolo[4,3-a]pyrazine (100 mg, 0.23 mmol) in isoamyl alcohol (4 mL) was added $AgBF_4$ (88.6 mg, 0.46 mmol). The mixture was stirred at 60° C. for 1 hour. After cooling to room temperature, brine (10 mL) and EtOAc (10 mL) was added. The mixture was filtered and the filter cake was washed with EtOAc (10 mL×3). The filtrate was separated, and the organic layer was washed with brine (10 mL), dried over anhydrous $Na_2SO_4$, filtered and concentrated. The mixture was purified by flash column chromatography (0 to 30% of EtOAc in PE). The mixture was purified by SFC (DAICEL CHIRALCEL OJ-H (250 mm×30 mm, 5 μm); A=$CO_2$ and B=EtOH (0.1% $NH_3.H_2O$); 15% B; 60 mL/min); to give the product (27.3 mg, 0.07 mmol, 68% yield) as a solid. $^1H$ NMR (400 MHz, $CDCl_3$) $\delta_H$=9.51 (d, 1H), 8.69 (d, 1H), 8.45 (d, 1H), 8.21 (dd, 1H), 6.98 (d, 1H), 5.99-5.73 (m, 1H), 5.11-4.79 (m, 1H), 1.55-1.53 (m, 3H), 1.51 (d, 6H) LCMS Rt=1.31 min in 2.0 min chromatography, 10-80AB, MS ESI calcd. for $C_{17}H_{17}F_5N_5O_2[M+H]^+$ 418.1, found 418.1.

Example 15. Syntheses of Compounds 19 & 20: 3-[ethoxy(difluoro)methyl]-6-[6-[rac-(1R)-1-(trifluoromethyl)propoxy]-3-pyridyl]-[1,2,4]triazolo[4,3-a]pyrazine & 3-[ethoxy(difluoro)methyl]-6-[6-[rac-(1S)-1-(trifluoromethyl)propoxy]-3-pyridyl]-[1,2,4]triazolo[4,3-a]pyrazine

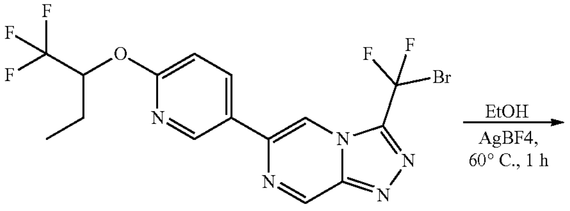

A47

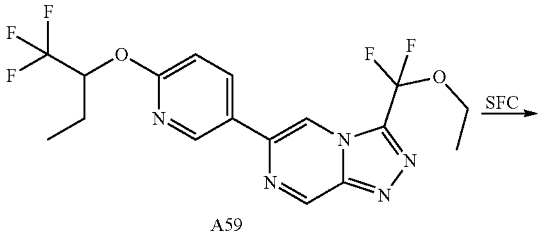

A59

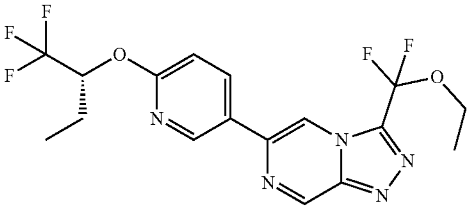

19

-continued

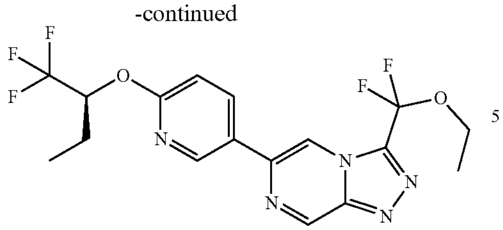

20

A59: 3-[ethoxy(difluoro)methyl]-6-[6-[1-(trifluoromethyl)propoxy]-3-pyridyl]-[1,2,4]triazolo[4,3-a]pyrazine To a solution of 3-[bromo(difluoro)methyl]-6-[6-[1-(trifluoromethyl)propoxy]-3-pyridyl]-[1,2,4]triazolo[4,3-a]pyrazine (300 mg, 0.66 mmol) in ethanol (10 mL) was added $AgBF_4$ (257.4 mg, 1.33 mmol). The mixture was stirred at 60° C. for 1 hour. After cooling to room temperature, brine (10 mL) and EtOAc (10 mL) was added. The mixture was filtered and the filter cake was washed with EtOAc (10 mL×3). The filtrate was separated, and the organic layer was washed with brine (10 mL), dried over anhydrous $Na_2SO_4$, filtered, and concentrated. The mixture was purified by flash column chromatography (0 to 30% of EtOAc in PE) to afford the product (200 mg, 0.48 mmol, 72% yield) as an oil. $^1H$ NMR (400 MHz, $CDCl_3$) $\delta_H$=9.51 (d, 1H), 8.69 (d, 1H), 8.45 (d, 1H), 8.22 (dd, 1H), 7.00 (d, 1H), 5.99-5.82 (m, 1H), 4.40-4.29 (m, 2H), 2.10-1.82 (m, 2H), 1.50 (t, 3H), 1.05 (t, 3H).

Compounds 19 & 20: 3-[ethoxy(difluoro)methyl]-6-[6-[(1R)-1-(trifluoromethyl)propoxy]-3-pyridyl]-[1,2,4]triazolo[4,3-a]pyrazine & 3-[ethoxy(difluoro)methyl]-6-[6-[(1S)-1-(trifluoromethyl)propoxy]-3-pyridyl]-[1,2,4]triazolo[4,3-a]pyrazine. Note that the Stereochemistry is Randomly Assigned The mixture of 3-[ethoxy(difluoro)methyl]-6-[6-[1-(trifluoromethyl)propoxy]-3-pyridyl]-[1,2,4]triazolo[4,3-a]pyrazine (200 mg, 0.48 mmol) was purified by SFC (DAICEL CHIRALCEL OJ-H (250 mm×30 mm, 5 μm); A=$CO_2$ B=EtOH (0.1% $NH_3.H_2O$); 15% B; 60 mL/min); to give 3-[ethoxy(difluoro)methyl]-6-[6-[(1R)-1-(trifluoromethyl)propoxy]-3-pyridyl]-[1,2,4]triazolo[4,3-a]pyrazine (Peak 1, 52.1 mg, 0.12 mmol) as a solid and 3-[ethoxy(difluoro)methyl]-6-[6-[(1S)-1-(trifluoromethyl)propoxy]-3-pyridyl]-[1,2,4]triazolo[4,3-a]pyrazine (Peak 2, 44.3 mg, 0.10 mmol) as a solid.

Compound 19: $^1H$ NMR (400 MHz, $CDCl_3$) $\delta_H$=9.51 (d, 1H), 8.69 (d, 1H), 8.45 (d, 1H), 8.22 (dd, 1H), 7.00 (d, 1H), 5.94-5.84 (m, 1H), 4.40-4.29 (m, 2H), 2.06-1.83 (m, 2H), 1.50 (t, 3H), 1.05 (t, 3H) LCMS Rt=1.33 min in 2.0 min chromatography, 10-80AB, MS ESI calcd. for $C_{17}H_{17}F_5N_5O_2$[M+H]+ 418.1, found 418.1.

Compound 20: $^1H$ NMR (400 MHz, $CDCl_3$) $\delta_H$=9.51 (d, 1H), 8.69 (d, 1H), 8.45 (d, 1H), 8.22 (dd, 1H), 7.00 (d, 1H), 5.95-5.83 (m, 1H), 4.44-4.25 (m, 2H), 2.08-1.83 (m, 2H), 1.50 (t, 3H), 1.05 (t, 3H) Rt=1.34 min in 2.0 min chromatography, 10-80AB, MS ESI calcd. for $C_{17}H_{17}F_5N_5O_2$[M+H]+ 418.1, found 418.1.

Example 16. Synthesis of Compound 21: (S)-3-(difluoro(propoxy)methyl)-6-(6-((1,1,1-trifluoropropan-2-yl)oxy)pyridin-3-yl)-[1,2,4]triazolo[4,3-a]pyrazine

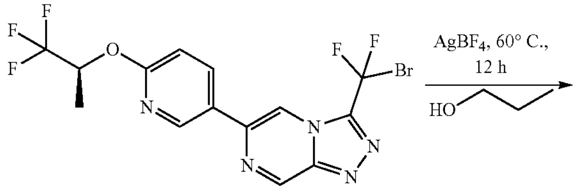

A60

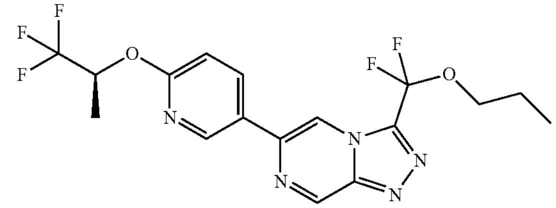

21

Compound 21: (S)-3-(difluoro(propoxy)methyl)-6-(6-((1,1,1-trifluoropropan-2-yl)oxy)pyridin-3-yl)-[1,2,4]triazolo[4,3-a]pyrazine To a solution of (S)-3-(bromodifluoromethyl)-6-(6-((1,1,1-trifluoropropan-2-yl) oxy)pyridin-3-yl)-[1,2,4]triazolo[4,3-a]pyrazine (200 mg, 0.46 mmol) in 1-propanol (5 mL) was added $AgBF_4$ (177.1 mg, 0.91 mmol). After stirring at 60° C. for 12 hours, the mixture was cooled to 25° C., diluted with brine (10 mL), and extracted with EtOAc (2×10 mL). The combined organic layer was washed with brine (20 mL×2), dried over anhydrous $Na_2SO_4$, filtered, and concentrated. The residue was purified by flash column chromatography (0 to 40% of EtOAc in PE) to give the product (117.6 mg, 0.28 mmol, 61% yield) as a solid. $^1H$ NMR (400 MHz, $CDCl_3$) $\delta_H$=9.51 (d, 1H), 8.70 (d, 1H), 8.45 (d, 1H), 8.24-8.16 (m, 1H), 6.98 (d, 1H), 5.95-5.75 (m, 1H), 4.24 (t, 2H), 1.94-1.79 (m, 2H), 1.54 (d, 3H), 1.08 (t, 3H). LCMS Rt=1.072 min in 1.5 min chromatography, 5-95AB, MS ESI calcd. for $C_{17}H_{17}F_5N_5O_2$[M+H]+ 418.1, found 418.1.

Example 17. Synthesis of Compound 22: (S)-3-(difluoro(isopropoxy)methyl)-6-(6-((1,1,1-trifluoropropan-2-yl)oxy)pyridin-3-yl)-[1,2,4]triazolo[4,3-a]pyrazine

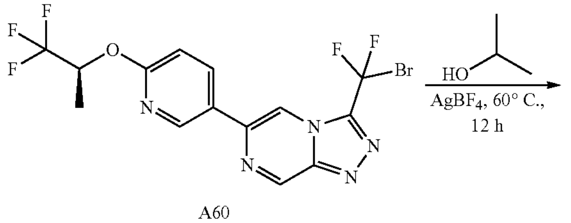

A60

-continued

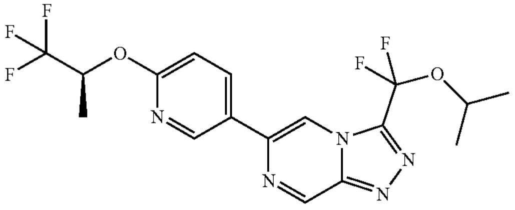

22

Compound 22: (S)-3-(difluoro(isopropoxy)methyl)-6-(6-((1,1,1-trifluoropropan-2-yl)oxy)pyridin-3-yl)-[1,2,4]triazolo[4,3-a]pyrazine To a solution of (S)-3-(bromodifluoromethyl)-6-(6-((1,1,1-trifluoropropan-2-yl)oxy) pyridin-3-yl)-[1,2,4]triazolo[4,3-a]pyrazine (200 mg, 0.46 mmol) in iPrOH (5 mL) was added $AgBF_4$ (177.1 mg, 0.91 mmol). After stirring at 60° C. for 12 hours, the mixture was cooled to 25° C., and brine (10 mL) was added. The mixture was extracted with EtOAc (2×10 mL). The combined organic layer was washed with brine (2×20 mL), dried over anhydrous $Na_2SO_4$, filtered, and concentrated. The residue was purified by flash column chromatography (0 to 40% of EtOAc in PE) to give the product (109.4 mg, 0.26 mmol, 57% yield) as a solid. $^1H$ NMR (400 MHz, $CDCl_3$) $\delta_H$=9.50 (d, 1H), 8.69 (d, 1H), 8.45 (d, 1H), 8.26-8.16 (m, 1H), 6.98 (d, 1H), 5.97-5.77 (m, 1H), 5.12-4.77 (m, 1H), 1.54 (d, 3H), 1.51 (s, 3H), 1.50 (s, 3H). LCMS Rt=1.061 min in 1.5 min chromatography, 5-95AB, MS ESI calcd. for $C_{17}H_{17}F_5N_5O_2$[M+H]+ 418.0, found 418.0.

Example 18. Syntheses of Compounds 24 & 23: (S)-6-(6-((1,1-difluoropropan-2-yl)oxy)pyridin-3-yl)-3-(ethoxydifluoromethyl)-[1,2,4]triazolo[4,3-a]pyrazine & (R)-6-(6-((1,1-difluoropropan-2-yl)oxy)pyridin-3-yl)-3-(ethoxydifluoromethyl)-[1,2,4]triazolo[4,3-a]pyrazine. Note that the Stereochemistry is Randomly Assigned

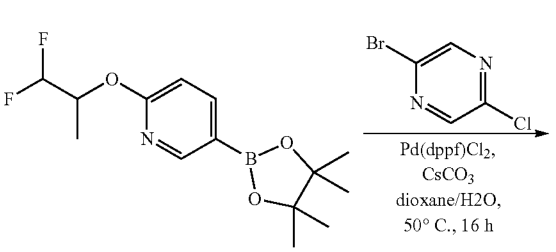

A35

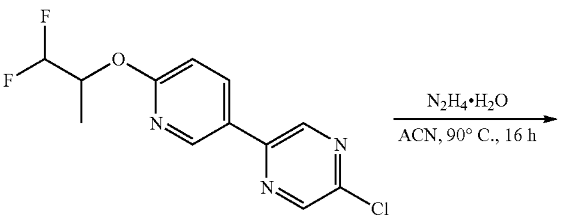

A61

-continued

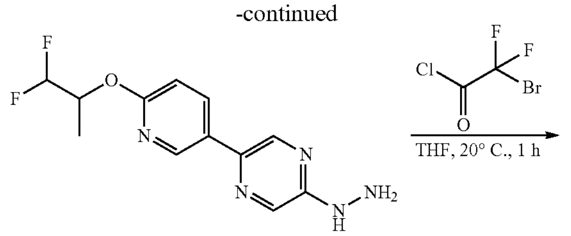

A62

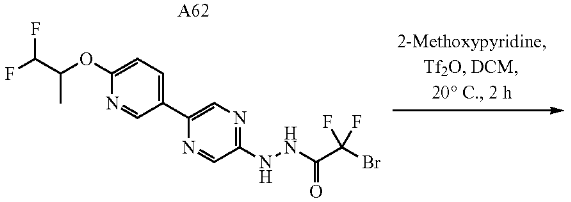

A64

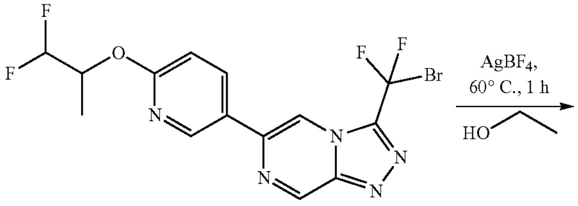

A63

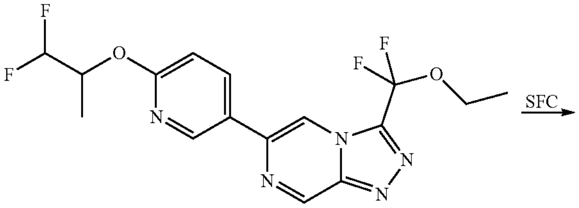

A65

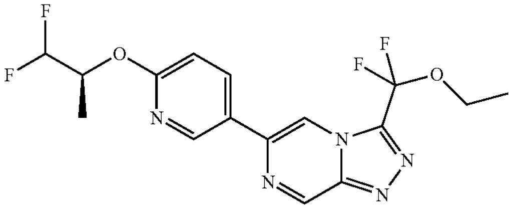

24

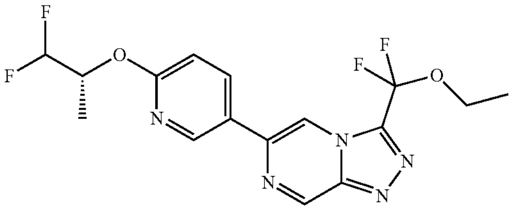

23

A61: 2-chloro-5-[6-(2, 2-difluoro-1-methyl-ethoxy)-3-pyridyl]pyrazine

A mixture of 2-bromo-5-chloro-pyrazine (2.49 g, 12.9 mmol), 2-(2,2-difluoro-1-methyl-ethoxy)-5-(4,4,5,5-tetramethyl-1,3,2-dioxaborolan-2-yl)pyridine (3.50 g, 11.7 mmol), $Pd(dppf)Cl_2$ (0.86 g, 1.17 mmol) and $Cs_2CO_3$ (7.62 g, 23.4 mmol) in 1,4-dioxane (50 mL) and water (5 mL) was stirred at 50° C. for 16 hours under $N_2$. After cooling to 25° C., water phase was separated, and the organic phase was concentrated to remove most of the dioxane. Then the residue was poured into water (50 mL), and the mixture was extracted with EtOAc (2×30 mL). The combined organic phase was washed with water (20 mL) and brine (20 mL), dried over $Na_2SO_4$, filtered, and concentrated. The crude product was purified by flash column chromatography on silica gel (EtOAc in PE=0 to 100 to 300 to 200%) to give the product (2.50 g, 8.75 mmol, 75% yield) as a solid. $^1$H NMR (400 MHz, $CDCl_3$) $\delta_H$=8.76-8.72 (m, 2H), 8.64-8.60 (m, 1H), 8.24 (dd, 1H), 6.91 (d, 1H), 6.14-5.79 (m, 1H), 5.60-5.46 (m, 1H), 1.45 (d, 3H).

A62: [5-[6-(2, 2-difluoro-1-methyl-ethoxy)-3-pyridyl]pyrazin-2-yl] hydrazine

A solution of hydrazine (5.61 g, 175.0 mmol) and 2-chloro-5-[6-(2,2-difluoro-1-methyl-ethoxy)-3-pyridyl] pyrazine (2.50 g, 8.75 mmol) in MeCN (35 mL) was stirred at 90° C. under $N_2$ for 16 hours to give a solution. After cooling to room temperature, the solution was concentrated to give a residue. To the residue was added water (50 mL), and the mixture was extracted with EtOAc (2×50 mL). The combined organic phase was washed with brine (2×50 mL), dried over anhydrous $Na_2SO_4$, filtered, and concentrated to give the (2.50 g, 8.89 mmol, crude) as a solid. $^1$H NMR (400 MHz, $CDCl_3$) $\delta_H$=8.69-8.57 (m, 1H), 8.47-8.38 (m, 1H), 8.34-8.25 (m, 1H), 8.20-8.09 (m, 1H), 6.92-6.80 (m, 1H), 6.16-5.80 (m, 2H), 5.59-5.42 (m, 1H), 4.00-3.85 (m, 2H), 1.50-1.40 (m, 3H).

A64: 2-bromo-N'-[5-[6-(2, 2-difluoro-1-methyl-ethoxy)-5-fluoro-3-pyridyl]pyrazin-2-yl]-2, 2-difluoro-acetohydrazide To a solution of 2-bromo-2,2-difluoro-acetic acid (1.24 g, 7.09 mmol) and 1 mL DMF in THF (10 mL) was added $(COCl)_2$ (0.73 mL, 8.51 mmol), and the mixture was stirred at 0° C. for 1 hour. The mixture was then stirred at 30° C. for 1 hour to provide a first mixture. A mixture of 2-bromo-2,2-difluoro-acetyl chloride (1.35 g, 6.98 mmol) in THF (20 mL) and [5-[6-(2, 2-difluoro-1-methyl-ethoxy)-5-fluoro-3-pyridyl]pyrazin-2-yl]hydrazine (1.90 g, 6.35 mmol) was stirred at 20° C. for 1 hour and then added to the first mixture, and the resulting mixture was stirred at 30° C. for 16 hours. After cooling to room temperature, the mixture was poured into water (30 mL) and extracted with EtOAc (20 mL). The combined organic phase was washed with brine (2×20 mL), dried over anhydrous $Na_2SO_4$, filtered, and concentrated to give the product (2.00 g, 4.35 mmol, 68% yield) as an oil LCMS Rt=1.00 min in 1.5 min chromatography, 5-95AB, MS ESI calcd. for $C_{14}H_{12}BrF_4N_5O_2$ $[M+3H]^+$ 439.8, found 439.8.

A63: 3-[bromo(difluoro)methyl]-6-[6-(2,2-difluoro-1-methyl-ethoxy)-3-pyridyl]-[1,2,4]triazolo[4,3-a] pyrazine To a solution of 2-bromo-N'-[5-[6-(2,2-difluoro-1-methyl-ethoxy)-3-pyridyl]pyrazin-2-yl]-2,2-difluoro-acetohydrazide (2.00 g, 4.56 mmol) in DCM (15 mL) was added 2-methoxypyridine (1.99 g, 18.3 mmol) and $Tf_2O$ (1.54 mL, 9.13 mmol). After stirring at 20° C. for 2 hours, the reaction was poured into water (10 mL) and extracted with EtOAc (10 mL×3). The combined organic phase was washed with saturated $NaHCO_3$ aqueous solution (30 mL×2) and brine (30 mL), dried over anhydrous $Na_2SO_4$, filtered, and concentrated. The residue was purified by flash column chromatography (0 to 30% of EtOAc in PE) to give the product (1.00 g, 2.38 mmol, 52% yield) as an oil. $^1$H NMR (400 MHz, $CDCl_3$) $\delta_H$=9.56 (d, 1H), 8.17 (s, 1H), 7.50-7.25 (m, 1H), 6.99 (d, 2H), 5.23 (s, 2H), 2.40 (s, 3H).

A65: 6-[6-(2,2-difluoro-1-methyl-ethoxy)-3-pyridyl]-3-[ethoxy(difluoro)methyl]-[1, 2, 4]triazolo [4, 3-a]pyrazine To a solution of 3-[bromo(difluoro)methyl]-6-[6-(2,2-difluoro-1-methyl-ethoxy)-3-pyridyl]-[1,2,4]triazolo[4,3-a] pyrazine (500 mg, 1.19 mmol) in ethanol (5 mL) was added $AgBF_4$ (461.7 mg, 2.38 mmol). The mixture was stirred at 60° C. for 3 hours. After cooling to room temperature, brine (10 mL) and EtOAc (10 mL) were added. The mixture was filtered and the filter cake was washed with EtOAc (10 mL×3). The filtrate was separated, and the organic layer was washed with brine (10 mL), dried over anhydrous $Na_2SO_4$, filtered, and concentrated to afford crude product, which was purified by flash column chromatography on silica gel (EtOAc in PE=0 to 1% to 3% to 20%) to give the product (100 mg, 0.26 mmol, 22% yield) as an oil. $^1$H NMR (400 MHz, $CDCl_3$) $\delta_H$=9.51 (d, 1H), 8.70 (d, 1H), 8.46-8.42 (m, 1H), 8.20 (dd, 8.7 Hz, 1H), 6.94 (d, 1H), 6.15-5.82 (m, 1H), 5.60-5.47 (m, 1H), 4.35 (q, 2H), 1.52-1.44 (m, 6H).

Compounds 24 & 23: (S)-6-(6-((1,1-difluoropropan-2-yl)oxy)pyridin-3-yl)-3-(ethoxydifluoromethyl)-[1,2,4]triazolo[4,3-a]pyrazine & (R)-6-(6-((1,1-difluoropropan-2-yl)oxy)pyridin-3-yl)-3-(ethoxydifluoromethyl)-[1,2,4]triazolo[4,3-a] pyrazine The above impure product was purified by Prep-SFC (DAICEL CHIRALCEL OJ-H (250 mm×30 mm, 5 μm); A=$CO_2$ and B=MeOH (0.1% $NH_3.H_2O$); 15% B); to give (S)-6-(6-((1,1-difluoropropan-2-yl)oxy)pyridin-3-yl)-3-(ethoxydifluoromethyl)-[1,2,4]triazolo[4,3-a]pyrazine (31.7 mg, 0.08 mmol) and (R)-6-(6-((1,1-difluoropropan-2-yl) oxy)pyridin-3-yl)-3-(ethoxydifluoromethyl)-[1,2,4]triazolo [4,3-a]pyrazine (23.9 mg, 0.06 mmol) as a solid.

Compound 24: $^1$H NMR (400 MHz, $CDCl_3$) $\delta_H$=9.57-9.47 (m, 1H), 8.77-8.64 (m, 1H), 8.44 (d, 1H), 8.46-8.40 (m, 1H), 8.20 (dd, 1H), 6.94 (d, 1H), 6.21-5.78 (m, 1H), 5.61-5.42 (m, 1H), 4.40-4.29 (m, 1H), 1.52-1.45 (m, 6H). LCMS Rt=1.95 min in 3.0 min chromatography, 10-80AB, MS ESI calcd. for $C_{16}H_{16}F_4N_5O_2[M+H]^+$ 386.2, found 386.2.

Compound 23: $^1$H NMR (400 MHz, $CDCl_3$) $\delta_H$=9.57-9.47 (m, 1H), 8.77-8.64 (m, 1H), 8.44 (d, 1H), 8.46-8.40 (m, 1H), 8.20 (dd, 8.8 Hz, 1H), 6.94 (d, 1H), 6.21-5.78 (m, 1H), 5.61-5.42 (m, 1H), 4.40-4.29 (m, 1H), 1.52-1.45 (m, 6H). LCMS Rt=1.95 min in 3.0 min chromatography, 10-80AB, MS ESI calcd. for $C_{16}H_{16}F_4N_5O_2[M+H]^+$ 386.2, found 386.2.

Example 19. Syntheses of Compounds 25, 26, 27 & 28: (R)-3-(ethoxydifluoromethyl)-6-(6-((1,1,1-trifluoro-3-methylbutan-2-yl)oxy)pyridin-3-yl)-[1,2,4]triazolo[4,3-a]pyrazine & (S)-3-(ethoxydifluoromethyl)-6-(6-((1,1,1-trifluoro-3-methylbutan-2-yl)oxy)pyridin-3-yl)-[1,2,4]triazolo[4,3-a]pyrazine and & (S)-3-(methoxydifluoromethyl)-6-(6-((1,1,1-trifluoro-3-methylbutan-2-yl)oxy)pyridin-3-yl)-[1,2,4]triazolo[4,3-a]pyrazine & (R)-3-(methoxydifluoromethyl)-6-(6-((1,1,1-trifluoro-3-methylbutan-2-yl)oxy)pyridin-3-yl)-[1,2,4]triazolo[4,3-a]pyrazine. Note that the Stereochemistry is Randomly Assigned

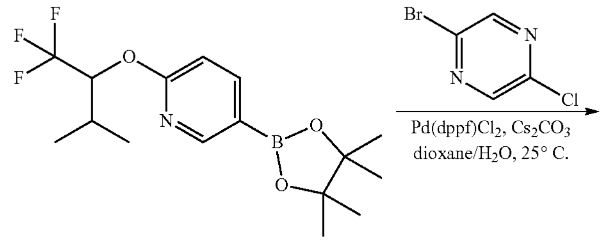

A23

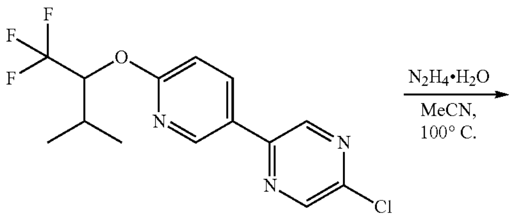

A70

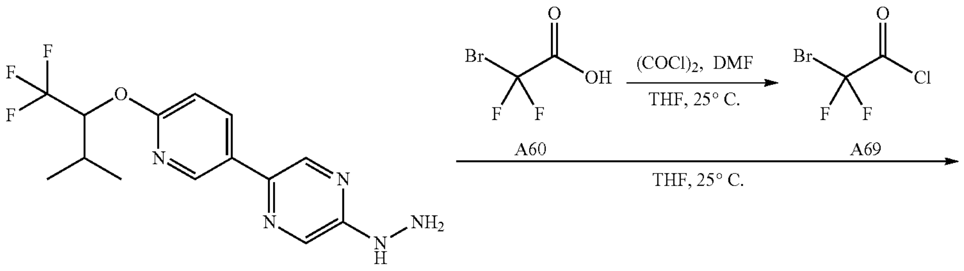

A71

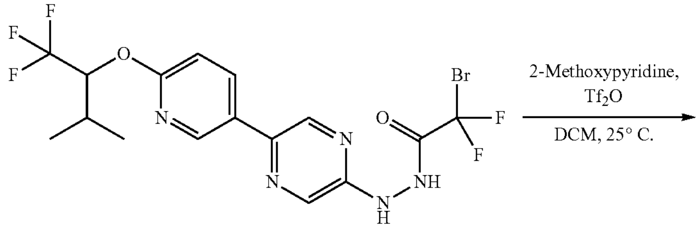

A72

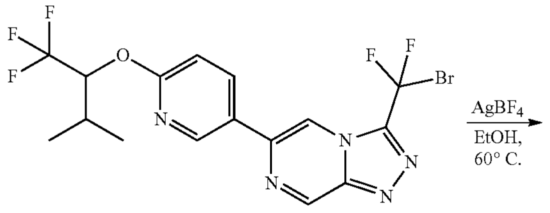

A73

-continued

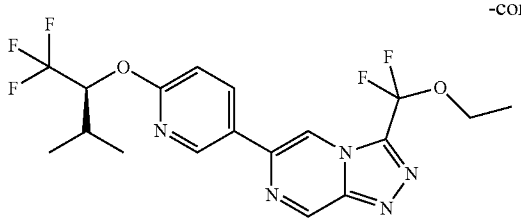

26

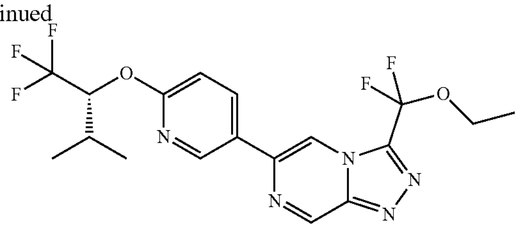

25

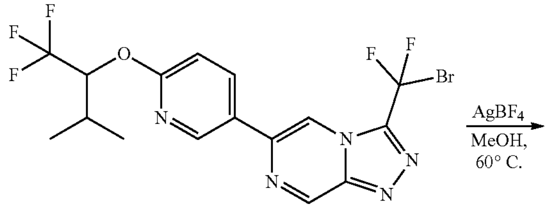

A73

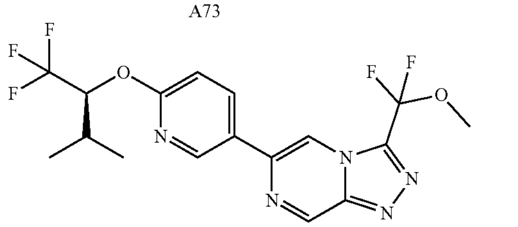

27

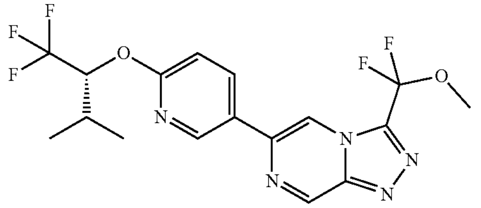

28

A70: 2-chloro-5-[6-[2-methyl-1-(trifluoromethyl)propoxy]-3-pyridyl]pyrazine

To a solution of 2-[2-methyl-1-(trifluoromethyl)propoxy]-5-(4,4,5,5-tetramethyl-1,3,2-dioxaborolan-2-yl)pyridine (8.5 g, 24.6 mmol) in 1,4-dioxane (80 mL) and water (8 mL) was added 2-bromo-5-chloro-pyrazine (4.76 g, 24.6 mmol), $Cs_2CO_3$ (16.0 g, 49.2 mmol), and Pd(dppf)$Cl_2$ (1.08 g, 1.48 mmol) under $N_2$. The reaction was stirred at 25° C. for 16 hours to give a mixture. After cooling to 25° C., the mixture was filtered through Celite, and the filtrate was concentrated in vacuum. The crude mixture was purified by flash column chromatography (EtOAc in PE, 00% to 30%) to give the product (7.8 g, 9500 yield) as a solid. $^1$H NMR (400 MHz, $CDCl_3$) $\delta_H$=8.72-8.63 (m, 2H), 8.56 (d, 1H), 8.19 (dd, 1H), 6.91 (d, 1H), 5.84-5.70 (m, 1H), 2.32-2.15 (m, 1H), 1.02 (d, 6H).

A71: [5-[6-[2-methyl-1-(trifluoromethyl)propoxy]-3-pyridyl]pyrazin-2-yl]hydrazine A mixture of 2-chloro-5-[6-[2-methyl-1-(trifluoromethyl)propoxy]-3-pyridyl]pyrazine (7.8 g, 23.5 mmol) and $N_2H_4$.$H_2O$ (8.85 g, 235 mmol) in MeCN (80 mL) was stirred at 100° C. for 16 hours. After cooling to 25° C., the mixture was poured into water (300 mL), and the mixture was filtered through filter paper. The filter cake was re-dissolved in EtOAc (200 mL), and the mixture was filtered through Celite. The filtrate was washed with brine (200 mL), dried over anhydrous $Na_2SO_4$, filtered, and concentrated to give the product (7 g, 91% yield) as a solid. $^1$H NMR (400 MHz, DMSO-$d_6$) $\delta_H$=8.71 (d, 1H), 8.57 (d, 1H), 8.30 (dd, 1H), 8.23-8.09 (m, 2H), 7.03 (d, 1H), 5.90-5.79 (m, 1H), 4.34 (br s, 2H), 2.32-2.19 (m, 1H), 1.03 (d, 6H).

A69: 2-bromo-2,2-difluoro-acetyl chloride

To a solution of 2-bromo-2,2-difluoro-acetic acid (5 g, 28.5 mmol) and 0.1 mL DMF in THF (75 mL) was added $(COCl)_2$ (2.7 mL, 31.4 mmol), and the mixture was stirred at 25° C. for 1 hour. The solution was used in the next step directly without characterization.

A72: 2-bromo-2,2-difluoro-N'-[5-[6-[2-methyl-1-(trifluoromethyl)propoxy]-3-pyridyl]pyrazin-2-yl]acetohydrazide To a solution of [5-[6-[2-methyl-1-(trifluoromethyl)propoxy]-3-pyridyl]pyrazin-2-yl]hydrazine (7 g, 21.3 mmol) in THF (70 mL) was added 2-bromo-2,2-difluoro-acetyl chloride (5.53 g, 28.5 mmol). The resulting mixture was stirred at 25° C. for 2 hours, followed by addition of water (100 mL). The mixture and the aqueous layer were extracted with EtOAc (100 mL×2). The combined organic phase was washed with brine (100 mL), dried over anhydrous $Na_2SO_4$, filtered, and concentrated to the product (10 g, 97% yield) as an oil, which was used directly for the next step.

A73: 3-[bromo(difluoro)methyl]-6-[6-[2-methyl-1-(trifluoromethyl)propoxy]-3-pyridyl]-[1,2,4]triazolo[4,3-a]pyrazine To a mixture of 2-bromo-2,2-difluoro-N'-[5-[6-[2-methyl-1-(trifluoromethyl)propoxy]-3-pyridyl]pyrazin-2-yl]acetohydrazide (10 g, 20.6 mmol) in DCM (100 mL) was added 2-methoxypyridine (14.2 g, 130 mmol) and $Tf_2O$ (10.5 mL, 62.0 mmol). The mixture was stirred at 25° C. for 16 hours and then treated with water (100 mL). The mixture and the aqueous layer were extracted with EtOAc (100 mL×2). The combined organic phase was washed with saturated $NaHCO_3$ aqueous solution (100 mL) and brine (100 mL), dried over anhydrous $Na_2SO_4$, filtered, and concentrated. The crude product was purified by flash column chromatography on silica gel (EtOAc in PE=0% to 20%) to The product $^1$H NMR (400 MHz, $CDCl_3$) $\delta_H$=9.57 (d, 1H), 8.73

(d, 1H), 8.40 (s, 1H), 8.24 (dd, 1H), 7.02 (d, 1H), 5.92-5.75 (m, 1H), 2.41-2.22 (m, 1H), 1.10 (d, 6H).

Compounds 25 & 26: (R)-3-(ethoxydifluoromethyl)-6-(6-((1,1,1-trifluoro-3-methylbutan-2-yl)oxy)pyridin-3-yl)-[1,2,4]triazolo[4,3-a]pyrazine and (S)-3-(ethoxydifluoromethyl)-6-(6-((1,1,1-trifluoro-3-methylbutan-2-yl)oxy)pyridin-3-yl)-[1,2,4]triazolo[4,3-a]pyrazine. Note the stereochemistry is randomly assigned.

A mixture of 3-[bromo(difluoro)methyl]-6-[6-[2-methyl-1-(trifluoromethyl)propoxy]-3-pyridyl]-[1,2,4]triazolo[4,3-a]pyrazine (400 mg, 0.86 mmol) and $AgBF_4$ (334 mg, 1.72 mmol) in EtOH (4 mL) was stirred at 60° C. in the dark for 3 hours. After cooling to 25° C., the mixture was washed with brine (30 mL), extracted with EtOAc (30 mL×2), dried over anhydrous $Na_2SO_4$, filtered, and concentrated. The crude product was purified by flash column chromatography on silica gel (EtOAc in PE=0% to 20%) to give the product (275 mg, 74% yield) as an oil, which was further purified by SFC (DAICEL CHIRALPAK AD (250 mm×30 mm, 10 μm); $A=CO_2$ and B=EtOH (0.1% $NH_3.H_2O$); 15% B; 60 mL/min; 80 injections) to give (R)-3-(ethoxydifluoromethyl)-6-(6-((1,1,1-trifluoro-3-methylbutan-2-yl)oxy)pyridin-3-yl)-[1,2,4]triazolo[4,3-a]pyrazine (99.62 mg) as a solid and (S)-3-(ethoxydifluoromethyl)-6-(6-((1,1,1-trifluoro-3-methylbutan-2-yl)oxy)pyridin-3-yl)-[1,2,4]triazolo[4,3-a]pyrazine (97.9 mg) as a solid.

Compound 25: $^1H$ NMR (400 MHz, $CDCl_3$) $\delta_H$=9.51 (d, 1H), 8.68 (d, 1H), 8.44 (d, 1H), 8.22 (dd, 1H), 7.01 (d, 1H), 5.91-5.76 (m, 1H), 4.35 (q, 2H), 2.38-2.34 (m, 1H), 1.50 (t, 3H), 1.10 (d, 6H). LCMS Rt=2.033 min in 3 min chromatography, 30-90AB, MS ESI calcd. for $C_{18}H_{19}F_5N_5O_2$[M+H]+ 432.1, found 432.1 Compound 26: $^1H$ NMR (400 MHz, $CDCl_3$) $\delta_H$=9.51 (d, 1H), 8.68 (d, 1H), 8.44 (d, 1H), 8.22 (dd, 1H), 7.01 (d, 1H), 5.91-5.76 (m, 1H), 4.35 (q, 2H), 2.38-2.34 (m, 1H), 1.50 (t, 3H), 1.10 (d, 6H). LCMS Rt=2.024 min in 3 min chromatography, 30-90AB, MS ESI calcd. for $C_{18}H_{19}F_5N_5O_2$[M+H]+ 432.1, found 432.1.

Compounds 27 & 28: (S)-3-(methoxydifluoromethyl)-6-(6-((1,1,1-trifluoro-3-methylbutan-2-yl)oxy)pyridin-3-yl)-[1,2,4]triazolo[4,3-a]pyrazine and (R)-3-(methoxydifluoromethyl)-6-(6-((1,1,1-trifluoro-3-methylbutan-2-yl)oxy)pyridin-3-yl)-[1,2,4]triazolo[4,3-a]pyrazine. Note the Stereochemistry is Randomly Assigned A mixture of 3-[bromo(difluoro)methyl]-6-[6-[2-methyl-1-(trifluoromethyl)propoxy]-3-pyridyl]-[1,2,4]triazolo[4,3-a]pyrazine (400 mg, 0.86 mmol) and $AgBF_4$ (334 mg, 1.72 mmol) in MeOH (4 mL) was stirred at 60° C. in the dark for 3 hours. After cooling to 25° C., the mixture was washed with brine (30 mL), extracted with EtOAc (30 mL×2), dried over anhydrous $Na_2SO_4$, filtered, and concentrated. The crude product was purified by flash column chromatography on silica gel (EtOAc in PE=0% to 30%) to give the product (160 mg, 45% yield) as an oil, which was further purified by SFC (DAICEL CHIRALCEL OJ-H (250 mm×30 mm, 5 μm); $A=CO_2$ and B=IPA (0.1% $NH_3.H_2O$); 15% B; 60 mL/min; 100 injections) to give (S)-3-(methoxydifluoromethyl)-6-(6-((1,1,1-trifluoro-3-methylbutan-2-yl)oxy)pyridin-3-yl)-[1,2,4]triazolo[4,3-a]pyrazine (29.4 mg) as an oil and (R)-3-(methoxydifluoromethyl)-6-(6-((1,1,1-trifluoro-3-methylbutan-2-yl)oxy)pyridin-3-yl)-[1,2,4]triazolo[4,3-a]pyrazine (70 mg) as an oil.

The impure (R)-3-(methoxydifluoromethyl)-6-(6-((1,1,1-trifluoro-3-methylbutan-2-yl)oxy)pyridin-3-yl)-[1,2,4]triazolo[4,3-a]pyrazine (70 mg, 0.17 mmol) was purified by SFC (DAICEL CHIRALCEL OJ-H (250 mm×30 mm, 5 μm), $A=CO_2$ B=IPA (0.1% $NH_3.H_2O$); 15% B; 60 mL/min; 100 injections) to give the product (33.3 mg) as an oil.

Compound 28: $^1H$ NMR (400 MHz, $CDCl_3$) $\delta_H$=9.51 (d, 1H), 8.70 (d, 1H), 8.42 (d, 1H), 8.23 (dd, 1H), 7.01 (d, 1H), 5.89-5.78 (m, 1H), 3.96 (s, 3H), 2.37-2.25 (m, 1H), 1.10 (d, 6H). LCMS Rt=1.879 min in 3 min chromatography, 30-90AB, MS ESI calcd. for $C_{17}H_{17}F_5N_5O_2$[M+H]+ 418.1, found 418.1.

Compound 27: $^1H$ NMR (400 MHz, $CDCl_3$) $\delta_H$=9.51 (d, 1H), 8.70 (d, 1H), 8.42 (d, 1H), 8.23 (dd, 1H), 7.01 (d, 1H), 5.89-5.78 (m, 1H), 3.96 (s, 3H), 2.37-2.25 (m, 1H), 1.10 (d, 6H). LCMS Rt=1.891 min in 3 min chromatography, 30-90AB, MS ESI calcd. for $C_{17}H_{17}F_5N_5O_2$[M+H]+ 418.1, found 418.1.

Example 20. Syntheses of Compounds 29 & 30: (R)-6-(6-(1-cyclopropyl-2,2,2-trifluoroethoxy)pyridin-3-yl)-3-(ethoxydifluoromethyl)-[1,2,4]triazolo[4,3-a]pyrazine & (S)-6-(6-(1-cyclopropyl-2,2,2-trifluoroethoxy)pyridin-3-yl)-3-(ethoxydifluoromethyl)-[1,2,4]triazolo[4,3-a]pyrazine. Note the Stereochemistry is Randomly Assigned

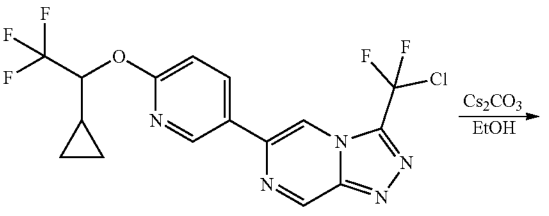

A19

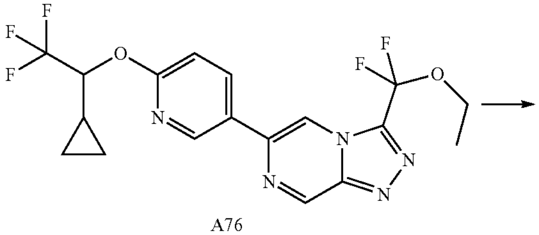

A76

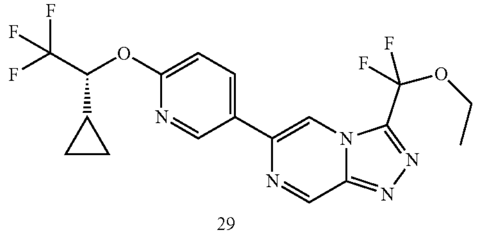

29

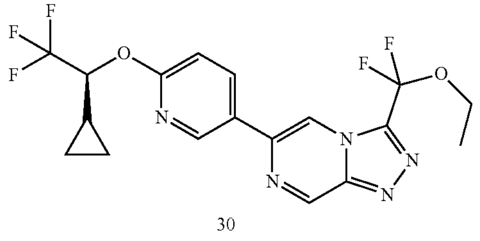

30

A76: 6-(6-(1-cyclopropyl-2,2,2-trifluoroethoxy)pyridin-3-yl)-3-(ethoxydifluoromethyl)-[1,2,4]triazolo[4,3-a]pyrazine To a stirred suspension of $Cs_2CO_3$ (1906.18 mg, 5.85 mmol) in MeCN (15 mL) in 100 mL sealed tube was added ethanol (1.14 mL, 19.5 mmol). The reaction mixture was stirred for 10 min and added 3-[chloro(difluoro)methyl]-6-[6-(1-cyclopropyl-2,2,2-trifluoro-ethoxy)-3-pyridyl]-[1,2,4]triazolo[4,3-a]pyrazine (500 mg, 0.98 mmol) in MeCN (10 mL) at room temperature. The reaction mixture stirred for 30 min at room temperature. The mixture was quenched with ice water (20 mL) and extracted with ethyl acetate (30 mL×2). The organic layer was dried over $Na_2SO_4$ and concentrated. The crude compound was purified by column chromatography silica gel 100-200 mesh using 14% ethyl acetate in PE to provide the product. The product was further purified by preparatory HPLC to afford the product (85.26 mg, 0.20 mmol, 20% yield) as a solid. $^1H$ NMR (400 MHz, $CDCl_3$) $\delta_H$=9.50 (d, 1H), 8.65 (d, 1H), 8.43 (d, 1H), 8.20 (dd, 1H), 7.61-7.42 (m, 1H), 6.98 (d, 1H), 5.41 (dd, 1H), 4.34 (d, 2H), 1.48 (t, 3H), 0.99-0.89 (m, 1H), 0.80-0.69 (m, 1H), 0.66-0.55 (m, 2H)

Compounds 29 & 30: (R)-6-(6-(1-cyclopropyl-2,2,2-trifluoroethoxy)pyridin-3-yl)-3-(ethoxydifluoromethyl)-[1,2,4]triazolo[4,3-a]pyrazine & (S)-6-(6-(1-cyclopropyl-2,2,2-trifluoroethoxy)pyridin-3-yl)-3-(ethoxydifluoromethyl)-[1,2,4]triazolo[4,3-a]pyrazine The mixture of 6-[6-(1-cyclopropyl-2,2,2-trifluoro-ethoxy)-3-pyridyl]-3-[ethoxy(difluoro)methyl]-[1,2,4]triazolo[4,3-a]pyrazine (150 mg, 0.35 mmol) was purified by SFC (DAICEL CHIRALCEL OJ-H (250 mm×30 mm, 5 μm); A=$CO_2$ and B=EtOH (0.1% $NH_3.H_2O$); 10% B) to give (R)-6-(6-(1-cyclopropyl-2,2,2-trifluoroethoxy)pyridin-3-yl)-3-(ethoxydifluoromethyl)-[1,2,4]triazolo[4,3-a]pyrazine (2.44 mg) and (S)-6-(6-(1-cyclopropyl-2,2,2-trifluoroethoxy)pyridin-3-yl)-3-(ethoxydifluoromethyl)-[1,2,4]triazolo[4,3-a]pyrazine (30 mg, 0.07 mmol) as an oil.

The impure (S)-6-(6-(1-cyclopropyl-2,2,2-trifluoroethoxy)pyridin-3-yl)-3-(ethoxydifluoromethyl)-[1,2,4]triazolo[4,3-a]pyrazine (30 mg) was purified by SFC (DAICEL CHIRALCEL OJ-H (250 mm×30 mm, 5 μm), A=$CO_2$ and B=EtOH (0.1% $NH_3.H_2O$); 10% B) to give (S)-6-(6-(1-cyclopropyl-2,2,2-trifluoroethoxy)pyridin-3-yl)-3-(ethoxydifluoromethyl)-[1,2,4]triazolo[4,3-a]pyrazine (4.12 mg) as an oil.

Compound 29: $^1H$ NMR (400 MHz, $CDCl_3$) $\delta_H$=9.53-9.48 (m, 1H), 8.68-8.63 (m, 1H), 8.43 (s, 1H), 8.24-8.17 (m, 1H), 7.02-6.96 (m, 1H), 5.47-5.37 (m, 1H), 4.35 (q, 2H), 1.54-1.46 (m, 2H), 1.34-1.25 (m, 1H), 0.80-0.72 (m, 1H), 2.84-0.57 (m, 4H) LCMS Rt=1.985 min in 3.0 min chromatography, 30-90AB, MS ESI calcd. for $C_{18}H_{17}F_5N_5O_2$ $[M+H]^+$ 430.1, found 430.1.

Compound 30: $^1H$ NMR (400 MHz, $CDCl_3$) $\delta_H$=9.55-9.44 (m, 1H), 8.68-8.64 (m, 1H), 8.43 (s, 1H), 8.24-8.18 (m, 1H), 7.03-6.97 (m, 1H), 5.47-5.37 (m, 1H), 4.40-4.31 (m, 2H), 1.53-1.46 (m, 3H), 1.35-1.24 (m, 1H), 0.81-0.73 (m, 1H), 0.62 (br t, 3H) LCMS Rt=1.888 min in 3.0 min chromatography, 30-90AB, MS ESI calcd. for $C_{18}H_{17}F_5N_5O_2[M+H]^+$ 430.1, found 430.1.

Example 21. Syntheses of Compounds 31 & 32: 3-[ethoxy(difluoro)methyl]-6-[6-[(1R)-1-ethyl-2,2-difluoro-propoxy]-3-pyridyl]-[1,2,4]triazolo[4,3-a]pyrazine & 3-[ethoxy(difluoro)methyl]-6-[6-[(1S)-1-ethyl-2,2-difluoro-propoxy]-3-pyridyl]-[1,2,4]triazolo[4,3-a]pyrazine. Note the Stereochemistry is Randomly Assigned

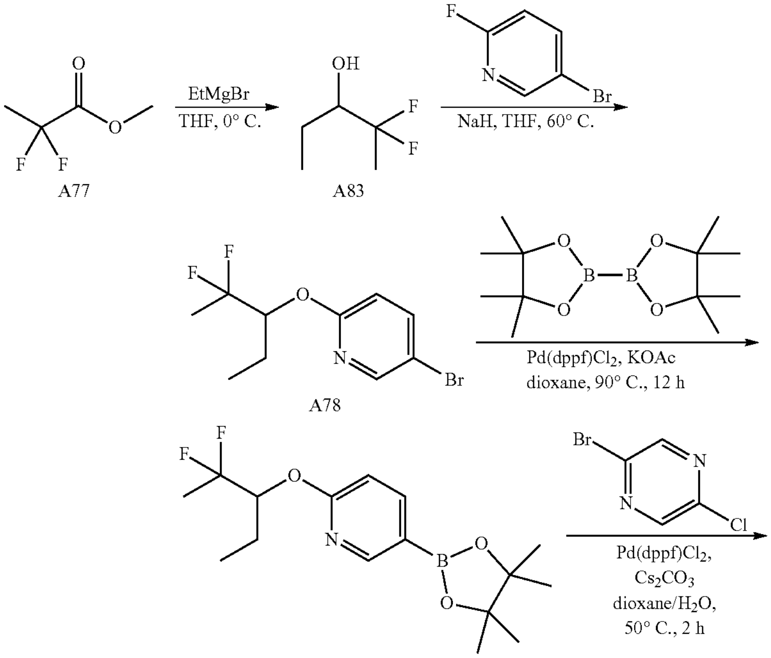

A77
A83
A78
A79

-continued
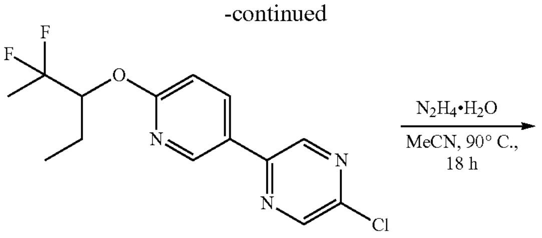
A80
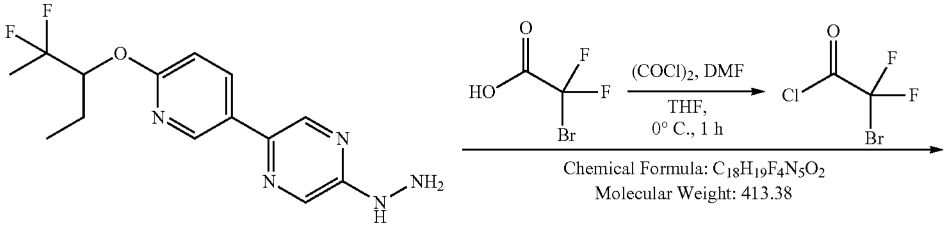
A81
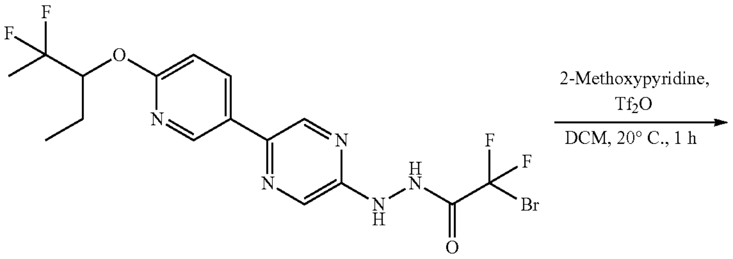
A84
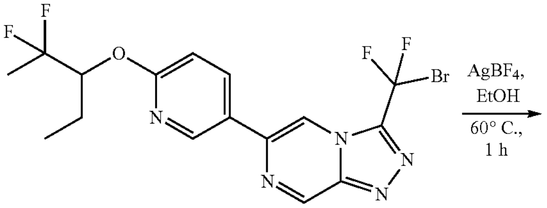
A82
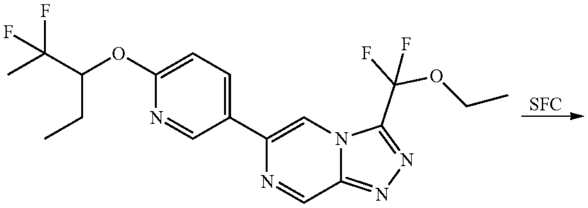
A85
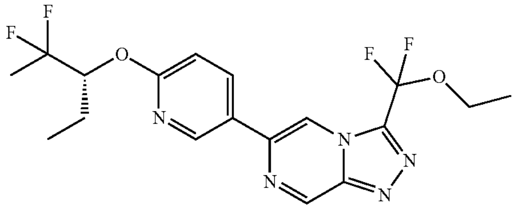
31
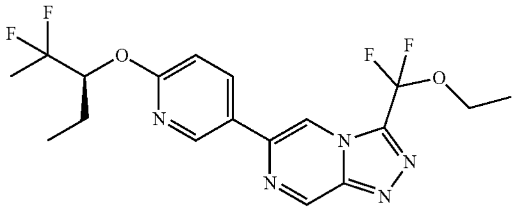
32

A83: 2,2-difluoropentan-3-ol

To a mixture of methyl 2,2-difluoropropanoate (5 g, 40.3 mmol) in THF (50 mL) was added EtMgBr (26.9 mL, 80.6 mmol) dropwise (3 M in $Et_2O$) at 0° C. The mixture was warmed to 20° C. and stirred for 2 hours. To the mixture was added saturated $NH_4Cl$ solution (50 mL), and the aqueous layer was extracted with THF (10 mL×2). The combined organic layers were washed with brine (20 mL) and dried over anhydrous $Na_2SO_4$ to afford 2,2-difluoropentan-3-ol (5 g, 12.1 mmol, 30.0% yield) as an oil, which was used directly in the next step.

A78: 5-bromo-2-(1-ethyl-2,2-difluoro-propoxy)pyridine

To a solution of 2,2-difluoropentan-3-ol (5 g, 40.3 mmol) in THF (50 mL) was added NaH (3.22 g, 80.6 mmol) at 0° C. for 30 minutes, followed by addition of 5-bromo-2-fluoro-pyridine (6.38 g, 36.3 mmol). The mixture was stirred at 60° C. for 16 hours. After cooling to room temperature, the mixture was diluted with saturated $NH_4Cl$ solution (100 mL) and extracted with EtOAc (100 mL×2). The combined organic phase was washed with brine (30 mL), dried over $Na_2SO_4$, filtered and concentrated to give the crude product, which was purified by flash chromatography on silica gel (EtOAc in PE=0% to 1% to 2%) to give the product (7.4 g, 24.2 mmol, 60% yield) as an oil. $^1H$ NMR (400 MHz, $CDCl_3$) $\delta_H$=8.19-8.11 (m, 1H), 7.70-7.63 (m, 1H), 6.71 (d, 1H), 5.55-5.39 (m, 1H), 1.92-1.82 (m, 1H), 1.81-1.70 (m, 1H), 1.66-1.57 (m, 3H), 0.95 (t, 3H).

A79: 2-(1-ethyl-2,2-difluoro-propoxy)-5-(4,4,5,5-tetramethyl-1,3,2-dioxaborolan-2-yl)pyridine A mixture of 5-bromo-2-(1-ethyl-2,2-difluoro-propoxy) pyridine (7.4 g, 26.4 mmol), 4,4,5,5-tetramethyl-2-(4,4,5,5-tetramethyl-1,3,2-dioxaborolan-2-yl)-1,3,2-dioxaborolane (7.38 g, 29.1 mmol), Pd(dppf)$Cl_2$ (1.93 g, 2.64 mmol) and KOAc (5.19 g, 52.8 mmol) in 1,4-dioxane (100 mL) was stirred at 90° C. for 16 hours under $N_2$. The mixture was cooled to room temperature, filtered and concentrated to give the crude product, which was purified by flash chromatography on silica gel (EtOAc in PE=0% to 1% to 2%) to give the product (6.1 g, 18.6 mmol, 71% yield) as an oil. $^1H$ NMR (400 MHz, $CDCl_3$) $\delta_H$=8.50 (d, 1H), 7.97-7.91 (m, 1H), 6.76 (d, 1H), 5.73-5.57 (m, 1H), 1.94-1.83 (m, 1H), 1.82-1.73 (m, 1H), 1.64 (s, 1H), 1.60 (s, 2H), 1.33 (s, 12H), 0.95 (t, 3H).

A80: 2-chloro-5-[6-(1-ethyl-2,2-difluoro-propoxy)-3-pyridyl]pyrazine

A mixture of Pd(dppf)$Cl_2$ (0.85 g, 1.16 mmol), $Cs_2CO_3$ (7.57 g, 23.2 mmol), 2-bromo-5-chloro-pyrazine (2.47 g, 12.8 mmol) and 2-(1-ethyl-2,2-difluoro-propoxy)-5-(4,4,5,5-tetramethyl-1,3,2-dioxaborolan-2-yl)pyridine (3.8 g, 11.6 mmol) in 1,4-dioxane (50 mL) and water (5 mL) was stirred at 50° C. for 2 hours under $N_2$. After cooling to 25° C., the aqueous phase was separated, and the organic phase was concentrated to remove most of the dioxane. Then the residue was diluted with water (30 mL), and the mixture was extracted with EtOAc (60 mL×2). The combined organic phase was washed with water (40 mL) and brine (40 mL), dried over $Na_2SO_4$, filtered and concentrated. The crude product was purified by flash chromatography on silica gel (EtOAc in PE=0% to 1% to 3% to 20%) to the product (3 g, 9.56 mmol, 82% yield) as a solid. $^1H$ NMR (400 MHz, $CDCl_3$) δ=8.74 (d, 2H), 8.62 (d, 1H), 8.26-8.20 (m, 1H), 6.93 (d, 1H), 5.72-5.60 (m, 1H), 1.97-1.75 (m, 2H), 1.64 (t, 3H), 0.99 (t, 3H).

A81: [5-[6-(1-ethyl-2,2-difluoro-propoxy)-3-pyridyl]pyrazin-2-yl]hydrazine

A solution of 2-chloro-5-[6-(1-ethyl-2,2-difluoro-propoxy)-3-pyridyl]pyrazine (3 g, 9.56 mmol) and hydrazine (6.13 g, 191 mmol) in MeCN (50 mL) was stirred at 90° C. under $N_2$ for 16 hours to give a brown solution. After cooling to room temperature, the solution was concentrated, diluted with water (50 mL) and extracted with EtOAc (50 mL×2). The combined organic phase was washed with brine (50 mL×2), dried over anhydrous $Na_2SO_4$, filtered and concentrated to give the product (2.6 g, 8.41 mmol, 88% yield) as a solid. The crude residue was used directly for the next step.

A84: 2-bromo-N'-[5-[6-(1-ethyl-2,2-difluoro-propoxy)-3-pyridyl]pyrazin-2-yl]-2,2-difluoro-aceto-hydrazide To a solution of 2-bromo-2,2-difluoro-acetic acid (4 g, 22.9 mmol) in THF (40 mL) was added oxalyl chloride (2.35 mL, 27.4 mmol) and DMF (1 mL). The mixture was stirred at 0° C. for 1 hour. The solution was used for the next step directly without further purification.

To above solution of 2-bromo-2,2-difluoro-acetyl chloride was added [5-[6-(1-ethyl-2,2-difluoro-propoxy)-3-pyridyl]pyrazin-2-yl]hydrazine (2.60 g, 8.41 mmol), and the resulting mixture was stirred at 0° C. for 2 hours. After warming to room temperature, the mixture was poured into water (40 mL) and extracted with EtOAc (40 mL). The combined organic phase was washed with brine (20 mL×2), dried over anhydrous $Na_2SO_4$, filtered and concentrated to give the product (7.60 g, 16.3 mmol) as an oil. LCMS Rt=0.980 min in 1.5 min chromatography, 5-95AB, MS ESI calcd for $C_{16}H_{17}BrF_4N_5O_2$ [M+H]+ 468.0, found 468.0.

A82: 3-[bromo(difluoro)methyl]-6-[6-(1-ethyl-2,2-difluoro-propoxy)-3-pyridyl]-[1,2,4]triazolo[4,3-a]pyrazine To a yellow mixture of 2-bromo-N'-[5-[6-(1-ethyl-2,2-difluoro-propoxy)-3-pyridyl]pyrazin-2-yl]-2,2-difluoro-acetohydrazide (4.40 g, 9.44 mmol) in DCM (40 mL) was added 2-methoxypyridine (4 mL, 37.8 mmol) and $Tf_2O$ (3.19 mL, 18.9 mmol), and the resulting mixture was stirred at 20° C. under $N_2$ for 1 hour. The mixture was then diluted with water (40 mL) and extracted with DCM (40 mL×2). The organic layers were dried over anhydrous $Na_2SO_4$, filtered and concentrated. The residue was purified by flash column chromatography (20 to 30% of EtOAc in PE) to afford the product (800 mg, 1.78 mmol, 19% yield) as a solid. $^1H$ NMR (400 MHz, $CDCl_3$) $\delta_H$=9.58 (d, 1H), 8.73 (d, 1H), 8.45-8.37 (m, 1H), 8.26-8.17 (m, 1H), 7.01-6.93 (m, 1H), 5.72-5.59 (m, 1H), 1.72-1.59 (m, 3H), 1.27-1.24 (m, 2H), 1.03-0.97 (m, 3H). LCMS Rt=1.035 min in 4.0 min chromatography, 30-90AB, MS ESI calcd for $C_{16}H_{15}BrF_4N_5O$ $[M+H]^+$ 447.9, found 447.9.

A85: 3-[ethoxy(difluoro)methyl]-6-[6-(1-ethyl-2,2-difluoro-propoxy)-3-pyridyl]-[1,2,4]triazolo[4,3-a]pyrazine A mixture of 3-[bromo(difluoro)methyl]-6-[6-(1-ethyl-2,2-difluoro-propoxy)-3-pyridyl]-[1,2,4]triazolo[4,3-a]pyrazine (400 mg, 0.89 mmol) and $AgBF_4$ (347.5 mg, 1.78 mmol) in ethanol (4 mL) was stirred at 60° C. in the dark for 1 hour. After cooling to 25° C., the mixture was washed with brine (10 mL) and extracted with EtOAc (10 mL×2). The organic layers were dried over anhydrous $Na_2SO_4$, filtered and concentrated. The crude product was purified by flash chromatography on silica gel (EtOAc in PE=0% to 30%) to give the product (60 mg, 0.15 mmol, 16% yield) as a solid. $^1H$ NMR (400 MHz, $CDCl_3$) $\delta_H$=9.51 (d, 1H), 8.68 (d, 1H), 8.44 (d, 1H), 8.24-8.16 (m, 1H), 6.96 (d, 1H), 5.75-5.59 (m, 1H), 4.40-4.31 (m, 2H), 1.97-1.76 (m, 2H), 1.72-1.61 (m, 3H), 1.53-1.46 (m, 3H), 1.04-0.97 (m, 3H).

Compounds 31 & 32: 3-[ethoxy(difluoro)methyl]-6-[6-[(1R)-1-ethyl-2,2-difluoro-propoxy]-3-pyridyl]-[1,2,4]triazolo[4,3-a]pyrazine & 3-[ethoxy(difluoro)methyl]-6-[6-[(1S)-1-ethyl-2,2-difluoro-propoxy]-3-pyridyl]-[1,2,4]triazolo[4,3-a]pyrazine The residue was purified by SFC (DAICEL CHIRALCEL OJ-H (250 mm×30 mm, 5 μm), A: $CO_2$, B=MeOH 0.1% $NH_3.H_2O$, 25% B, 60 mL/min) to afford 3-[ethoxy(difluoro)methyl]-6-[6-[(1R)-1-ethyl-2,2-difluoro-propoxy]-3-pyridyl]-[1,2,4]triazolo[4,3-a]pyrazine (30 mg, 0.07 mmol) as an oil and 3-[ethoxy(difluoro)methyl]-6-[6-[rac-(1S)-1-ethyl-2,2-difluoro-propoxy]-3-pyridyl]-[1,2,4]triazolo[4,3-a]pyrazine (25 mg, 0.06 mmol) as an oil. The impure 3-[ethoxy(difluoro)methyl]-6-[6-[(1R)-1-ethyl-2,2-difluoro-propoxy]-3-pyridyl]-[1,2,4]triazolo[4,3-a]pyrazine (30 mg, 0.07 mmol) was purified by prep-TLC to afford 3-[ethoxy(difluoro)methyl]-6-[6-[(1R)-1-ethyl-2,2-difluoro-propoxy]-3-pyridyl]-[1,2,4]triazolo[4,3-a]pyrazine (8.02 mg, 0.02 mmol) as an oil. The impure 3-[ethoxy(difluoro)methyl]-6-[6-[(1S)-1-ethyl-2,2-difluoro-propoxy]-3-pyridyl]-[1,2,4]triazolo[4,3-a]pyrazine (25 mg, 0.06 mmol) was purified by prep-TLC to give 3-[ethoxy(difluoro)methyl]-6-[6-[(1S)-1-ethyl-2,2-difluoro-propoxy]-3-pyridyl]-[1,2,4]triazolo[4,3-a]pyrazine (22.57 mg, 0.05 mmol) as a solid.

Compound 31: $^1H$ NMR (400 MHz, $CDCl_3$) $\delta_H$=9.50 (s, 1H), 8.68 (d, 1H), 8.44 (s, 1H), 8.24-8.14 (m, 1H), 6.96 (d, 1H), 5.76-5.54 (m, 1H), 4.41-4.29 (m, 2H), 1.99-1.88 (m, 1H), 1.86-1.76 (m, 1H), 1.73-1.62 (m, 3H), 1.54-1.44 (m, 3H), 1.05-0.95 (m, 3H). LCMS Rt=1.292 min in 2.0 min chromatography, 10-80AB, MS ESI calcd for $C_{18}H_{20}F_4N_5O_2[M+H]^+$ 414.1, found 414.1.

Compound 32: $^1H$ NMR (400 MHz, $CDCl_3$) $\delta_H$=9.51 (s, 1H), 8.69 (d, 1H), 8.44 (s, 1H), 8.24-8.16 (m, 1H), 6.96 (d, 1H), 5.76-5.51 (m, 1H), 4.41-4.29 (m, 2H), 1.96-1.89 (m, 1H), 1.86-1.76 (m, 1H), 1.72-1.59 (m, 3H), 1.53-1.45 (m, 3H), 1.05-0.96 (m, 3H). LCMS Rt=1.283 min in 2.0 min chromatography, 10-80AB, MS ESI calcd for $C_{18}H_{20}F_4N_5O_2[M+H]^+$ 414.1, found 414.1.

Example 22. Syntheses of Compounds 33 & 34: 3-[ethoxy(difluoro)methyl]-6-[6-[(1R)-1-ethyl-2,2-difluoro-propoxy]-3-pyridyl]-[1,2,4]triazolo[4,3-a]pyrazine & 3-[ethoxy(difluoro)methyl]-6-[6-[(1S)-1-ethyl-2,2-difluoro-propoxy]-3-pyridyl]-[1,2,4]triazolo[4,3-a]pyrazine. Note the Stereochemistry is Randomly Assigned

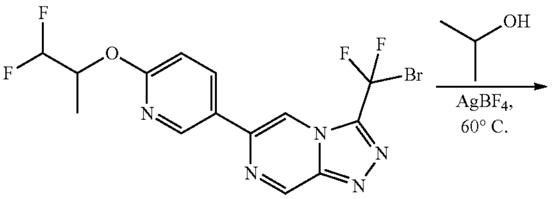

A63

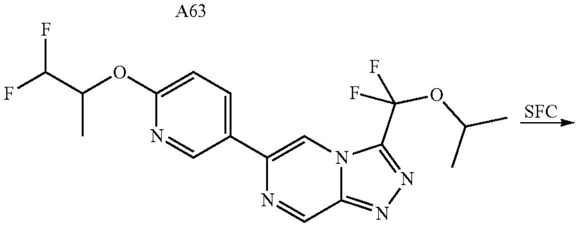

A86

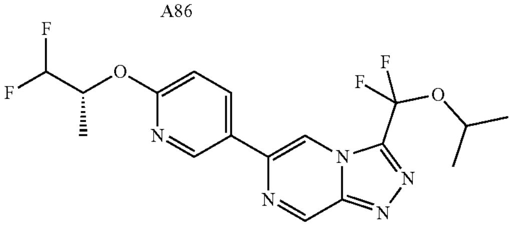

33

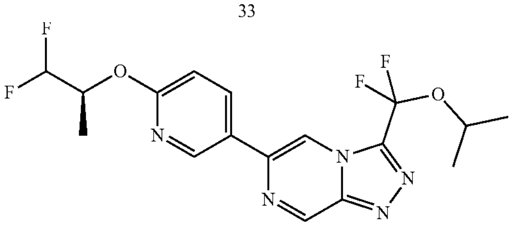

34

A86: 3-[difluoro(isopropoxy)methyl]-6-[6-(2,2-difluoro-1-methyl-ethoxy)-3-pyridyl]-[1,2,4]triazolo[4,3-a]pyrazine To a solution of 3-[bromo(difluoro)methyl]-6-[6-(2,2-difluoro-1-methyl-ethoxy)-3-pyridyl]-[1,2,4]triazolo[4,3-a]pyrazine (100 mg, 0.24 mmol) in IPA (3 mL) was added $AgBF_4$ (92.4 mg, 0.48 mmol) under $N_2$. After stirring at 60° C. for 12 hours, the mixture was cooled to 25° C. and diluted with brine (10 mL). The mixture was extracted with EtOAc (2×10 mL). The combined organic layer was washed with brine (2×10 mL), dried over anhydrous $Na_2SO_4$, filtered and concentrated. The residue was purified by flash column chromatography (0 to 40% of EtOAc in PE) to give the product (40 mg, 0.1 mmol, 42% yield) as a solid. $^1H$ NMR (400 MHz, $CDCl_3$) $\delta_H$=9.58-9.46 (m, 1H), 8.80-8.64 (m, 1H), 8.44 (d, 1H), 8.19 (dd, 1H), 6.94 (d, 1H), 6.16-5.78 (m, 1H), 5.66-5.46 (m, 1H), 5.08-4.90 (m, 1H), 1.51 (d, 6H), 1.47 (d, 3H).

Compounds 33& 34: 3-[difluoro(isopropoxy)methyl]-6-[6-[(1R)-2,2-difluoro-1-methyl-ethoxy]-3-pyridyl]-[1,2,4]triazolo[4,3-a]pyrazine & 3-[difluoro(isopropoxy)methyl]-6-[6-[(1S)-2,2-difluoro-1-methyl-ethoxy]-3-pyridyl]-[1,2,4]triazolo[4,3-a]pyrazine The racemic product was purified by SFC (DAICEL CHIRALCEL AY-H (250 mm×30 mm, 5 μm); A: $CO_2$ B=EtOH 0.1% $NH_3.H_2O$; 15% B) to give the product of 3-[difluoro(isopropoxy)methyl]-6-[6-[(1R)-2,2-difluoro-1-methyl-ethoxy]-3-pyridyl]-[1,2,4]triazolo[4,3-a]pyrazine (Peak 1, 11.07 mg) and 3-[difluoro(isopropoxy)methyl]-6-[6-[(1S)-2,2-difluoro-1-methyl-ethoxy]-3-pyridyl]-[1,2,4]triazolo[4,3-a]pyrazine (Peak 2, 7.39 mg) as solid.

Compound 33: $^1H$ NMR (400 MHz, $CDCl_3$) $\delta_H$=9.51 (s, 1H), 8.71-8.66 (m, 1H), 8.44 (s, 1H), 8.19 (dd, 1H), 6.95 (d, 1H), 6.18-5.80 (m, 1H), 5.62-5.42 (m, 1H), 5.11-4.90 (m, 1H), 1.51 (d, 6H), 1.47 (d, 3H). LCMS Rt=1.95 min in 3.0 min chromatography, 10-80AB, MS ESI calcd. for $C_{17}H_{18}F_4N_5O_2[M+H]^+$ 400.2, found 400.2.

Compound 34: $^1H$ NMR (400 MHz, $CDCl_3$) $\delta_H$=9.51 (s, 1H), 8.70-8.67 (m, 1H), 8.45 (s, 1H), 8.19 (dd, 1H), 6.95 (d, 1H), 6.16-5.79 (m, 1H), 5.63-5.46 (m, 1H), 5.14-4.90 (m, 1H), 1.50 (d, 6H), 1.47 (d, 3H). LCMS Rt=1.95 min in 3.0 min chromatography, 10-80AB, MS ESI calcd. for $C_{17}H_{18}F_4N_5O_2[M+H]^+$ 400.2, found 400.2.

Example 23. Syntheses of Compounds 35 & 36: 3-[difluoro(methoxy)methyl]-6-[6-[rac-(1R)-1-(difluoromethyl)propoxy]-3-pyridyl]-[1,2,4]triazolo[4,3-a]pyrazine & 3-[difluoro(methoxy)methyl]-6-[6-[rac-(1S)-1-(difluoromethyl)propoxy]-3-pyridyl]-[1,2,4]triazolo[4,3-a]pyrazine. Note the Stereochemistry is Randomly Assigned

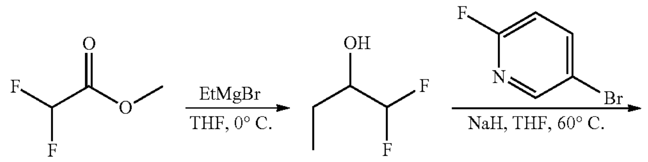

A87 A93

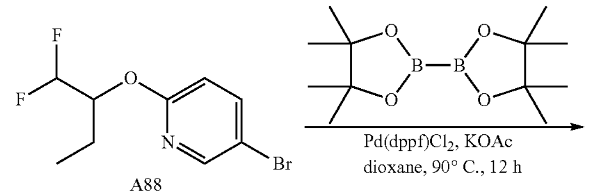

A88

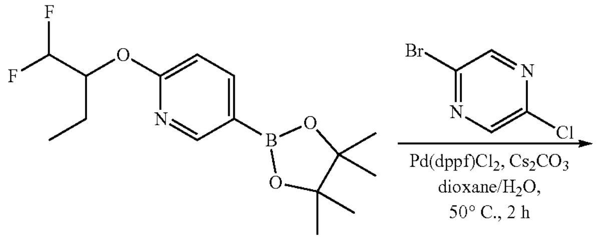

A89

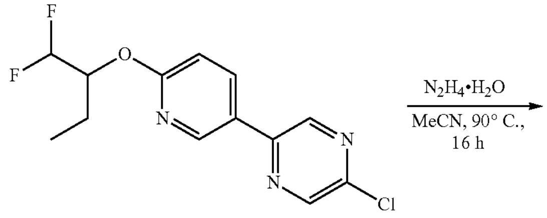

A90

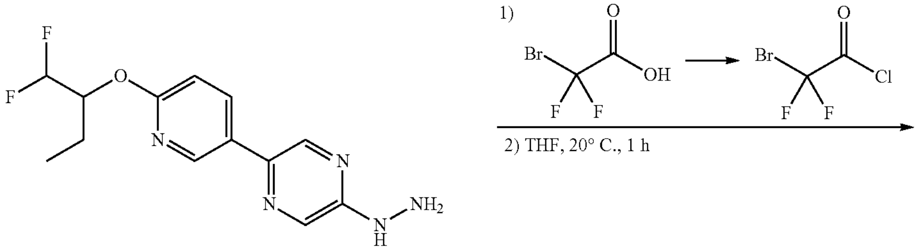

A91

-continued

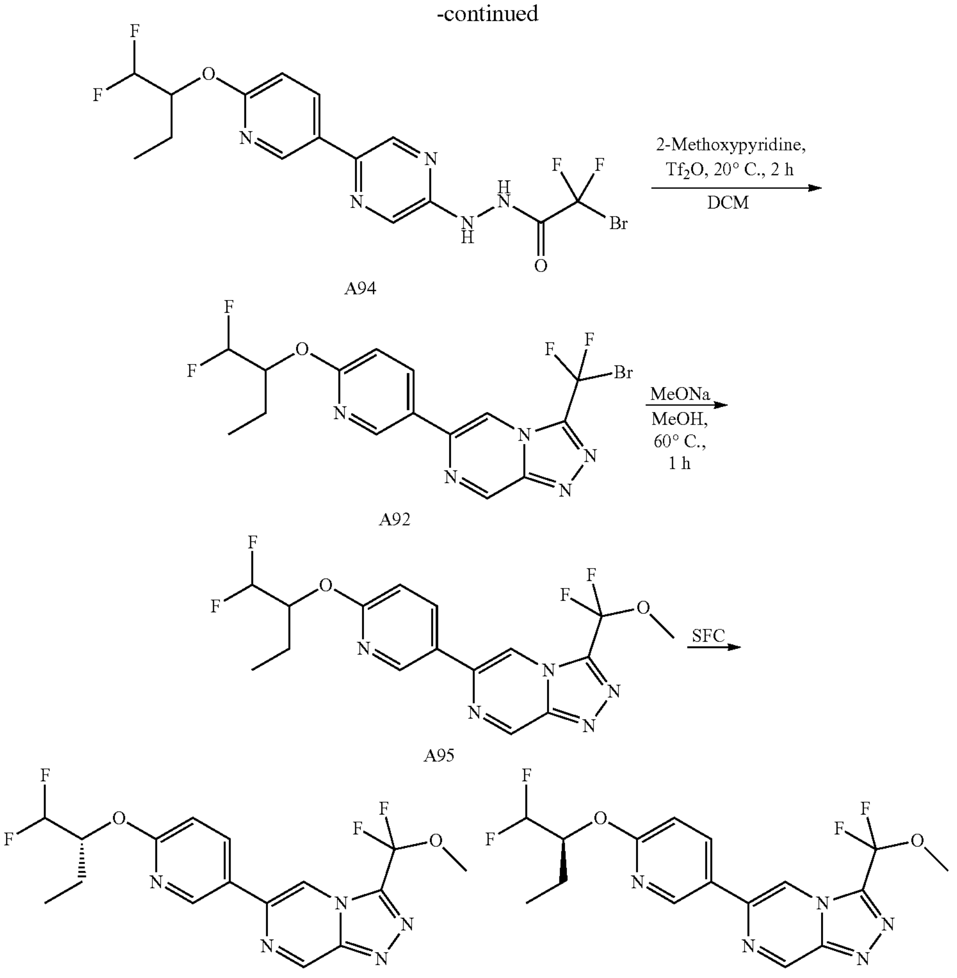

A94

A92

A95

35

36

A93: 1,1-difluorobutan-2-ol

To a mixture of methyl 2,2-difluoroacetate (5 g, 45.43 mmol) and in THF (30 mL) was added EtMgBr (30.3 mL, 90.9 mmol) dropwise (3 M in $Et_2O$) at 0° C. The mixture was warmed to 20° C. and stirred for 2 hours. To the mixture was added saturated $NH_4Cl$ solution (50 mL), and the aqueous layer was extracted with THF (2×20 mL). The combined organic layers were washed with brine (20 mL) and dried over anhydrous $Na_2SO_4$ to afford 1,1-difluorobutan-2-ol (5 g, 13.6 mmol) as an oil, which was used directly in the next step.

A88: 5-bromo-2-[1-(difluoromethyl)propoxy]pyridine

To a solution of 1,1-difluorobutan-2-ol (4.5 g, 40.89 mmol) in THF (50 mL) was added NaH (4.09 g, 102.22 mmol) at 0° C. for 30 minutes. Then 5-bromo-2-fluoropyridine (10.8 g, 61.36 mmol) was added to the resulting mixture, and the mixture was stirred at 60° C. for 16 hours. After cooling to room temperature, the mixture was diluted with saturated $NH_4Cl$ (50 mL) and extracted with EtOAc (2×50 mL). The combined organic phase was washed with brine (30 mL), dried over $Na_2SO_4$, filtered and concentrated to give the crude product, which was purified by flash chromatography on silica gel (EtOAc in PE=0% to 1% to 2%) to give the product (2 g, 6.89 mmol) as an oil. $^1H$ NMR (400 MHz, $CDCl_3$) $\delta_H$=8.20-8.11 (m, 1H), 7.68 (dd, 1H), 6.72 (d, 1H), 6.08-5.72 (m, 1H), 5.42-5.23 (m, 1H), 1.94-1.73 (m, 2H), 1.00 (t, 3H).

A89: 2-[1-(difluoromethyl)propoxy]-5-(4,4,5,5-tetramethyl-1,3,2-dioxaborolan-2-yl)pyridine A mixture of $Pd(dppf)Cl_2$ (0.55 g, 0.75 mmol), KOAc (1.48 g, 15.03 mmol), 5-bromo-2-[1-(difluoromethyl)propoxy]pyridine (2 g, 7.52 mmol) and bis(pinacolato)diboron (2.1 g, 8.27 mmol) in 1,4-dioxane (25 mL) was stirred at 90° C. for 16 hours under $N_2$. The mixture was cooled to room temperature, filtered and concentrated to give the crude product, which was purified by flash chromatography on silica gel (EtOAc in PE=0% to 1% to 2%) to give the product (1.2 g, 3.83 mmol) as an oil. 1H NMR (400 MHz, $CDCl_3$) $\delta_H$=8.49 (s, 1H), 8.02-7.88 (m, 1H), 6.76 (d, 1H), 6.16-5.75 (m, 1H), 5.61-5.33 (m, 1H), 1.95-1.75 (m, 2H), 1.33 (s, 12H), 1.00 (t, 3H).

A90: 2-chloro-5-[6-[1-(difluoromethyl)propoxy]-3-pyridyl]pyrazine

A mixture of $Pd(dppf)Cl_2$ (0.28 g, 0.38 mmol), $Cs_2CO_3$ (2.5 g, 7.66 mmol), 2-bromo-5-chloro-pyrazine (0.82 g, 4.22 mmol) and 2-[1-(difluoromethyl)propoxy]-5-(4,4,5,5-tetramethyl-1,3,2-dioxaborolan-2-yl)pyridine (1.2 g, 3.83 mmol) in 1,4-dioxane (20 mL) and water (2 mL) was stirred at 50° C. for 2 hours under $N_2$. After cooling to 25° C., the aqueous phase was separated, and the organic phase was concentrated to remove most of the dioxane. Then the residue was poured into water (30 mL) and extracted with EtOAc (2×60 mL). The combined organic phase was washed with water (40 mL) and brine (40 mL), dried over $Na_2SO_4$, filtered and concentrated. The crude product was purified by flash chromatography on silica gel (EtOAc in PE=0% to 1% to 3% to 20%) to give the product (1 g, 3.34 mmol, 87% yield) as a solid. $^1H$ NMR (400 MHz, $CDCl_3$) $\delta_H$=8.76-8.73 (m, 2H), 8.65-8.60 (m, 1H), 8.24 (dd, 1H), 6.94 (d, 1H), 6.17-5.77 (m, 1H), 5.60-5.36 (m, 1H), 1.98-1.79 (m, 2H), 1.04 (t, 3H).

A91: [5-[6-[1-(difluoromethyl)propoxy]-3-pyridyl] pyrazin-2-yl]hydrazine

A solution of 2-chloro-5-[6-[1-(difluoromethyl)propoxy]-3-pyridyl]pyrazine (1 g, 3.34 mmol) and $N_2H_4.H_2O$ (3.34 g, 66.73 mmol) in MeCN (15 mL) was stirred at 90° C. under $N_2$ for 16 hours. After cooling to room temperature, the solution was concentrated to give a residue. The residue was diluted with water (50 mL) and extracted with EtOAc (2×50 mL). The combined organic phase was washed with brine (2×50 mL), dried over anhydrous $Na_2SO_4$, filtered and concentrated to give the product (0.95 g, 3.22 mmol, 96% yield) as a solid. $^1H$ NMR (400 MHz, $CDCl_3$) $\delta_H$=8.61-8.54 (m, 1H), 8.40 (d, 1H), 8.27 (d, 1H), 8.16-8.09 (m, 1H), 6.91-6.82 (m, 1H), 6.13-5.80 (m, 1H), 5.49-5.33 (m, 1H), 4.55 (s, 3H), 1.92-1.84 (m, 2H), 1.08-0.96 (m, 3H).

A94: 2-bromo-N'-[5-[6-[1-(difluoromethyl) propoxy]-3-pyridyl]pyrazin-2-yl]-2,2-difluoro-acetohydrazide To a solution of 2-bromo-2,2-difluoro-acetic acid (620 mg, 3.54 mmol) and DMF (0.5 mL) in THF (5 mL) was added $(COCl)_2$ (0.36 mL, 4.25 mmol), and the mixture was stirred at 0° C. for 1 hour. To the resulting solution was added [5-[6-[1-(difluoromethyl)propoxy]-3-pyridyl] pyrazin-2-yl]hydrazine (0.95 g, 3.22 mmol), and the mixture was stirred at 20° C. for 1 hour. After cooling to room temperature, the mixture was poured into water (30 mL) and extracted with EtOAc (2×20 mL). The combined organic phase was washed with brine (2×20 mL), dried over anhydrous $Na_2SO_4$, filtered and concentrated to give the product (0.95 g, 2.1 mmol) as an oil. LCMS Rt=1.00 min in 1.5 min chromatography, 5-95AB, MS ESI calcd. for $C_{15}H_{17}BrF_4N_5O_2$ $[M+3H]^+$ 454.0, found 454.0.

A92: 3-[bromo(difluoro)methyl]-6-[6-[1-(difluoromethyl)propoxy]-3-pyridyl]-[1,2,4]triazolo[4,3-a]pyrazine To a solution of 2-bromo-N'-[5-[6-[1-(difluoromethyl) propoxy]-3-pyridyl]pyrazin-2-yl]-2,2-difluoro-acetohydrazide (0.95 g, 2.1 mmol) in DCM (15 mL) was added 2-methoxypyridine (0.92 g, 8.4 mmol) and $Tf_2O$ (0.71 mL, 4.2 mmol). After stirring at 20° C. for 2 hours, the reaction was poured into water (10 mL) and extracted with EtOAc (3×10 mL). The combined organic phase was washed with saturated $NaHCO_3$ (2×10 mL), brine (10 mL), dried over anhydrous $Na_2SO_4$, filtered and concentrated. The residue was purified by flash column chromatography (0 to 15% of EtOAc in PE) to the product (120 mg, 0.28 mmol, 13% yield) as an oil. $^1H$ NMR (400 MHz, $CDCl_3$) $\delta_H$=9.57 (d, 1H), 8.78-8.71 (m, 1H), 8.43-8.37 (m, 1H), 8.26-8.18 (m, 1H), 6.99 (d, 1H), 6.1-5.78 (m, 1H), 5.56-5.40 (m, 1H), 1.99-1.81 (m, 2H), 1.06 (t, 3H).

A95: 3-[difluoro(methoxy)methyl]-6-[6-[1-(difluoromethyl)propoxy]-3-pyridyl]-[1,2,4]triazolo[4,3-a] pyrazine To a solution of 3-[bromo(difluoro)methyl]-6-[6-[1-(difluoromethyl)propoxy]-3-pyridyl]-[1,2,4]triazolo[4,3-a] pyrazine (120 mg, 0.28 mmol) in methanol (5 mL) was added NaOMe (29.86 mg, 0.55 mmol), and the resulting mixture was stirred at 60° C. for 2 hours. After cooling to room temperature, the reaction was quenched with water (10 mL) and extracted with EtOAc (2×10 mL). The combined organic layer was washed with brine (10 mL), dried over $Na_2SO_4$, filtered and concentrated to give the product (90 mg, 0.19 mmol, 68% yield) as a solid. LCMS Rt=1.63 min in 2.0 min chromatography, 10-80AB, MS ESI calcd. for $C_{16}H_{16}F_4N_5O_2[M+H]^+$ 386.2, found 386.2.

Compound 35: 3-[difluoro(methoxy)methyl]-6-[6-[(1R)-1-(difluoromethyl)propoxy]-3-pyridyl]-[1,2,4] triazolo[4,3-a]pyrazine The racemic product was purified by SFC (DAICEL CHIRALCEL OJ-H (250 mm×30 mm, 5 μm); A: $CO_2$ B=EtOH 0.1% $NH_3.H_2O$; 15% B) to give the product of 3-[difluoro(methoxy)methyl]-6-[6-[rac-(1R)-1-(difluoromethyl)propoxy]-3-pyridyl]-[1,2,4]triazolo[4,3-a]pyrazine (8.51 mg, 0.0213 mmol) as a solid. $^1H$ NMR (400 MHz, $CDCl_3$) $\delta_H$=9.57-9.46 (m, 1H), 8.73-8.68 (m, 1H), 8.44-8.40 (m, 1H), 8.24-8.19 (m, 1H), 6.97 (d, J=8.8 Hz, 1H), 6.14-5.83 (m, 1H), 5.56-5.40 (m, 1H), 3.96 (s, 3H), 1.97-1.82 (m, 2H), 1.05 (t, J=7.6 Hz, 3H). LCMS Rt=1.63 min in 2.0 min chromatography, 10-80AB, MS ESI calcd. for $C_{16}H_{16}F_4N_5O_2[M+H]^+$ 386.2, found 386.2.

Compound 36: 3-[difluoro(methoxy)methyl]-6-[6-[(1S)-1-(difluoromethyl)propoxy]-3-pyridyl]-[1,2,4] triazolo[4,3-a]pyrazine The racemic product was purified by SFC (DAICEL CHIRALCEL OJ-H (250 mm×30 mm, 5 μm); A: $CO_2$ B=0.1% $NH_3.H_2O$; 15% B) to give impure product, which was purified by second SFC (DAICEL CHIRALCEL OJ-H (250 mm×30 mm, 5 μm); A: $CO_2$ B=0.1% $NH_3.H_2O$; 15% B) to give impure product. The impure product was purified by prep-TLC (PE:EA=2:1) to give 3-[difluoro(methoxy) methyl]-6-[6-[rac-(1S)-1-(difluoromethyl)propoxy]-3-pyridyl]-[1,2,4]triazolo[4,3-a]pyrazine (3.01 mg, 0.0076 mmol) as a solid. $^1H$ NMR (400 MHz, $CDCl_3$) $\delta_H$=9.57-9.46 (m, 1H), 8.73-8.68 (m, 1H), 8.44-8.40 (m, 1H), 8.24-8.19 (m, 1H), 6.97 (d, 1H), 6.14-5.83 (m, 1H), 5.56-5.40 (m, 1H), 3.96 (s, 3H), 1.97-1.82 (m, 2H), 1.05 (t, J=7.6 Hz, 3H). LCMS Rt=1.63 min in 2.0 min chromatography, 10-80AB, MS ESI calcd. for $C_{16}H_{16}F_4N_5O_2[M+H]^+$ 386.2, found 386.2.

Example 24: Synthesis of A58: 3-[bromo(difluoro)methyl]-6-[6-[(1R)-2,2,2-trifluoro-1-methyl-ethoxy]-3-pyridyl]-[1,2,4]triazolo[4,3-a]pyrazine

-

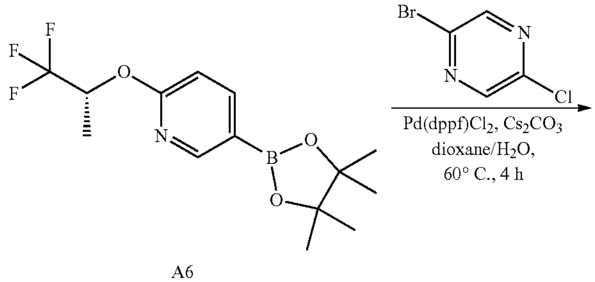

A6

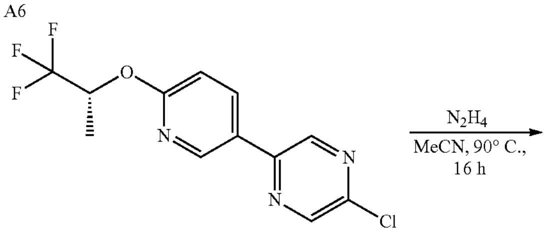

A96

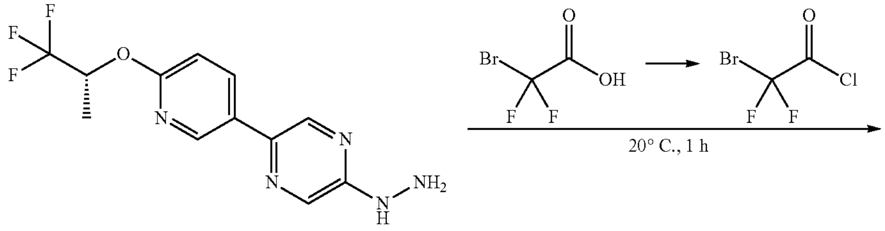

A97

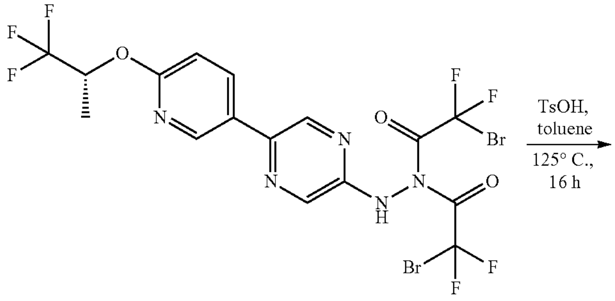

A98

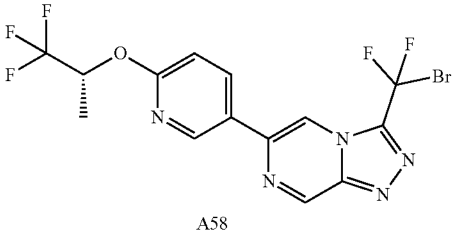

A58

Synthesis of A96: A mixture of 5-(4,4,5,5-tetramethyl-1,3,2-dioxaborolan-2-yl)-2-[(1R)-2,2,2-trifluoro-1-methyl-ethoxy]pyridine (200 g, 630.7 mmol), 2-bromo-5-chloro-pyrazine (122 g, 630.7 mmol), $Pd(dppf)Cl_2$ (46.15 g, 63.07 mmol) and $Cs_2CO_3$ (513.7 g, 1.58 mol) in 1,4-dioxane (2000 mL) and water (500 mL) was stirred at 50° C. for 2 hours under $N_2$. After cooling to 25° C., the mixture was separated and the organic phase was concentrated to remove most of dioxane. The residue was poured into water (1 L) and the mixture was extracted with EtOAc (800 mL×2). The combined organic phase was washed with water (500 mL) and brine (500 mL), dried over anhydrous $Na_2SO_4$, filtered and concentrated. The crude product was purified by flash chromatography on silica gel (EtOAc in PE=000 to 1% to 3% to 20%) to give the product (122 g, 401.75 mmol, 64% yield) as a solid. $^1H$ NMR (400 MHz, $CDCl_3$) $\delta_H$=8.77-8.73 (m, 2H), 8.63 (d, 1H), 8.26 (dd, 1H), 6.96 (d, 1H), 5.93-5.82 (m, 1H), 1.54 (d, 3H).

Synthesis of A97: To a solution of 2-chloro-5-[6-[(1R)-2,2,2-trifluoro-1-methyl-ethoxy]-3-pyridyl]pyrazine (122 g, 401.75 mmol) in MeCN (1000 mL) was added hydrazine (128.76 g, 4.02 mol) at 25° C. The mixture was stirred at 90° C. for 16 hours. After cooling to 25° C., the reaction was poured into water (2 L) and the solid was collected by filtration and washed with water (500 mL×2). The solid was dissolved in EtOAc (1500 mL) and the mixture was washed with brine (500 mL), dried over anhydrous $Na_2SO_4$, filtered and concentrated to give the crude product (120 g, 401 mmol) as a solid. LCMS Rt=0.96 min in 2 min chromatography, 10-80AB, MS ESI calcd. For $C_{12}H_{13}F_3N_5O$ $[M+H]^+$ 300.1, found 299.9.

Synthesis of A98: To a solution of 2-bromo-2,2-difluoro-acetic acid (91 g, 520.21 mmol) in THF (1000 mL) was added one drop DMF and $(COCl)_2$ (52.82 mL, 624.25 mmol). The mixture was stirred at 20° C. for 30 mins. Then [5-[6-[(1R)-2,2,2-trifluoro-1-methyl-ethoxy]-3-pyridyl] pyrazin-2-yl]hydrazine (120 g, 401 mmol) was added to the solution. The mixture was stirred at 20° C. for 1 hour. The mixture was poured in to water (2 L) and the aqueous layer was extracted with EtOAc (2 L×2). The combined organic phase was washed with brine (1 L×2), dried over anhydrous $Na_2SO_4$, filtered and concentrated to give the product (180 g, 293.6 mmol) as a solid.

Synthesis of A58: To a solution of 2-bromo-2,2-difluoro-N'-[5-[6-[(1R)-2,2,2-trifluoro-1-methyl-ethoxy]-3-pyridyl] pyrazin-2-yl]acetohydrazide (180 g, 293.6 mmol) in toluene (1500 mL) was added TsOH (5.18 g, 30.07 mmol). The mixture was stirred at 125° C. for 16 hours. After cooling to room temperature, the mixture was poured in to water (1.5 L) and the aqueous layer was extracted with EtOAc (1.5 L×2). The combined organic phase was washed with brine (500 mL×2), dried over anhydrous $Na_2SO_4$, filtered and concentrated. The crude product was purified by flash chromatography on silica gel (EtOAc in PE=10% to 20%) to give the product (55 g, 125.57 mmol, 31% yield) as a solid. $^1H$ NMR (400 MHz, $CDCl_3$) $\delta_H$=9.59 (d, 1H), 8.76 (d, 1H), 8.41 (d, 1H), 8.25 (dd, 1H), 7.01 (d, 1H), 5.96-5.80 (m, 1H), 1.56 (d, 3H).

Example 25: Efficacy of Exemplary Compounds in the Modulation of Late Sodium Current (INaL)

Functional characterization of exemplary compounds to modulate INaL expressed by the NaV1.6 voltage-gated sodium channel was accomplished using the PatchXpress™ high throughput electrophysiology platform (Molecular Devices, Sunnyvale, CA). HEK-293 cells expressing recombinant, human NaV1.6 (hNaV1.6) were grown in DMEM/high-glucose Dulbecco's modified, 10% FBS, 2 mM sodium pyruvate, 10 mM HEPES and 400 µg/mL G418. Cells were grown to 50%-80% confluency prior to harvesting. Trypsinized cells were washed, allowed to recover for 1 hour and then resuspended in extracellular recording solution at a concentration of 1×106 cells/ml. The onboard liquid handling facility of the PatchXpress was used for dispensing cells and applying test compounds. NaV late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a Na+ free solution containing an impermeant cation (e.g., Choline or NDMG) was added to confirm the identity of the sodium current. Percent steady-state inhibition of INaL was calculated as: [(INaL_compound)/(INaL_control)]*100, where INaL_compound and INaL_control represent INaL recorded in the presence or absence of compound, respectively.

Results from this assay relating to percent inhibition of INaL at hNaV1.6 (measured using a procedure similar to described above but using HEK-293 cells expressing recombinant, human NaV 1.6 (h NaV 1.6) at 1 µM are summarized in Table 1 below. In this table, "A" indicates inhibition of less than 30%; "B" indicates inhibition of between about 30% to about 70%; and "C" indicates inhibition of greater than 70%. "N/A" indicates not available.

TABLE 1

| Compound No. | NaV 1.6 Assay Data |
|---|---|
| 1 | C |
| 2 | C |
| 3 | C |
| 4 | C |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | B |
| 17 | C |
| 18 | C |
| 19 | C |
| 20 | C |
| 21 | C |
| 22 | C |
| 23 | C |
| 24 | C |
| 25 | C |
| 26 | B |
| 27 | C |
| 28 | C |
| 29 | C |
| 30 | C |
| 31 | N/A |
| 32 | N/A |
| 33 | N/A |
| 34 | N/A |
| 35 | N/A |
| 36 | N/A |

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A compound having the Formula I:

(I)

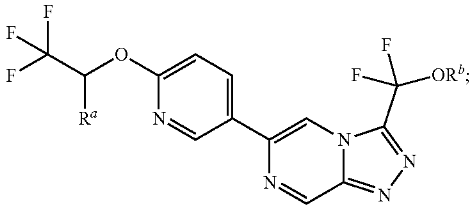

or a pharmaceutically acceptable salt thereof, wherein $R^a$ is $C_{2-4}$alkyl or monocyclic $C_{3-6}$ cycloalkyl; and $R^b$ is $C_{1-4}$alkyl.

2. The compound of claim 1, wherein $R^a$ is ethyl, isopropyl, or cyclopropyl.

3. The compound of claim 1, wherein $R^b$ is methyl or ethyl.

4. The compound of claim 1, wherein the compound is selected from the group consisting of:

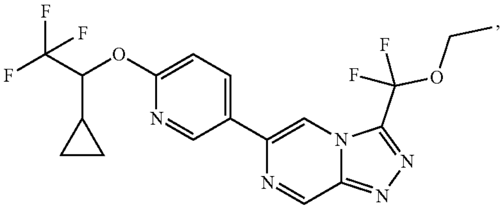

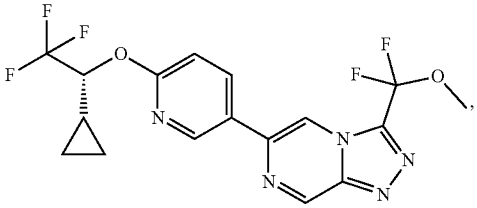

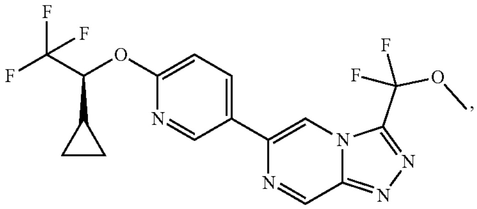

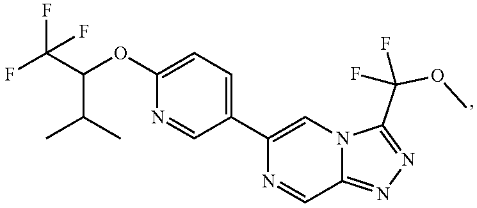

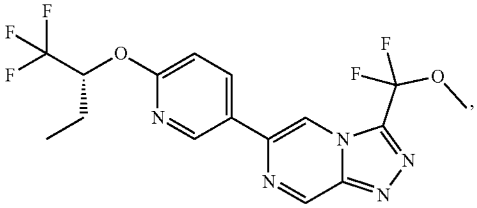

-continued

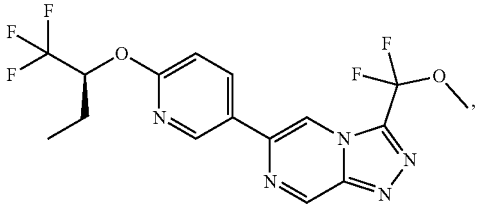

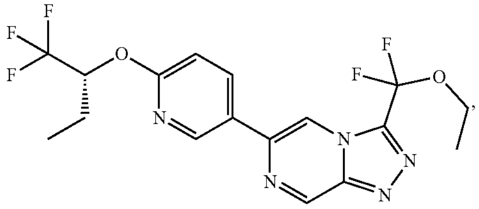

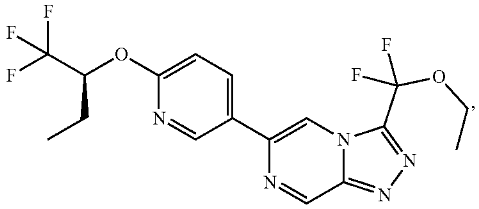

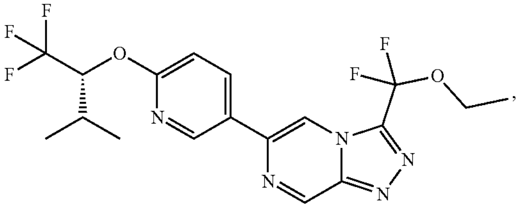

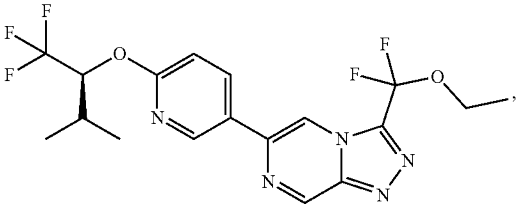

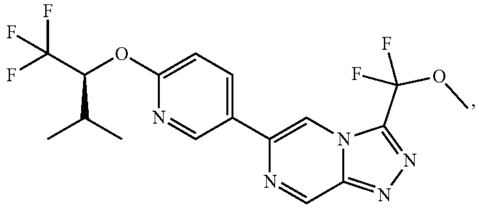

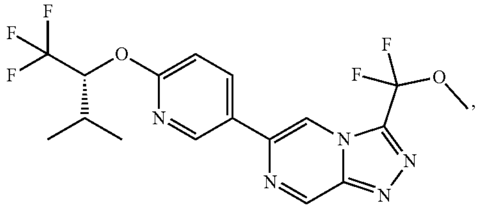

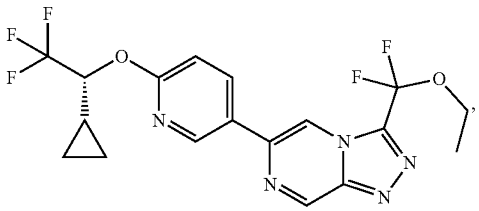

-continued

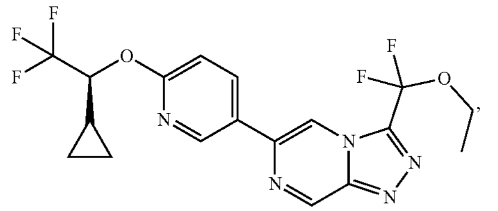

or a pharmaceutically acceptable salt thereof.

5. A compound having the Formula II:

(II)

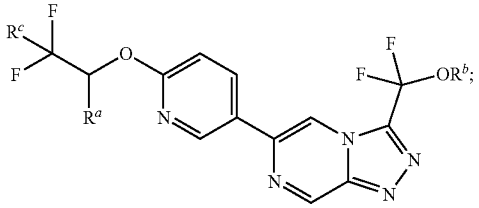

or a pharmaceutically acceptable salt thereof, wherein $R^a$ is $C_{1-4}$alkyl;

$R^b$ is $C_{1-4}$alkyl; and $R^c$ is hydrogen or $C_{1-4}$alkyl.

6. The compound of claim 5, wherein $R^a$ is methyl or ethyl.

7. The compound of claim 5, wherein $R^b$ is methyl, ethyl, or isopropyl.

8. The compound of claim 5, wherein $R^c$ is hydrogen or methyl.

9. The compound of claim 5, wherein $R^c$ is hydrogen.

10. The compound of claim 5, wherein $R^c$ is methyl.

11. The compound of claim 5, wherein the compound is selected from the group consisting of:

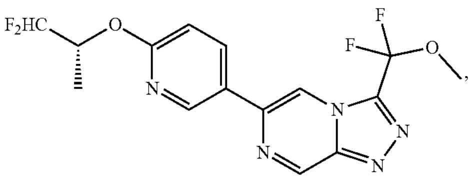

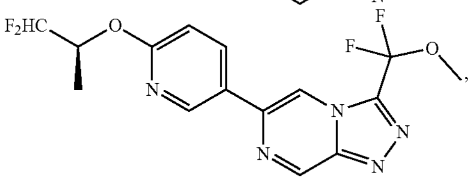

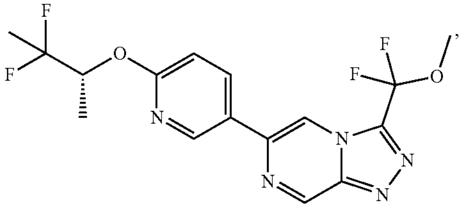

-continued

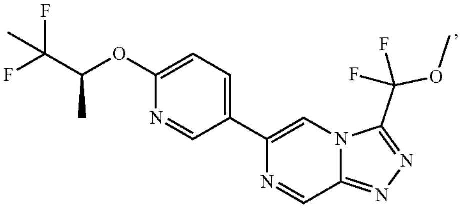

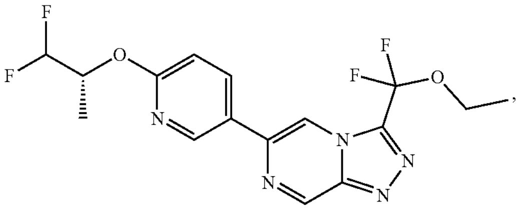

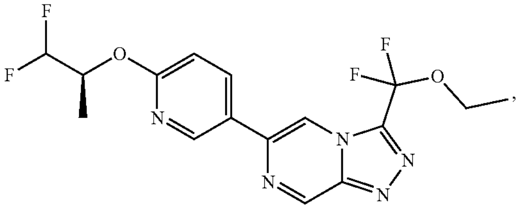

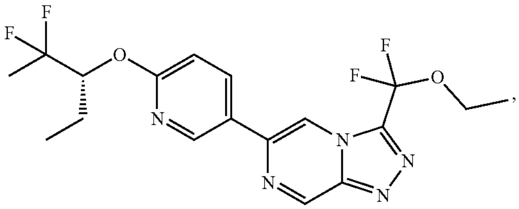

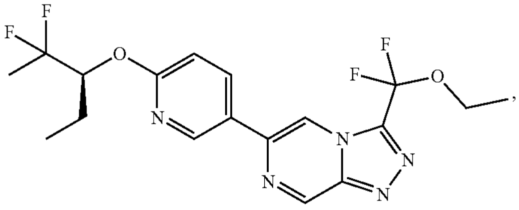

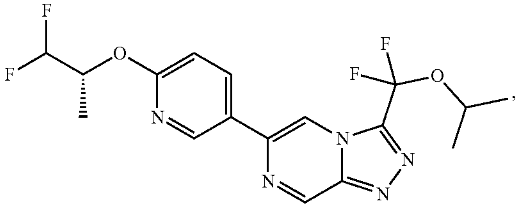

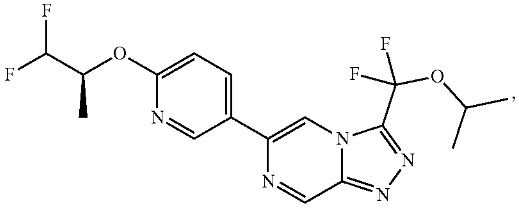

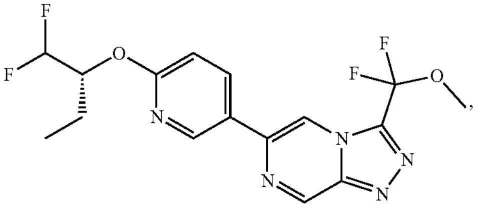

and

-continued

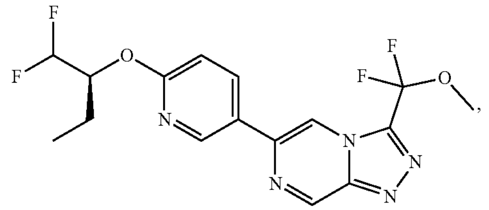

or a pharmaceutically acceptable salt thereof.

12. A compound selected from the group consisting of:

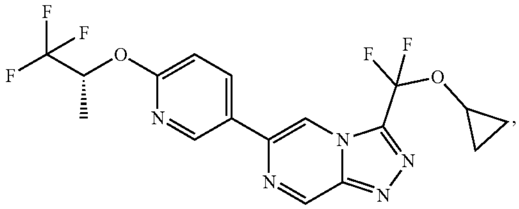
,

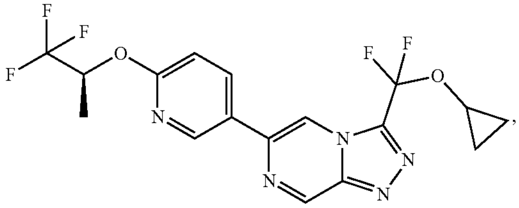
,

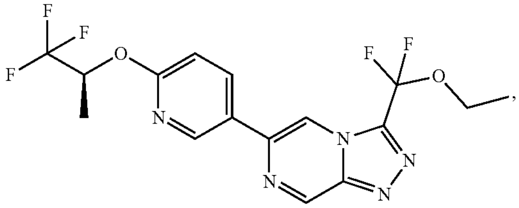
,

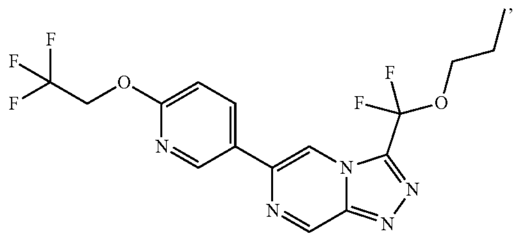
,

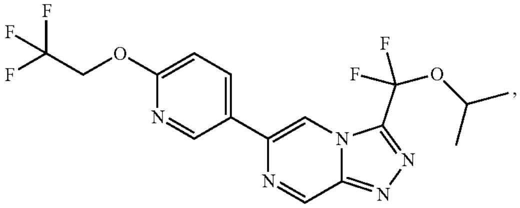
,

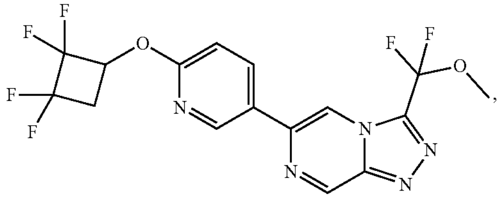
,

-continued

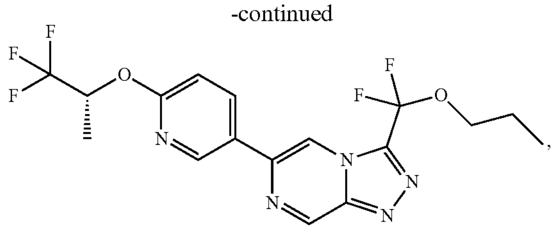
,

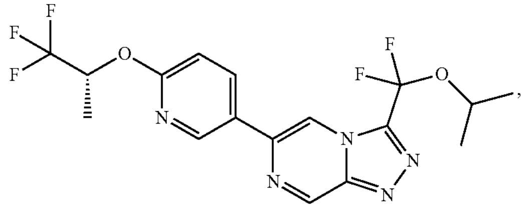
,

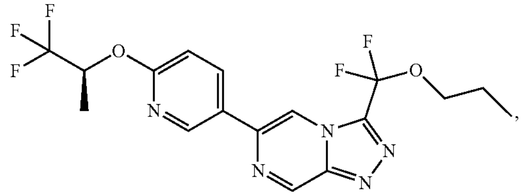
, and

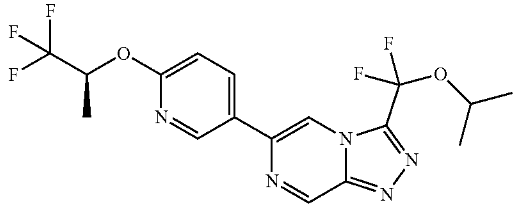

or a pharmaceutically acceptable salt thereof.

13. A pharmaceutical composition comprising a compound of claim 1, or a pharmaceutically acceptable salt thereof; and a pharmaceutically acceptable carrier.

14. A method of treating a condition relating to aberrant function of a sodium ion channel in a subject in need thereof, comprising administering to the subject a therapeutically effective amount of a pharmaceutical composition of claim 13.

15. The method of claim 14, wherein the condition is a neurological or psychiatric disorder.

16. The method of claim 14, wherein the condition is epilepsy or an epilepsy syndrome.

17. The method of claim 14, wherein the condition is a genetic epilepsy or a genetic epilepsy syndrome.

18. The method of claim 14, wherein the condition is a pediatric epilepsy or a pediatric epilepsy syndrome.

19. The method of claim 14, wherein the condition is epileptic encephalopathy.

20. The method of claim 19, wherein the epileptic encephalopathy is selected from the group consisting of Dravet syndrome, infantile spasms, or Lennox-Gastaut syndrome.

21. The method of claim 14, wherein the condition is selected from the group consisting of epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

22. A method of treating a neurological disorder or a psychiatric disorder, wherein the method comprises administering to a subject in need thereof a pharmaceutical composition of claim 13.

23. A method of treating a pain, wherein the method comprises administering to a subject in need thereof a pharmaceutical composition of claim 13.

24. A method of treating or preventing a trigeminal autonomic cephalalgia (TAC) in a subject in need thereof, comprising administering to the subject a therapeutically effective amount of a pharmaceutical composition of claim 13, wherein the TAC is selected from the group consisting of paroxysmal hemicrania, hemicrania continua, short-lasting unilateral neuralgiform headache attacks with conjunctival injection and tearing (SUNCT), short-lasting unilateral neuralgiform headache attacks with cranial autonomic symptoms (SUNA), and long-lasting autonomic symptoms with hemicrania.

25. The method of claim 24, wherein the TAC is a short-lasting unilateral neuralgiform headache attack.

26. The method of claim 24, wherein the TAC is SUNCT.

27. The method of claim 24, wherein the TAC is SUNA.

28. The method of claim 24, wherein the subject has an inadequate response to at least one medication used for the treatment of a TAC.

29. A method of treating or preventing a migraine in a subject in need thereof, comprising administering to the subject a therapeutically effective amount of a pharmaceutical composition of claim 13, wherein the migraine is selected from the group consisting of migraine without aura, migraine with aura, familial hemiplegic migraine type 1 (FHM1), familial hemiplegic migraine type 2 (FHM2), familial hemiplegic migraine type 4 (FHM4), and sporadic hemiplegic migraine (SHM).

30. The method of claim 29, wherein the migraine is migraine without aura.

31. The method of claim 29, wherein the migraine is migraine with aura.

32. The method of claim 29, wherein the migraine is FHM1.

33. The method of claim 29, wherein the migraine is FHM2.

34. The method of claim 29, wherein the migraine is FHM4.

35. The method of claim 29, wherein the migraine is SHM.

36. The method of claim 29, wherein the subject has an inadequate response to at least one medication used for the treatment of a migraine.

37. A method of treating or preventing cortical spreading depression (CSD) in a subject in need thereof, comprising administering to the subject a therapeutically effective amount of a pharmaceutical composition of claim 13.

38. A method of treating or preventing a cranial neuropathy or multiple cranial neuropathies in a subject in need thereof, comprising administering to the subject a therapeutically effective amount of a pharmaceutical composition of claim 13, wherein the cranial neuropathy is selected from the group consisting of bell palsy, microvascular cranial nerve palsy, third nerve palsy, fourth nerve palsy, and sixth nerve palsy.

* * * * *